United States Patent
Davioud-Charvet et al.

(10) Patent No.: US 9,174,960 B2
(45) Date of Patent: Nov. 3, 2015

(54) COMPOUNDS USEFUL AGAINST KINETOPLASTIDEAE PARASITES

(75) Inventors: Elisabeth Davioud-Charvet, Strasbourg (FR); Ingrid Nicole Wenzel, Winkelhaid (DE); Thomas J. J. Müller, Dusseldorf (DE); Gilles Hanquet, Obernai (FR); Don Antoine Lanfranchi, Sarrala Carcopino (FR); Frédéric Leroux, Herrlisheim (FR); Thibault Gendron, Strasbourg (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 13/395,571

(22) PCT Filed: Sep. 20, 2010

(86) PCT No.: PCT/EP2010/063825
§ 371 (c)(1),
(2), (4) Date: May 7, 2012

(87) PCT Pub. No.: WO2011/033115
PCT Pub. Date: Mar. 24, 2011

(65) Prior Publication Data
US 2012/0214996 A1    Aug. 23, 2012

(30) Foreign Application Priority Data
Sep. 18, 2009 (EP) ........................... 09290719

(51) Int. Cl.
| | | |
|---|---|---|
| C07D 335/02 | (2006.01) |
| A61K 31/382 | (2006.01) |
| C07C 49/217 | (2006.01) |
| C07C 49/235 | (2006.01) |
| C07C 49/248 | (2006.01) |
| C07C 49/255 | (2006.01) |
| C07C 233/33 | (2006.01) |
| C07C 255/56 | (2006.01) |
| C07D 211/74 | (2006.01) |
| C07D 213/50 | (2006.01) |
| C07D 213/53 | (2006.01) |
| C07D 311/14 | (2006.01) |
| C07D 401/14 | (2006.01) |
| C07D 409/04 | (2006.01) |
| C07D 409/14 | (2006.01) |

(52) U.S. Cl.
CPC ............ *C07D 335/02* (2013.01); *C07C 49/217* (2013.01); *C07C 49/235* (2013.01); *C07C 49/248* (2013.01); *C07C 49/255* (2013.01); *C07C 233/33* (2013.01); *C07C 255/56* (2013.01); *C07D 211/74* (2013.01); *C07D 213/50* (2013.01); *C07D 213/53* (2013.01); *C07D 311/14* (2013.01); *C07D 401/14* (2013.01); *C07D 409/04* (2013.01); *C07D 409/14* (2013.01)

(58) Field of Classification Search
USPC .......................................... 544/335
See application file for complete search history.

(56) References Cited

U.S. PATENT DOCUMENTS

| 3,636,041 A | 1/1972 | Schmidt et al. |
| 4,297,354 A * | 10/1981 | Weber et al. ............... 514/231.5 |
| 5,013,849 A | 5/1991 | Rule et al. |
| 5,039,585 A | 8/1991 | Rule et al. |
| 5,618,950 A | 4/1997 | Detty et al. |
| 2007/0060644 A1 | 3/2007 | Vander Jagt et al. |

FOREIGN PATENT DOCUMENTS

| EP | 0031456 A1 | 7/1981 |
| WO | 2004009023 A2 | 1/2004 |
| WO | 2008003155 A2 | 1/2008 |

OTHER PUBLICATIONS

Leishmaniasis. PubMed Health (2011). Available Online: http://www.ncbi.nlm.nih.gov/pubmedhealth/PMH0002362/?report=printable.*
Chagas Disease: Prevention & Control. CDC (2010). Available Online: http://www.cdc.gov/parasites/chagas/prevent.html.*
African Trypanosomiasis: Prevention & Control. CDC (2012). Available Online: http://www.cdc.gov/parasites/sleepingsickness/prevent.html.*
Thiruvalluvar, A. Acta Cryst. (2008). E64, 02367.*
Rosowsky, A. Journal of Medicinal Chemistry, 1973, vol. 16, No. 3.*
LaVoie, Edmond J. Chem. Rev. 1996, 96, 3147-3176.*
Stuart, Ken. The Journal of Clinical Investigation. 118:4 2008.*
Maya, Juan. Comparative Biochemistry and Physiology. Part A 146 (2007) 601-620.*
N. Geoffrey Rule, Michael R. Detty, Jeanne E. Kaeding, John A. Sinicropi: "Syntheses of 4H-Thiopyran-4-one 1, 1-Dioxides as Precursors to Sulfone-Containing Analogs of Tetracyanoquinodimethane", The Journal of Organic Chemistry, vol. 60, No. 6, Mar. 1995, pp. 1665-1673, XP002577740.
Chen et al, J. Org. Chem. (1986), 51, 3832-3289), XP-002577743.

(Continued)

*Primary Examiner* — Golam M M Shameem
*Assistant Examiner* — Laura Daniel
(74) *Attorney, Agent, or Firm* — Young & Thompson

(57) ABSTRACT

Dibenzylidene and heterobenzylideneacetone derivatives, related 4-piperidones, related 4-thiopyranones and the corresponding sulfinyl- and sulfonyl-analogues for their use for prophylaxis or treatment of trypanosomiasis and leishmaniasis.

10 Claims, 7 Drawing Sheets

(56) References Cited

OTHER PUBLICATIONS

Figure 2:
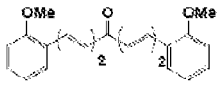

Haller R., Archive Der Pharmazie (1965), 5, 306-312, XP-002577741.
Weber et al: "TPA-induced up-regulation of activator protein-1 can be inhibited or enhanced by analogs of the natural product curcumin", Biochemical Pharmacology (2006), 72, 928-940.
Klein et al: "The Stereochemistry of Thiane Oxidation Participation of Neighboring Groups", Tetrahedron, vol. 30. pp. 2541-2548, XP-002577742.
International Search Report, dated Apr. 7, 2011, in PCT/EP2010/063825.
Devanathan et al., "1H and 13C NMR Spectral Study of Some 2r-Aryl-6c-phenylthian-4-ones, Their 1-Oxides and 1,1-Dioxides", Spectroscopy Letters, 2009, vol. 42, pp. 143-151, XP008165841.
Gaidelis et al., "Asymmetric dioxothiapyranes as electron transporting materials", Environmental and Chemical Physics, 2001, vol. 23, No. 2, pp. 64-70.
Parthiban et al., "Synthesis, spectral, crystal and antimicrobial studies of biologically potent oxime ethers of nitrogen, oxygen and sulfur heterocycles", Bioorganic & Medicinal Chemistry Letters, 2009, vol. 19, pp. 2981-2985.

* cited by examiner

Table 1

| Structure | Compound | IC₅₀ (µM) | | | | Toxicity |
|---|---|---|---|---|---|---|
| | | MRC-5 | T. cruzi | L. infantum | T. brucei | |
| | NW267 (R₃=CF₃, R₁=R₂=R₄=H) | 26.18 | 1.60 | > 64.00 | < 0.25 | |
| | NW254 (R₃=OCF₃, R₁=R₂=R₄=H) | 32.86 | 1.76 | > 64.00 | 0.46 | |
| | NW247=NW238 (R₃=OMe, R₁=R₂=R₄=H) | > 64.00 | 10.70 | > 64.00 | 1.24 | |
| | NW270 (R₃=acetamide, R₁=R₂=R₄=H) | 8.06 | 1.71 | 32.46 | 0.50 | Toxic |
| | NW268 (R₃=Cl, R₁=R₂=R₄=H) | 9.22 | 1.90 | 8.11 | 0.30 | Toxic |
| | NW275 (R₁=R₂=R₃=R₄=H) | 32.22 | 2.15 | 32.46 | 0.25 | Toxic |
| | NW300 (R₁=R₄=H,R₂=OMe R₃=OH) | > 1.06 | 1.00 | > 32.00 | < 0.32 | |
| | NW307.2 (R₁=R₂=R₄=H, R₃=CN) | 10.36 | 0.97 | 16.57 | < 0.32 | |
| | NW308 (R₁=R₂=R₄=H, R₃=Cl) | > 32.00 | 11.21 | 10.36 | 0.53 | Toxic |
| | NW310.1 (R₁=R₄=H, R₂=CF₃, R₃=OH) | 10.49 | 12.40 | 10.36 | 1.03 | Toxic |
| | NW317 (R₁=R₄=H, R₂=OCF₃, R₃=OH) | > 32.00 | > 32.00 | 10.36 | 0.94 | Toxic |
| | NW324.2 (R₁=R₄=OMe, R₂=Br, R₃=H) | 0.85 | 0.92 | 10.36 | 0.94 | Toxic |
| | NW326.4 (R₁=OH, R₂=Br, R₃=H, R₄=OMe) | 0.96 | < 0.32 | 1.04 | < 0.32 | Toxic |
| | NW327.2 (R₁=OH, R₂=R₃=H, R₄=OMe) | 1.88 | 1.03 | > 32.00 | < 0.32 | |
| | NW331 (R₁=R₄=OMe, R₂=R₃=H) | 1.02 | 1.08 | 10.36 | 0.79 | Toxic |
| | BJ839 (R₁=R₄=OMe, R₂=Br, R₃=Me) | 29.58 | 12.85 | 6.96 | 9.08 | |
| | BJ673K (R₁=R₄=OMe, R₂=H, R₃=SMe) | > 64.00 | > 64.00 | 32.00 | > 64.00 | |
| | BJ679 (R₁=R₄=OMe, R₂=H, R₃=Me) | > 64.00 | > 64.00 | 27.86 | > 64.00 | |

FIGURE 1

Table 2

| Structure | Compound | IC$_{50}$ (µM) | | | |
|---|---|---|---|---|---|
| | | MRC-5 | T. cruzi | L. infantum | T. brucei |
| 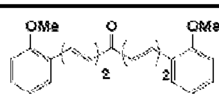 | NW312 | > 32.00 | > 32.00 | > 32.00 | > 32.00 |

Table 3

| Structure | Compound | IC₅₀ (µM) | | | | Toxicity |
|---|---|---|---|---|---|---|
| | | MRC-5 | T. cruzi | L. infantum | T. brucei | |
|  | NW336.2 (R₁=R₂=R₄=H, R'₁=R'₂=R'₄=H, R₃=CF₃, R'₃=OMe) | > 32.00 | 12.32 | > 10.36 | 0.72 | Toxic |
| | NW346 (R₁=R₂=R₄=H, R'₁= R'₄=H,R₃=CF₃, R'₂= OMe, R'₃=OH) | 8.60 | 6.50 | 8.11 | 0.36 | |
| | NW337 (R₁= R₂=R₄=H, R'₁= R'₂=R'₄=H,R₃ =CF₃, R'₃=OCF₃) | 18.86 | 19.54 | > 32.00 | 0.55 | |
| | NW351 (R₁=R₂=R₄=H, R'₁= R'₄=H,R₃=OCF₃, R'₂= OMe, R'₃=OH) | 32.69 | 8.61 | 8.11 | 0.46 | |
| | NW350 (R₁=R₂=R₄=H, R'₁=R'₂=R'₄=H, R₃=OCF₃, R'₃=OMe) | > 64.00 | > 64.00 | 16.97 | > 64.00 | |
| | NW355.1 (R₁=R₂=R₄=H, R'₁= R'₄=H, R₃=CF₃, R'₂ and R'₃= 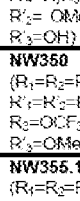) | 8.60 | 6.50 | 8.11 | 0.36 | |

FIGURE 3

Table 4
| Structure | Compound | IC₅₀ (μM) | | | | | | Toxicity |
|---|---|---|---|---|---|---|---|---|
| | | MRC-5 | | T. cruzi | | L. infantum | T. brucei | |
| 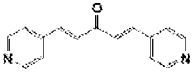 | NW319 | 1.13 | < | 0.32 | | 1.04 | < 0.32 | Toxic |
| 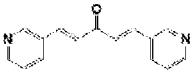 | NW321 | 1.09 | | 0.91 | | 1.04 | < 0.32 | Toxic |
| 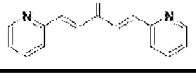 | BJ621 | 1.94 | < | 0.25 | | 1.59 | < 0.25 | Toxic |
FIGURE 4

Table 5
| Structure | Compound | IC₅₀ (µM) | | | | Prodrug (Pro) of Michael Acceptor (MA) |
|---|---|---|---|---|---|---|
| | | MRC-5 | T. cruzi | L. infantum | T. brucei | |
| 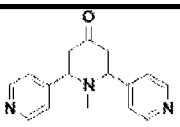 | BJ591 | 20.24 | 1.90 | 8.11 (Toxic) | < 0.25 | (Pro) of NW319 |
| 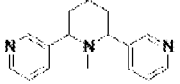 | BJ593 | > 64.00 | > 64.00 | > 64.00 | > 64.00 | (Pro) of NW321 |
| 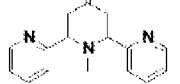 | BJ627 | 7.70 | 0.40 | 8.11 | < 0.25 | (Pro) of BJ621 |
| 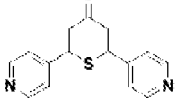 | TG003A23 | > 64.00 (3) | > 64.00 (3) | > 64.00 (3) | 8.17 (2) - 8.11 | (Pro) of NW319 |
FIGURE 5

Table 6

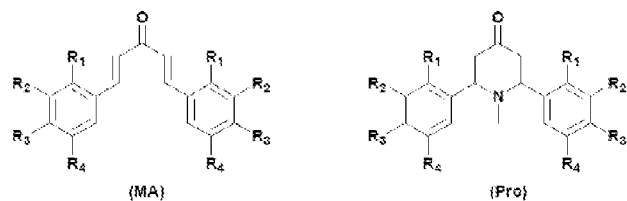

| Compounds | IC$_{50}$ (μM) in triplicate | | | | | Prodrug (Pro) of Michael Acceptor (MA) |
|---|---|---|---|---|---|---|
| | cytotoxicity human MRC-5 | T. cruzi | L. infantum | T. brucei brucei | T. brucei rhodesiense | |
| NW249.1 ($R_1=R_2=R_3=R_4=H$) | > 64.00 - 32.94 (2) | 0.94 - 1.52 - 4.59 | > 64.00 (3) | < 0.25 - 0.08 - 0.09 | 0.20 - 0.13 | (Pro) of NW275 |
| NW275 ($R_1=R_2=R_3=R_4=H$) | 7.65 (T) | 1.60 | 32.22 | < 0.25 | < 0.25 | (MA) |
| NW246.1 ($R_1=R_2=R_4=H$, $R_3=OMe$) | > 64.00 (3) | > 64.00 (3) | > 64.00 (3) | 2.40 - 1.96 - 2.23 | - | (Pro) of NW238=NW247 |
| NW247=238 ($R_1=R_2=R_4=H$, $R_3=OMe$) | > 64.00 | 19.70 | > 64.00 | 1.24 | - | (MA) |
| BJ613.2 ($R_1=Cl$, $R_2=R_3=R_4=H$) | 25.06 | 7.32 | 12.70 | 0.63 | - | (Pro) of NW268 |
| NW268 ($R_1=Cl$, $R_2=R_3=R_4=H$) | 6.11 - 6.82 - 5.60 | 3.61 - 2.32 - 2.49 | 6.11 (2) - 6.82 | < 0.25 - 0.53 - 0.28 | - | (MA) |
| BJ571.1=575 ($R_1=R_2=R_4=H$, $R_3=CF_3$) | 32.22 | 8.26 | 32.00 | 0.79 | - | (Pro) of NW267 |
| NW267 ($R_1=R_2=R_4=H$, $R_3=CF_3$) | 7.65 - 8.06 | 0.34 - 0.25 | > 64.00 (2) | 0.085 - 0.03 | 0.03 - 0.04 | (MA) |
| BJ607.2 ($R_1=R_2=R_4=H$, $R_3=OCF_3$) | 32.00 | 7.34 | 2.00 | 1.82 | - | (Pro) of NW254 |
| NW254 ($R_1=R_2=R_4=H$, $R_3=OCF_3$) | 56.42 | 5.06 | 32.86 | 9.36 | 0.44 | (MA) |
| BJ576=577K ($R_1=R_2=R_4=H$, $R_3=$acetamide) | 8.52 | 2.13 | 8.11 (Toxic) | 9.50 | - | (Pro) of NW270 |
| NW270 ($R_1=R_2=R_4=H$, $R_3=$acetamide) | 8.06 | 1.71 | 32.46 (Toxic) | 9.50 | - | (MA) |
| tamoxifen | 10.0 | | | | | reference |
| nifurtimox | | 1.0 | | | | reference |
| miltefosine | | | 3.56 | | | reference |
| suramin | | | | | 0.02 | reference |
| suramin | | | | 0.02 | | reference |

FIGURE 6

Table 7

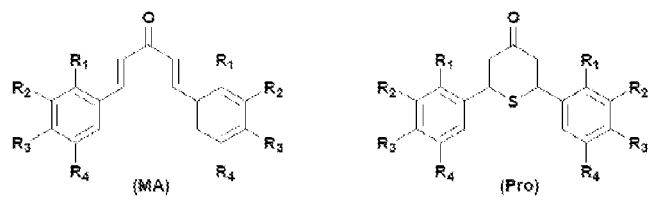

| Compounds | IC$_{50}$ (µM) in triplicate | | | | Prodrug (Pro) of Michael Acceptor (MA) |
|---|---|---|---|---|---|
| | cytotoxicity human MRC-5 | T. cruzi | L. infantum | T. brucei brucei | |
| TG001A21 ($R_1=R_2=R_4=H$, $R_3=OMe$) | > 64.00 (3) | > 64.00 (3) | > 64.00 (3) | > 64.00 (3) | (Pro) of NW247 |
| TG002A22 ($R_1=R_2=R_4=H$, $R_3=OMe$) | > 64.00 (3) | > 64.00 (3) | > 64.00 (3) | > 64.00 (3) | (Pro) of NW247 |
| TG006A44 ($R_1=R_2=R_4=H$, $R_3=OMe$) | > 64.00 (3) | > 64.00 (3) | > 64.00 (3) | > 64.00 (3) | (Pro) of NW247 |
| NW247 ($R_1=R_2=R_4=H$, $R_3=OMe$) | > 64.00 (3) | > 64.00 (3) | > 64.00 (3) | 2.40 - 1.98 - 2.23 | (MA) |
| TG004A23 ($R_1=Cl$, $R_2=R_3=R_4=H$) | > 64.00 (3) | 30.49 - 42.68 - > 64.00 | > 64.00 (3) | 33.99 - 36.88 - 41.90 | (Pro) of NW268 |
| NW268 ($R_1=Cl$, $R_2=R_3=R_4=H$) | 6.11 - 6.82 - 5.60 | 3.61 - 2.32 - 2.49 | 8.11 (2) - 6.82 | < 0.25 - 0.50 - 0.26 | (MA) |
| TG005A25 ($R_3=Cl$, $R_1=R_2=R_4=H$) | > 64.00 - 32.00 - 23.44 | > 64.00 - 19.33 - 23.35 | > 64.00 (3) | > 64.00 - 52.66 - 40.62 | (Pro) of NW308 |
| NW308 ($R_3=Cl$, $R_1=R_2=R_4=H$) | 23.57 - > 64.00 (2) | 31.02 - 32.59 - 35.52 | > 64.00 - 24.05 (2) | 1.03 (2) - 0.97 | (MA) |
| tamoxifen | 10.9 | | | | reference |
| nifurtimox | | 1.67 | | | reference |
| R126 | | | 5.0 | | reference |
| melarsoprol | | | | 0.09 | reference |

FIGURE 7

COMPOUNDS USEFUL AGAINST KINETOPLASTIDEAE PARASITES

FIELD OF THE INVENTION

The present invention relates to the use of dibenzylidene and diheteroarylidene acetones and their derivatives in the prevention and the treatment of diseases due to parasites. The invention also relates to the preparation of the said compounds.

BACKGROUND OF THE INVENTION

Trypanosomes and leishmanias are parasitic protozoa causing African sleeping sickness (*Trypanosoma brucei gambiense* and *Trypanosoma brucei rhodesiense*), Chagas' disease (*Trypanosoma cruzi*), Nagana cattle disease (*Trypanosoma congolense* and *Trypanosoma brucei brucei*), Espundia (*Leishmania brasiliensis*), Kala-azar (*Leishmania donovani*), and Oriental sore (*Leishmania tropica*). All of these parasites have a unique thiol metabolism dependant on the flavoenzyme trypanothione reductase, which maintains bis-glutathionylspermidine (trypanothione) and monoglutathionylspermidine in the reduced state. This thiol system replaces the glutathione/glutathione reductase (GR) system occurring in their mammalian hosts and is widely accepted as a target for the development of novel therapies to treat trypanosomiasis and leishmaniasis.

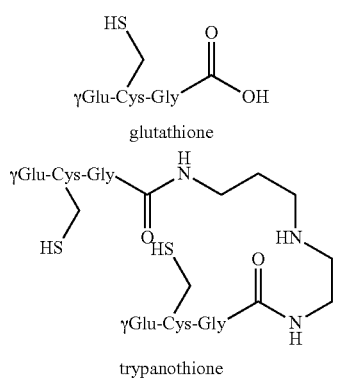

Human African trypanosomiasis is invariably fatal if untreated. Current therapy of the late-stage encephalitic disease with the melaminophenyl arsenical drug melarsoprol has unacceptable side-effects with an overall mortality of more than 5% due to the drug itself. Melarsoprol acting as a bis-alkylating agent of dithiols including trypanothione and trypanothione reductase is actively taken up via adenosine transporters of the parasite which recognize the melamine motif. In the recent years appearance of highly resistant parasites to melarsoprol and pentamidine has become alarming and is responsible for the increasing failure rate (under 7%) of melarsoprol after treatment of late stage case of human African trypanosomiasis (HAT), even though the drug has been used for such treatment over the past 50 years. This observation, the first documented in a HAT focus, is dramatic, particularly since no second line trypanocidal drug is actually available for the treatment of the late stage of HAT.

Eflornithine (=DFMO) is effective against both stages of *T. b. gambiense* infection but not against *T. b. rhodesiense*. Although the most recent and effective drug against sleeping sickness it is not widely available, difficult to administer and costly for use under African health care conditions. For this reason, in 1995, Aventis limited its production because eflornithine was not enough a profitable drug.

Thus there is a need for compounds which are less costly, less toxic, which induce less resistance and which are able to cross the blood brain barrier in the late stage of the disease.

SUMMARY OF THE INVENTION

The inventors have discovered that a divinylketone is the minimal motif for mechanism-based inactivation of the trypanothione based-system and they have designed and synthesized symmetrical and asymmetrical dibenzylidene (and diheteroarylidene) acetone derivatives and other derivatives to protect the reactive α,β-unsaturated ketone.

Several patents disclose dibenzylidene and heterobenzylidene acetone derivatives and related 4-piperidones but with applications as anticancer (WO 2004/009023) or anti-Alzheimer drugs (US2007/0060644).

WO 2008/003155 discloses penta-1,4-dien-3-ones and substituted cyclohexanones showing antitumoral and antiparasitic properties but the 1,5-bis(4-hydroxy-3-methoxyphenyl)-penta-1,4-dien-3-one and the dibenzylidene acetone are the only compound tested for their parasitic effect.

Rule N. J. et al. (J. Org. Chem. (1995), 60, 1665-1673 disclose the synthesis of 4h-thiopyran-4-one but do not give any information on their potential activity.

Haller R. in Archiv der Pharmazie (1965), 5, 306-312 (XP-002577741) discloses the synthesis of 1-thiacyclohexanone but does not give any information on their potential activity.

Weber W. M. et al. (Biochemical Pharmacology (2006), 72, 928-940 disclose analogs of curcumin as modulators of the TP-induced up-regulation of activator protein-1.

Klein J. et at (Tetrahedron (1974), 30, 2541-2548) discuss the stereochemistry of thiane oxidation but does not give any information on the potential activity of the compounds.

Chin H. Chen et at (J. Org. Chem. (1986), 51, 3282-3289) disclose the synthesis of 2,6-diphenyl-4H-thiopyran-4-one but do not give any information on their potential activity.

U.S. Pat. No. 5,013,849 discloses 4h-thiopyran-1,1-dioxides and their use as electron-transport agents in electrophotographic elements.

EP 0031456 discloses 4-amino-2,6-diaryl-tetrahydrothiopyran useful as a antidepressant.

Consequently one aim of the invention is the use of such compounds in the prevention and treatment of diseases caused by kinetoplastidae parasites.

Another aim of the invention is the process for preparing such compounds.

Finally some of the compounds are new and are also part of the invention.

The present invention relates to compounds of formula (I)

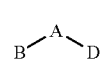

(I)

wherein
A is selected from

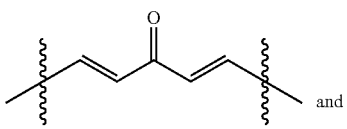

A1 and

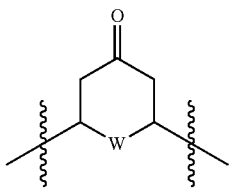

with W representing N—(C$_1$-C$_4$)alkyl, N—C(O)—(C$_1$-C$_5$)alkylamine or S(O)$_p$ with p=0 to 2, B and D each independently of each other represent an aryl group or a heteroaryl group optionally substituted by one to 5 substituents selected from the group comprising hydrogen atom, halogen atoms, hydroxy group, linear or branched (C$_1$-C$_4$)alkyl groups, (C$_1$-C$_4$) alkoxy groups, (C$_1$-C$_4$) thioalkoxy groups, trifluoromethyl group, trifluoromethoxy group, pentafluorosulfanyl group acetamide group,

—OC(O)C$_6$H$_5$, formyl group

—COOH,

—COOR with R representing a (C$_1$-C$_4$)alkyl group,

—CH$_2$OH

—CH$_2$OR' with R' representing a (C$_1$-C$_4$)alkyl group, —CH$_2$OCH$_3$ or a protecting group forming an acetal,

—NH$_2$

—NR$_2$ with R representing a (C$_1$-C$_4$)alkyl group,

—NO$_2$,

—CN, and

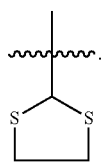 [SMILES: *C1SCCS1]

and the pharmaceutically acceptable salts and derivatives thereof for their use for prophylaxis or treatment of trypanosomiasis and leishmaniasis, sleeping sickness, Chagas' disease, visceral leishmaniases, cutaneous leishmaniases and mucocutaneous leishmaniases, with the proviso that, the following compounds are excluded:

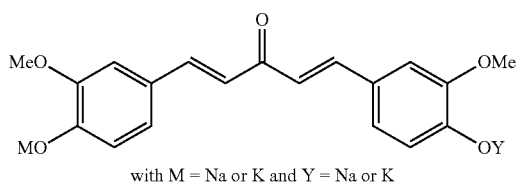

with M = Na or K and Y = Na or K

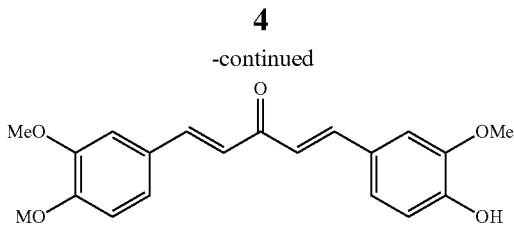

with M = Na or K

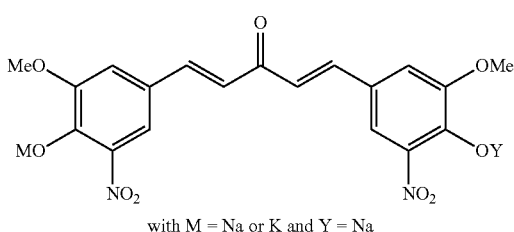

with M = Na or K and Y = Na

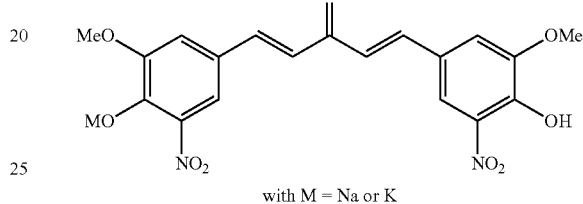

with M = Na or K

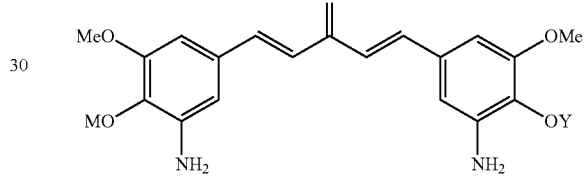

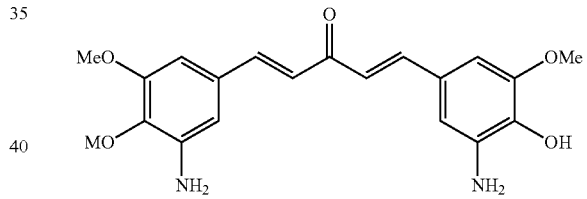

with M = Na or K

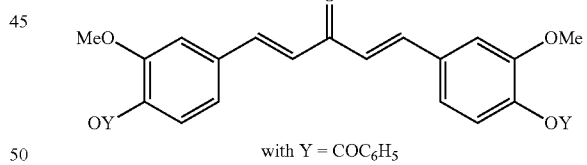

with Y = COC$_6$H$_5$

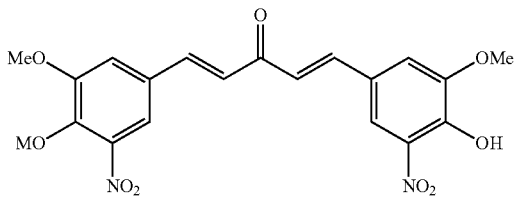

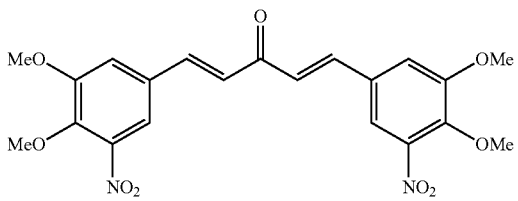

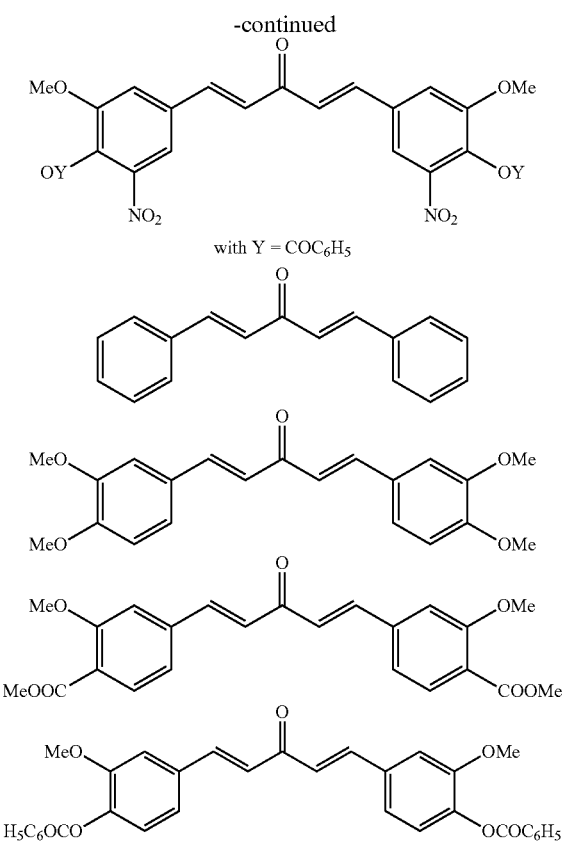

with Y = COC6H5

According to the invention, the term "aryl" as used herein refers to a monocyclic or bicyclic carbocyclic ring system having one or more aromatic rings including, but not limited to, phenyl, naphthyl, tetrahydronaphthyl, indanyl.

According to the invention, the term "heteroaryl" as used herein refers to any mono- or bicyclic aromatic 5- to –12 members ring containing 1 to 5 heteroatoms selected from O, S or N, selected from imidazolyl, pyrazolyl, thiazolyl, oxazolyl, isothiazolyl, isoxazolyl, thiophenyl, oxadiazolyl, thiadiazolyl, triazolyl, tetrazolyl, pyridinyl, pyrazinyl, pyrimidinyl, pyridazinyl, triazinyl as monocyclic rings and including but not limited to indolyl, isoindolyl, benzofuranyl, benzothiophenyl, benzoxazolyl, benzimidazolyl, indazolyl, benzothiazolyl, isobenzofuranyl, isobenzothiazolyl, pyrrolo[2,3-c]pyridinyl, pyrrolo[2,3-b)]pyridinyl, pyrrolo[3,2-b]pyridinyl, pyrrolo[3,2-c]pyridinyl, pyrrolo[1,2-a]pyridinyl, quinolinyl, isoquinolinyl, cinnolinyl, quinazolinyl, quinoxalinyl, pyrrolo[1,2-a]imidazolyl, imidazo[1,2-a]pyridinyl, imidazo[1,2-a]pyridazinyl, imidazo[1,2-c]pyrimidinyl, imidazo[1,2-a]pyrimidinyl, imidazo[1,2-a]pyrazinyl, imidazo[4,5-b]pyrazinyl, imidazo[4,5-b]pyridinyl, imidazo[4,5-c]pyridinyl, pyrazolo[2,3-a]pyridinyl, pyrazolo[2,3-a]pyrimidinyl, pyrazolo[2,3-a]pyrazinyl, 3-(7-hydroxy-coumaryl) also named 7-hydroxy-2H-1-benzopyran-2-one-3-yl, 4-(7-hydroxy-coumaryl) also named 7-hydroxy-2H-1-benzopyran-2-one-4-yl, or 6-(7-hydroxy-coumaryl) also named 7-hydroxy-2H-1-benzopyran-2-one-6-yl as bicyclic rings.

According to the invention the term "halogen" as used herein refers to fluorine, chlorine, bromine and iodine atom.

According to the invention the term "linear or branched $(C_1-C_4)$alkyl" as used herein refers to straight or branched chain alkyl substituents containing from 1 to 4 carbon atoms including methyl, ethyl, n-propyl, isopropyl, n-butyl, isobutyl, sec-butyl and tert-butyl.

According to the invention the term "$(C_1-C_4)$ alkoxy groups" as used herein refers to an alkoxy substituent made up of an oxygen substituent bearing saturated straight or branched chain hydrocarbon substituent of one to four carbon atoms including but not limited to methoxy, ethoxy, propoxy, n-butoxy, isobutoxy, sec-butoxy, tert-butoxy.

According to the invention the term "$(C_1-C_4)$ thioalkoxy groups" as used herein refers to S-alkoxy wherein the alkoxy group is defined above.

According to the invention, the term N—$(C_1-C_4)$alkyl means that N is substituted by a $(C_1-C_4)$alkyl group as defined above, in particular by a methyl group, said alkyl group being optionally substituted by an hydroxy group to form alpha- or omegamino alcohols or by a group able to give amino esters or any other groups in order to improve the solubility and even pharmacokinetics.

According to the invention the term "$(C_1-C_5)$alkylamine" as used herein refers to straight chain alkyl substituent containing from 1 to 5 carbon atoms and bearing a nitrogen atom at the end of the chain. This nitrogen can be mono or disubstituted, each independently of each other, by hydrogen, methyl, ethyl, isopropyl, tert-butyl or protected as a tert-butyl carbamate. This definition is in accordance with the following formula:

n = 1 to 5
$R^1$ = H, methyl, ethyl, isopropyl, tert-butyl or BOC
$R^2$ = H, methyl, ethyl, isopropyl, tert-butyl or BOC According to the invention, the R' group representing a protecting group forming an acetal, may be for example a tetrahydropyranyl group (THP).

According to the invention, kinetoplastidae parasites are primitive flagellated protozoans found in terrestrial and aquatic environments. Some of them cause diseases in organisms ranging from plants to vertebrates. Two major subgroups of Kinetoplastidae are *Leishmania* and *Trypanosomatidae*.

According to the invention, trypanosomiasis and leishmaniasis also include sleeping sickness, Chagas' disease, and visceral leishmaniases, cutaneous leishmaniases and mucocutaneous leishmaniases.

In an advantageous embodiment the invention relates to compounds of formula (I)
wherein
B and D each independently of each other are selected from the group comprising a phenyl group, a 2-pyridyl or a 3-pyridyl or a 4-pyridyl or, a 2-pyrimidinyl, a 2H-1-benzopyran-2-one-3-yl, a 2H-1-benzopyran-2-one-4-yl, or a 2H-1-benzopyran-2-one-6-yl, each of said groups being optionally substituted by one to 5 substituents selected from the group comprising
hydrogen atom,
halogen atoms,
hydroxy group,
linear or branched $(C_1-C_4)$alkyl groups,
$(C_1-C_4)$ alkoxy groups,
$(C_1-C_4)$ thioalkoxy groups,
trifluoromethyl group,
trifluoromethoxy group,
pentafluorosulfanyl group
acetamide group, —OC(O)C$_6$H$_5$,
formyl group
—COOH,
—COOR with R representing a (C$_1$-C$_4$)alkyl group,
—CH$_2$OH
—CH$_2$OR' with R' representing a (C$_1$-C$_4$)alkyl group,
—CH$_2$OCH$_3$ or a protecting group forming an acetal,
—NH$_2$,
—NR$_2$ with R representing a (C$_1$-C$_4$)alkyl group,
—NO$_2$,
—CN, and

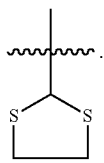

and the pharmaceutically acceptable salts and derivatives thereof for their use for prophylaxis or treatment of trypanosomiasis and leishmaniasis.

In an advantageous embodiment the invention relates to compounds of formula (I) wherein B is a group of formula

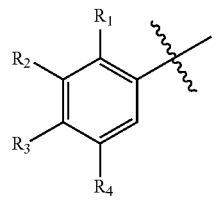

wherein

R$_3$ represents a hydrogen atom, a halogen atom, a trifluoromethyl group, a trifluoromethoxy group, a pentafluorosulfanyl group, a cyano group or a —NHCOCH$_3$ group and R$_1$, R$_2$ and R$_4$ represent each a hydrogen atom for their use for prophylaxis or treatment of trypanosomiasis and leishmaniasis.

In still another advantageous embodiment, the invention relates to compounds of formula (I) wherein B is a group of formula

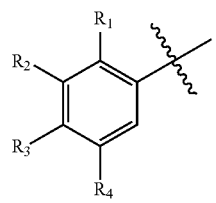

wherein

R$_1$ represents a hydrogen atom, a halogen atom, a trifluoromethyl group, a trifluoromethoxy group, a pentafluorosulfanyl group, a cyano group or a —NHCOCH$_3$ group and R$_2$, R$_3$ and R$_4$ represent each a hydrogen atom, for their use for prophylaxis or treatment of trypanosomiasis and leishmaniasis.

In yet another advantageous embodiment, the invention relates to compounds of formula (I) wherein B is a group of formula

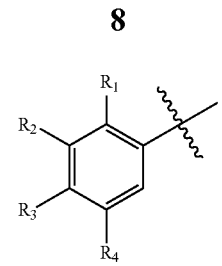

wherein

R$_1$ represents a halogen atom or a methyl group, R$_3$ represents an acetamide group and R$_2$ and R$_4$ represent each a hydrogen atom for their use for prophylaxis or treatment of trypanosomiasis and leishmaniasis.

In yet another advantageous embodiment, the invention relates to compounds of formula (I) wherein B is a group of formula

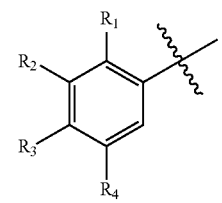

wherein

R$_3$ represents a hydroxy group and R$_4$ represents a halogen atom, a (C$_1$-C$_4$) alkoxy group, a (C$_1$-C$_4$) thioalkoxy group, a trifluoromethyl group, a trifluoromethoxy group or a pentafluorosulfanyl group for their use for prophylaxis or treatment of trypanosomiasis and leishmaniasis.

In another more advantageous embodiment, the invention relates to compounds of formula (I) wherein B is a group of formula

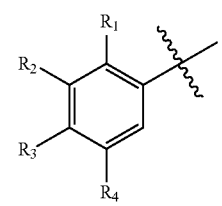

wherein

R$_1$ represents a hydroxy group, a (C$_1$-C$_4$) alkoxy group or a (C$_1$-C$_4$) thioalkoxy group, R$_2$ represents a hydrogen atom or a halogen atom, R$_3$ represents a hydrogen atom, a (C$_1$-C$_4$)alkyl group, a (C$_1$-C$_4$) alkoxy group or a (C$_1$-C$_4$) thioalkoxy group and R$_4$ represents a methoxy group for their use for prophylaxis or treatment of trypanosomiasis and leishmaniasis.

In still another advantageous embodiment, the invention relates to compounds of formula (I) wherein B is a group of formula

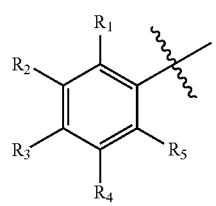

wherein

R₁ represents a hydrogen atom, a-COOH group, a COOR group with R representing a (C₁-C₄)alkyl group, a —CH₂OH group, —CH₂OCH₂OCH₃, group or —CH₂OTHP group, R₂ represents a hydrogen atom, a methyl group or a —NO₂ group, R₃ represents a hydrogen atom, a halogen atom, a —NH₂ group, a —OC(O)C₆H₅ group, a CN group, trifluoromethyl group, trifluoromethoxy group or a

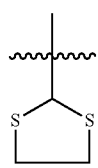

group, R₄ represents a hydrogen atom, a-COOH group, a COOR group with R representing a (C₁-C₄)alkyl group, a —CH₂OH group, —CH₂OCH₂OCH₃, group or —CH₂OTHP group and R₅ represents a hydrogen atom, a methyl group or a —NH₂ group, for their use for prophylaxis or treatment of trypanosomiasis and leishmaniasis.

In another embodiment the invention relates to compounds of formula (I) wherein B is selected from the group comprising:

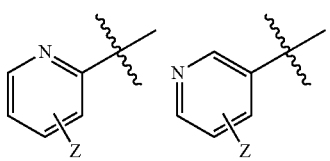

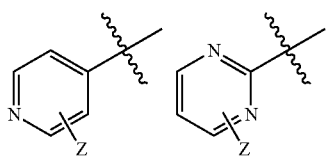

wherein Z represents a hydrogen atom, a fluorine atom or a trifluoromethyl group, for their use for prophylaxis or treatment of trypanosomiasis and leishmaniasis.

In still another advantageous embodiment of the invention, the invention relates to compounds of formula (I) wherein D is a group of formula

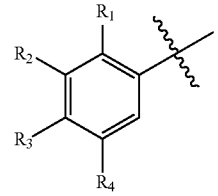

wherein

R₃ represents a hydrogen atom, a methyl group, a trifluoromethyl group, a trifluoromethoxy group, a pentafluorosulfanyl group, and R₁, R₂ and R₄ represent each a hydrogen atom, for their use for prophylaxis or treatment of trypanosomiasis and leishmaniasis.

In still another advantageous embodiment, the invention relates to compounds of formula (I) wherein D is a group of formula

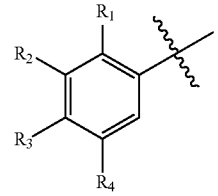

wherein

R₁ represents a hydrogen atom, a methyl group, a trifluoromethyl group, a trifluoromethoxy group, a pentafluorosulfanyl group, and R₂, R₃ and R₄ represent each a hydrogen atom, for their use for prophylaxis or treatment of trypanosomiasis and leishmaniasis.

In yet another advantageous embodiment, the invention relates to compounds of formula (I) wherein D is a group of formula

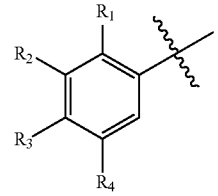

wherein

R₃ represents a hydroxy group, R₄ represents a (C₁-C₄) alkoxy group or a (C₁-C₄) thioalkoxy group and R₁ and R₂ represent each a hydrogen atom for their use for prophylaxis or treatment of trypanosomiasis and leishmaniasis.

In another advantageous embodiment the invention relates to compounds of formula (I) wherein D is selected from the group comprising:

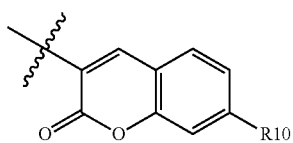

-continued

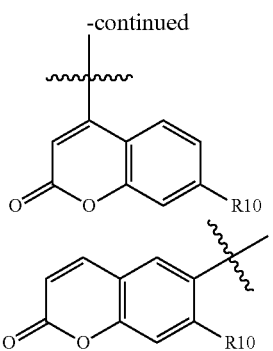

wherein R10 is selected from the group comprising an hydrogen atom, a hydroxyl group and a (C$_1$-C$_4$) alkoxy group, for their use for prophylaxis or treatment of trypanosomiasis and leishmaniasis.

In still another embodiment the invention relates to compounds of formula (I) wherein D is selected from the group comprising:

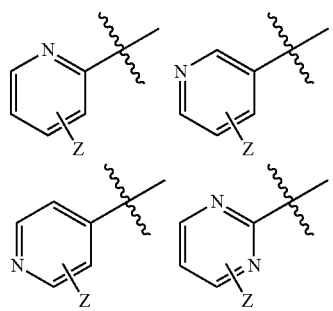

wherein Z represents a hydrogen atom, a fluorine atom or a trifluoromethyl group, for their use for prophylaxis or treatment of trypanosomiasis and leishmaniasis.

In an advantageous embodiment, the invention relates to compounds of formula (I) wherein B and D are identical for their use for prophylaxis or treatment of trypanosomiasis and leishmaniasis.

Some compounds of formula (I) are new and are also part of the invention.

Consequently, the invention still relates to compounds of formula (Ia1)

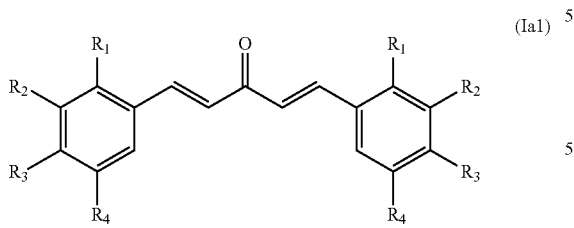

wherein
R$_1$, R$_2$, R$_3$, and R$_4$ each independently of the other represent either a (C$_1$-C$_4$) thioalkoxy group, a trifluoromethoxy group, a pentafluorosulfanyl group, or a —NHCOCH$_3$ group and the pharmaceutically acceptable salts and derivatives thereof.

In an advantageous embodiment the invention relates to compounds of formula (Ia1) wherein one of R$_1$ and R$_3$ represents independently of the other a hydrogen atom, a halogen, a trifluoromethyl group, a trifluoromethoxy group, a pentafluorosulfanyl group, a cyano group or a —NHCOCH$_3$ group and R$_2$ and R$_4$ represent each a hydrogen atom with the proviso that the following compounds are excluded

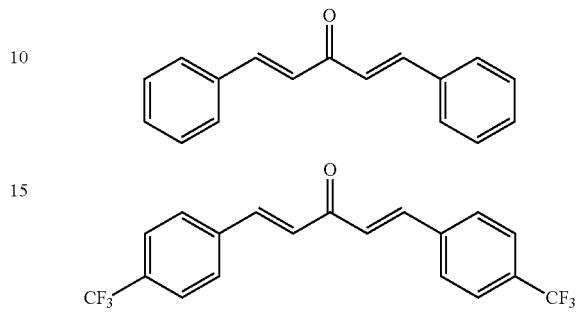

In an other advantageous embodiment the invention relates to compounds of formula (Ia1) wherein R$_3$ represents a hydroxy group and R$_4$ represents a halogen atom, a (C$_1$-C$_4$) alkoxy group, a (C$_1$-C$_4$) thioalkoxy group, a trifluoromethyl group, a trifluoromethoxy group or a pentafluorosulfanyl group with the proviso that the following compound is excluded

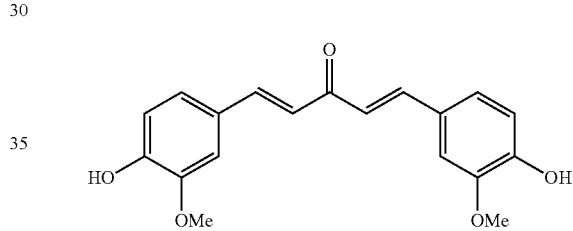

In yet another advantageous embodiment the invention relates to compounds of formula (Ia1) wherein R$_1$ represents a hydroxy group, a (C$_1$-C$_4$) alkoxy group, or a (C$_1$-C$_4$) thioalkoxy group, R$_2$ represents a hydrogen atom or a halogen atom, R$_3$ represents a hydrogen atom a (C$_1$-C$_4$) alkyl group, a (C$_1$-C$_4$) alkoxy group, or a (C$_1$-C$_4$) thioalkoxy group and R$_4$ represents a methoxy group with the proviso that the following compounds are excluded

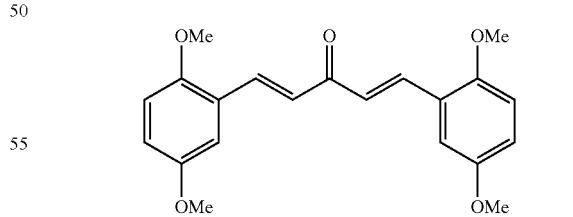

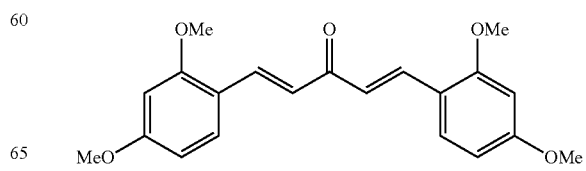

The invention also relates to compounds corresponding to formula (Ia2)

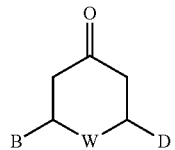
(Ia2)

wherein
W represents N—(C$_1$-C$_4$)alkyl, N—C(O)—(C$_1$-C$_5$)alkylamine or S(O)$_p$ with p=0 to 2,
B and D each independently of each other represent an aryl group or a heteroaryl group optionally substituted by one to 4 substituents selected from the group comprising
hydrogen atom,
halogen atoms,
hydroxy group,
linear or branched (C$_1$-C$_4$)alkyl groups,
(C$_1$-C$_4$) alkoxy groups,
(C$_1$-C$_4$) thioalkoxy groups,
trifluoromethyl group,
trifluoromethoxy group,
pentafluorosulfanyl group
acetamide group,
—OC(O)C$_6$H$_5$,
formyl group
—COOH,
—COOR with R representing a (C$_1$-C$_4$)alkyl group,
—CH$_2$OH
—CH$_2$OR' with R' representing a (C$_1$-C$_4$)alkyl group,
    —CH$_2$OCH$_3$ or a protecting group forming an acetal,
—NH$_2$
—NR$_2$ with R representing a (C$_1$-C$_4$)alkyl group,
—NO$_2$,
—CN, and

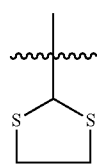

and the pharmaceutically acceptable salts and derivatives thereof
with the proviso that the following compounds are excluded:

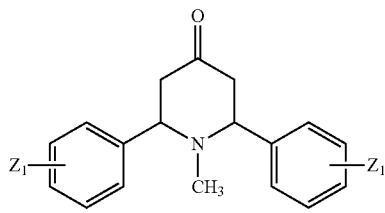

with Z$_1$=H, Cl, F, CF$_3$, OH
with the proviso that when W is NCH$_3$ then B and D cannot be both a phenyl group substituted by methoxy groups or by a methyl group, nor a naphtyl group, with the proviso that when W is SO$_2$ then B and D cannot be both a phenyl group, B and D cannot be both a 3-O$_2$N-phenyl group, and if B is a phenyl group then D cannot be a phenyl group substituted in para by a linear or branched (C$_1$-C$_{25}$)alkyl group, with the proviso that when W is S if B is a phenyl group then D cannot be a phenyl group substituted in para by a linear or branched (C$_1$-C$_{25}$)alkyl group, B and D cannot be both or a pyridinyl group, B and D cannot be both a phenyl group or a phenyl group substituted in para by an halogen atom, and if one of B and D is a phenyl group, then the other cannot be a phenyl group substituted by one or two halogen atoms, with the proviso that when W is SO then B and D cannot be both a phenyl group.

The invention also relates to compounds responding to formula (Ib)

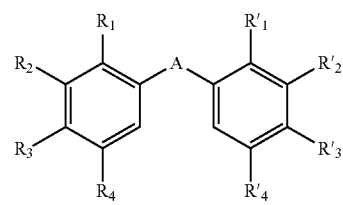
(Ib)

namely compounds of formula (Ib1)

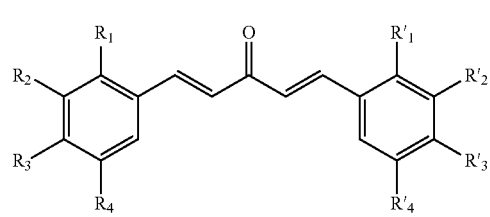
(Ib1)

or of formula (Ib2)

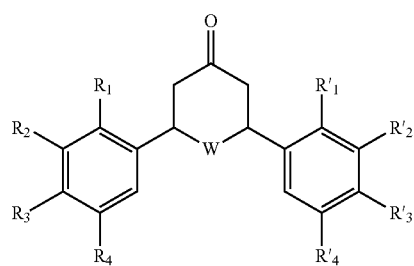
(Ib2)

with W represents N—(C$_1$-C$_4$)alkyl, N—C(O)—(C$_1$-C$_5$) alkylamine or S(O)$_p$ with p=0 to 2, and wherein in said formula (Ib), (Ib1) and (Ib2) R$_1$, R$_2$, R$_3$ and R$_4$ are always respectively different from R'$_1$, R'$_2$, R'$_3$ and R'$_4$, and
if R$_3$ represents either a hydrogen atom, a trifluoromethyl group, a trifluoromethoxy, a pentafluorosulfanyl group, a cyano group or a —NHCOCH$_3$ group, R$_1$, R$_2$ and R$_4$ represent each a hydrogen atom, then R'$_3$ represents a hydrogen atom, a methyl group, a pentafluorosulfanyl group, a dimethylamino group (—N(CH$_3$)$_2$) or a trifluoromethoxy group and R'$_1$, R'$_2$ and R'$_4$ represent each a hydrogen atom, or if $R_3$ represents either a hydrogen atom, a trifluoromethyl group, a trifluoromethoxy group, a pentafluorosulfanyl group, a cyano group or a —NHCOCH$_3$ group, $R_1$, $R_2$ and $R_4$ represent each a hydrogen atom, then $R'_1$ represents a hydrogen atom, a methyl group, a trifluoromethoxy group or a pentafluorosulfanyl group and $R'_2$, $R'_3$, and $R'_4$ represent each a hydrogen atom, or if $R_3$ represents either a hydrogen atom, a trifluoromethyl group, a trifluoromethoxy group, a pentafluorosulfanyl group, a cyano group or a —NHCOCH$_3$ group, $R_1$, $R_2$ and $R_4$ represent each a hydrogen atom, then $R'_3$ represents a hydroxy group, $R'_4$ represents a ($C_1$-$C_4$) alkoxy group or a ($C_1$-$C_4$) thioalkoxy group and $R'_1$ and $R'_2$ represent each a hydrogen atom, if $R_1$ represents either a hydrogen atom, a trifluoromethyl group, a trifluoromethoxy group, a pentafluorosulfanyl group, a cyano group or a —NHCOCH$_3$ group, $R_2$, $R_3$ and $R_4$ represent each a hydrogen atom, then $R'_3$ represents a hydrogen atom, a methyl group, a trifluoromethoxy group or a pentafluorosulfanyl group and $R'_1$, $R'_2$ and $R'_4$ represent each a hydrogen atom, or if $R_1$ represents either a hydrogen atom, a trifluoromethyl group, a trifluoromethoxy group, a pentafluorosulfanyl group, a cyano group or a —NHCOCH$_3$ group, $R_2$, $R_3$ and $R_4$ represent each a hydrogen atom, then $R'_1$ represents a hydrogen atom, a methyl group, a trifluoromethoxy group or a pentafluorosulfanyl group and $R'_2$, $R'_3$, and $R'_4$ represent each a hydrogen atom, or if $R_1$ represents either a hydrogen atom, a trifluoromethyl group, a trifluoromethoxy group, a pentafluorosulfanyl group, a cyano group or a —NHCOCH$_3$ group, $R_1$, $R_2$ and $R_4$ represent each a hydrogen atom, then $R'_3$ represents a hydroxy group, $R'_4$ represents a ($C_1$-$C_4$) alkoxy group or a ($C_1$-$C_4$) thioalkoxy group and $R'_1$ and $R'_2$ represent each a hydrogen atom, if $R_3$ represents a hydroxy group, $R_4$ represents a halogen atom, a ($C_1$-$C_4$) alkoxy group, a ($C_1$-$C_4$) thioalkoxy group, a trifluoromethyl group, a trifluoromethoxy group or a pentafluorosulfanyl group and $R_1$ et $R_2$ represent each a hydrogen atom, then $R'_3$ represents a hydrogen atom, a methyl group or a trifluoromethoxy group or a pentafluorosulfanyl group and $R'_1$, $R'_2$ and $R'_4$ represent each a hydrogen atom, if $R_3$ represents a hydroxy group, $R_4$ represents a halogen atom, a ($C_1$-$C_4$) alkoxy group, a ($C_1$-$C_4$) thioalkoxy group, a trifluoromethyl group or a trifluoromethoxy group or a pentafluorosulfanyl group and $R_1$ and $R_2$ represent each a hydrogen atom, then $R'_1$ represents a hydrogen atom, a methyl group, a trifluoromethoxy group or a pentafluorosulfanyl group and $R'_2$, $R'_3$, and $R'_4$ represent each a hydrogen atom, or if $R_3$ represents a hydroxy group, $R_4$ represents a halogen atom, a ($C_1$-$C_4$) alkoxy group, a ($C_1$-$C_4$) thioalkoxy group, a trifluoromethyl group, a trifluoromethoxy group or a pentafluorosulfanyl group and $R_1$ and $R_2$ represent each a hydrogen atom, then $R'_3$ represents a hydroxy group, $R'_4$ represents a ($C_1$-$C_4$) alkoxy group or a ($C_1$-$C_4$) thioalkoxy group and $R'_1$ and $R'_2$ represent each a hydrogen atom, if $R_1$ represents a hydroxy group or a ($C_1$-$C_4$) alkoxy group or a ($C_1$-$C_4$) thioalkoxy group, $R_2$ represents a hydrogen atom or a halogen atom, $R_3$ represents a hydrogen atom and $R_4$ represents a methoxy group, then $R'_3$ represents a hydrogen atom, a methyl group, a trifluoromethoxy group or a pentafluorosulfanyl group and $R'_1$, $R'_2$ and $R'_4$ represent each a hydrogen atom, or if $R_1$ represents a hydroxy group, a ($C_1$-$C_4$) alkoxy group or a ($C_1$-$C_4$) thioalkoxy group, $R_2$ represents a hydrogen atom or a halogen atom, $R_3$ represents a hydrogen atom and $R_4$ represents a methoxy group, then $R'_1$ represents a hydrogen atom, a methyl group, a trifluoromethoxy group or a pentafluorosulfanyl group and $R'_2$, $R'_3$, and $R'_4$ represent each a hydrogen atom, or if $R_1$ represents a hydroxy group, a ($C_1$-$C_4$) alkoxy group or a ($C_1$-$C_4$) thioalkoxy group, $R_2$ represents a hydrogen atom or a halogen atom, $R_3$ represents a hydrogen atom and $R_4$ represents a methoxy group, then $R'_3$ represents a hydroxy group, $R'_4$ represents a ($C_1$-$C_4$) alkoxy group or a ($C_1$-$C_4$) thioalkoxy group and $R'_1$, and $R'_2$ represent each a hydrogen atom.

The invention also relates to compounds responding to formula (Ic)

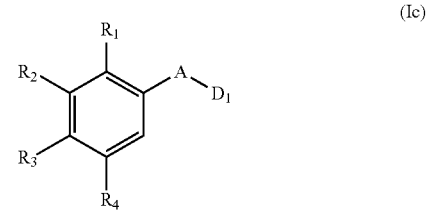

namely compounds of formula (Ic1)

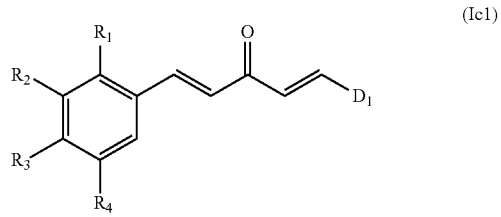

or of formula (Ic2)

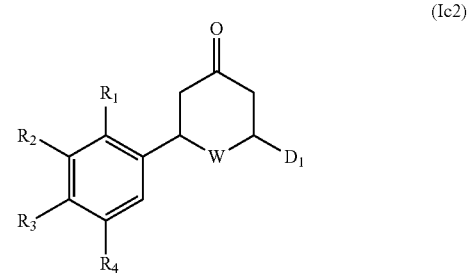

with W represents N—($C_1$-$C_4$)alkyl, N—C(O)—($C_1$-$C_5$) alkylamine or S(O)$_p$ with p=0 to 2 and wherein in said formula (Ic), (Ic1) and (Ic2) $D_1$ is selected from groups A) or B), namely:

A)

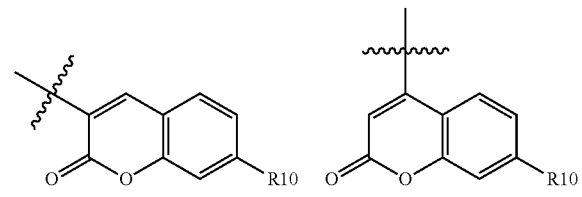

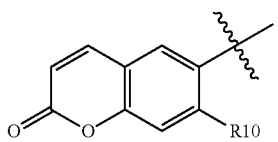

wherein $R^{10}$ is selected from the group comprising an hydrogen atom, a hydroxyl group and a ($C_1$-$C_4$) alkoxy group.

B)

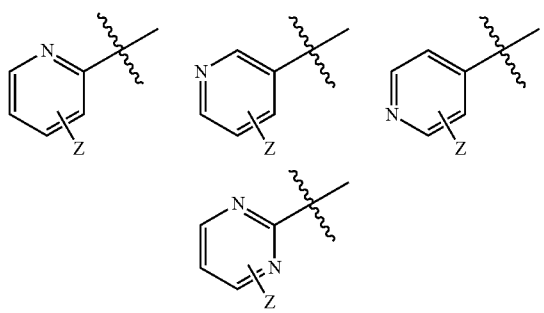

wherein Z represents a hydrogen atom, a fluorine atom or a trifluoromethyl group, and either $R_3$ represents a hydrogen atom, a trifluoromethyl group, a trifluoromethoxy group, a pentafluorosulfanyl group, a cyano group or a —NHCOCH$_3$ group and $R_1$, $R_2$ and $R_4$ represent each a hydrogen atom, or either $R_1$ represents a hydrogen atom, a trifluoromethyl group, a trifluoromethoxy group, a pentafluorosulfanyl group, a cyano group or a —NHCOCH$_3$ group and $R_2$, $R_3$ and $R_4$ represent each a hydrogen atom, either $R_3$ represents a hydroxy group, $R_4$ represents a halogen atom, a ($C_1$-$C_4$) alkoxy group, a ($C_1$-$C_4$) thioalkoxy, a trifluoromethyl group or a trifluoromethoxy group or a pentafluorosulfanyl group and $R_1$ and $R_2$ represent each a hydrogen atom, or either $R_1$ represents an hydroxy group or a ($C_1$-$C_4$) alkoxy group or a ($C_1$-$C_4$) thioalkoxy group, $R_2$ represents a hydrogen atom or a halogen atom, $R_3$ represents a hydrogen atom and $R_4$ represents a methoxy group.

The invention also relates to compounds responding to formula (Id)

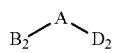

namely compounds of formula (Id1)

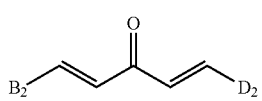

or of formula (Id2)

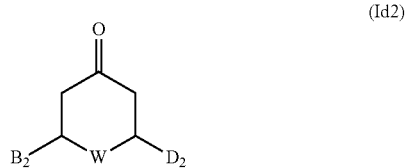

with W represents N—($C_1$-$C_4$)alkyl, N—C(O)—($C_1$-$C_5$) alkylamine or S(O)$_p$ with p=0 to 2 and wherein in said formula (Id), (Id1) and (Id2), $B_2$ and $D_2$ are selected independently from each other from the group comprising:

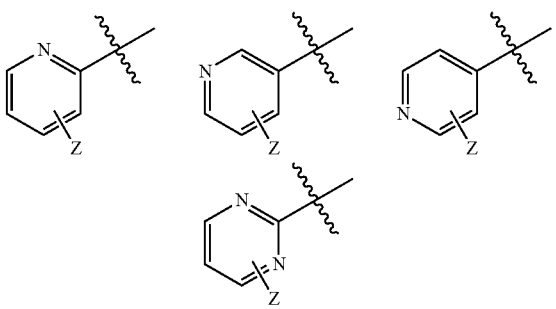

with the proviso that when W is S then $B_2$ and $D_2$ cannot be both a pyridinyl group.

The compounds of formula (Ia2), (Ib2), (Ic2) and (Id2) are respectively prodrugs of compounds of formula (Ia1), (Ib1), (Ic1) and (Id1) i.e. although they are not active per se in vitro, after administration to a patient or to cells, compounds of formula (Ia2), (Ib2), (Ic2) and (Id2) are respectively metabolised in vivo into the corresponding compounds of formula (Ia1), (Ib1), (Ic1) and (Id1).

The symmetrical dibenzylidene acetones of formula (Ia) used according to the invention may be prepared by any methods known from the one skilled in the art, in particular through classical base-catalyzed Claisen-Schmidt reaction. They may be prepared for instance as disclosed in the examples.

The symmetrical and asymmetrical 2,6-diaryl-4-piperidones and 2,6-diheteroaryl-4-piperidones of the most potent dibenzylidene acetones were prepared via (i) a Horner-Wadsworth-Emmons reaction followed by a Claisen-Schmidt reaction, or Claisen-Schmidt reactions under various reaction conditions depending on the substitution pattern of the aromatic ring of the starting aldehydes, and then (ii) the Michael addition with methylamine. They may be prepared for instance as disclosed in the examples.

The invention relates to compounds (Ia1), (Ia2), (Ib), (Ib1), (Ib2), (Ic), (Ic1), (Ic2), (Id), (Id1), and (Id2), as defined above, as drug, with the proviso that the following compounds are excluded:

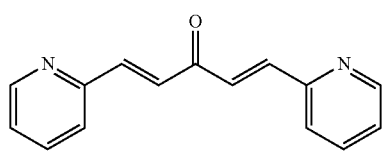

-continued
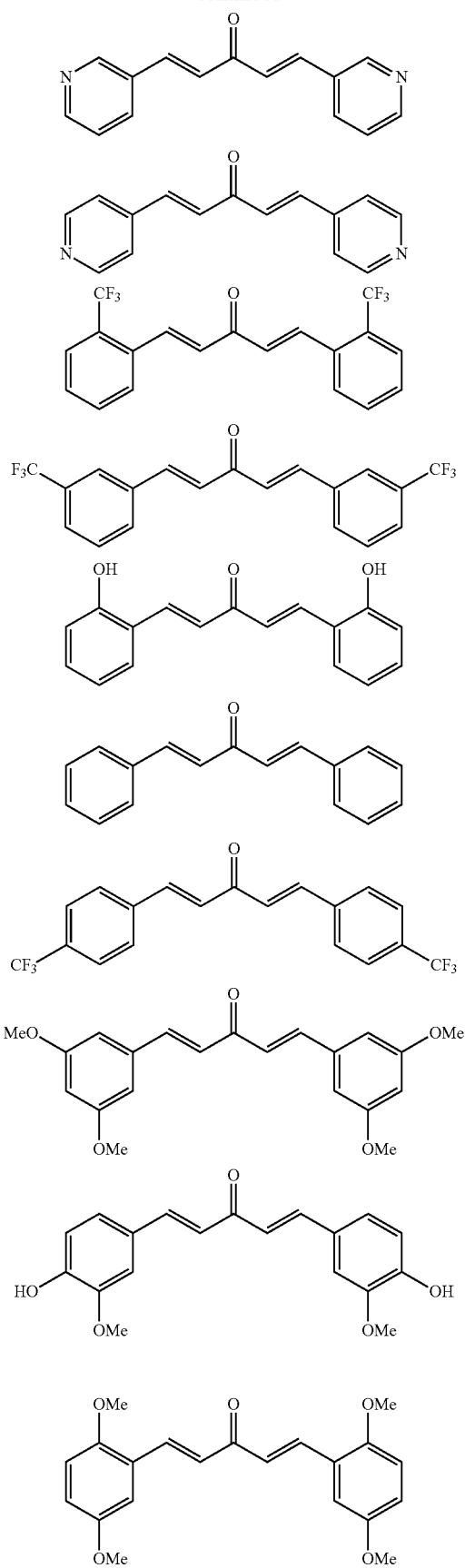
-continued
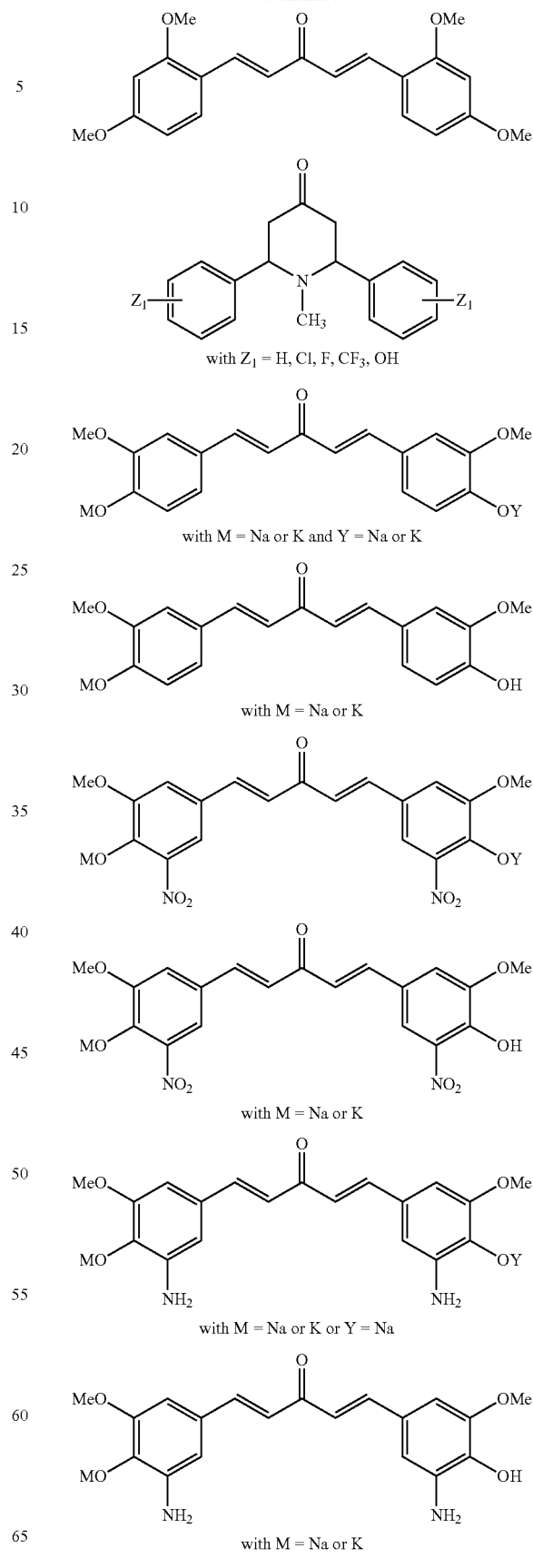
with $Z_1$ = H, Cl, F, $CF_3$, OH
with M = Na or K and Y = Na or K
with M = Na or K
with M = Na or K
with M = Na or K or Y = Na
with M = Na or K -continued

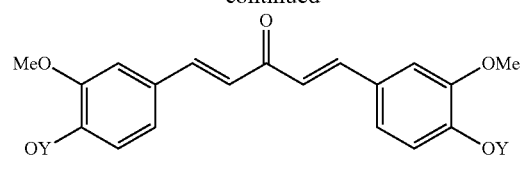
with Y = COC₆H₅

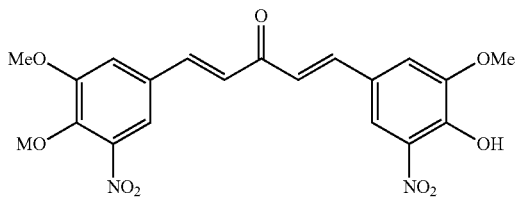

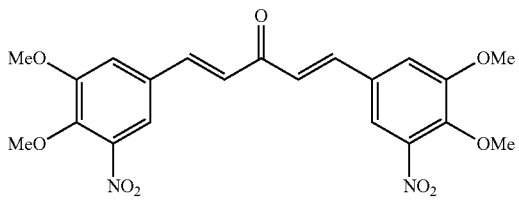

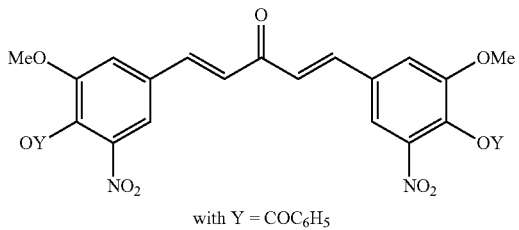
with Y = COC₆H₅

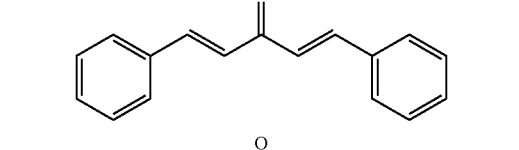

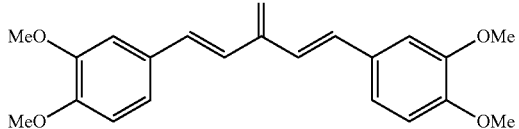

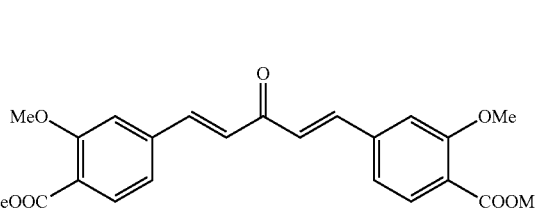

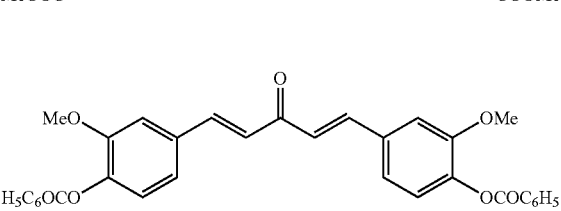

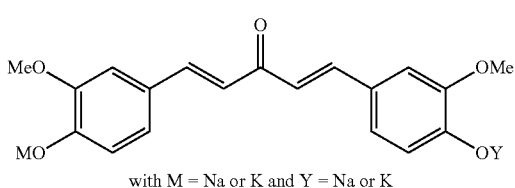
with M = Na or K and Y = Na or K

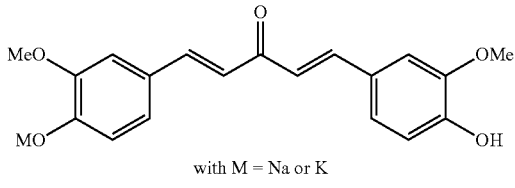
with M = Na or K

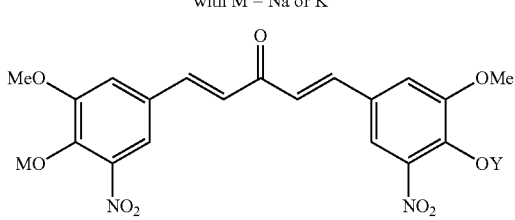
with M = Na or K and Y = Na

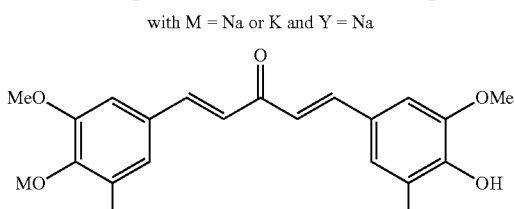
with M = Na or K

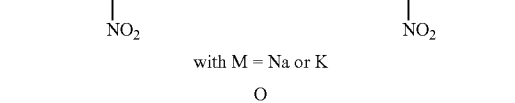

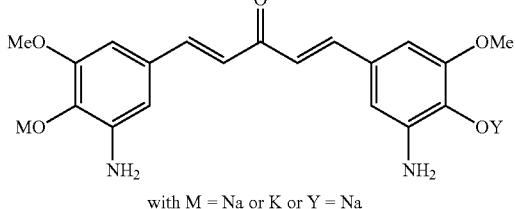
with M = Na or K or Y = Na

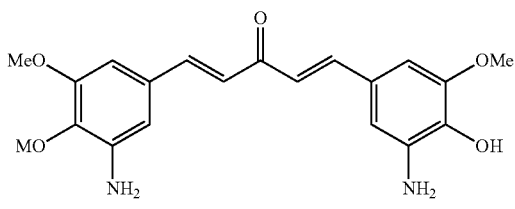
with M = Na or K

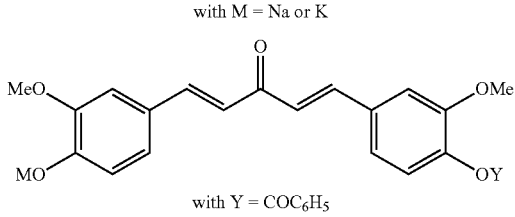
with Y = COC₆H₅

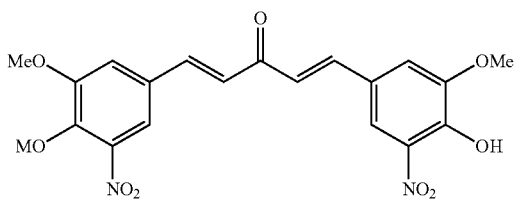

The invention relates to compounds (Ia1), (Ia2), (Ib), (Ib1), (Ib2), (Ic), (Ic1), (Ic2), (Id), (Id1), and (Id2), as defined above, for their specific use for the therapy or the prophylaxis as antikinetoplastid agents, with the proviso that the following compounds are excluded:

-continued
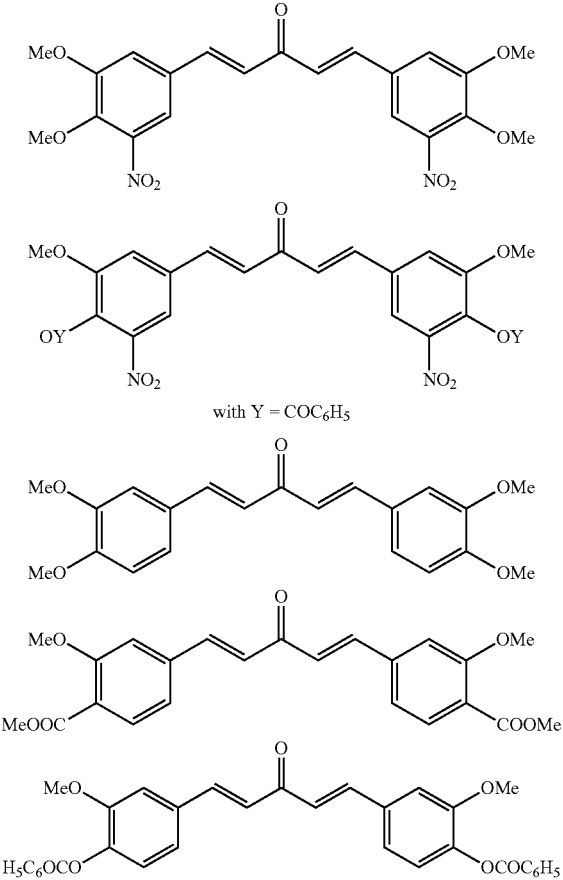
The invention also relates to pharmaceutical compositions comprising as active ingredient one or more of the compounds of formulas (Ia1), (Ia2), (Ib), (Ib1), (Ib2), (Ic), (Ic1), (Ic2), (Id), (Id1), and (Id2) as defined above, in combination with excipients and/or pharmaceutically acceptable diluents or carriers with the proviso that compounds of formula
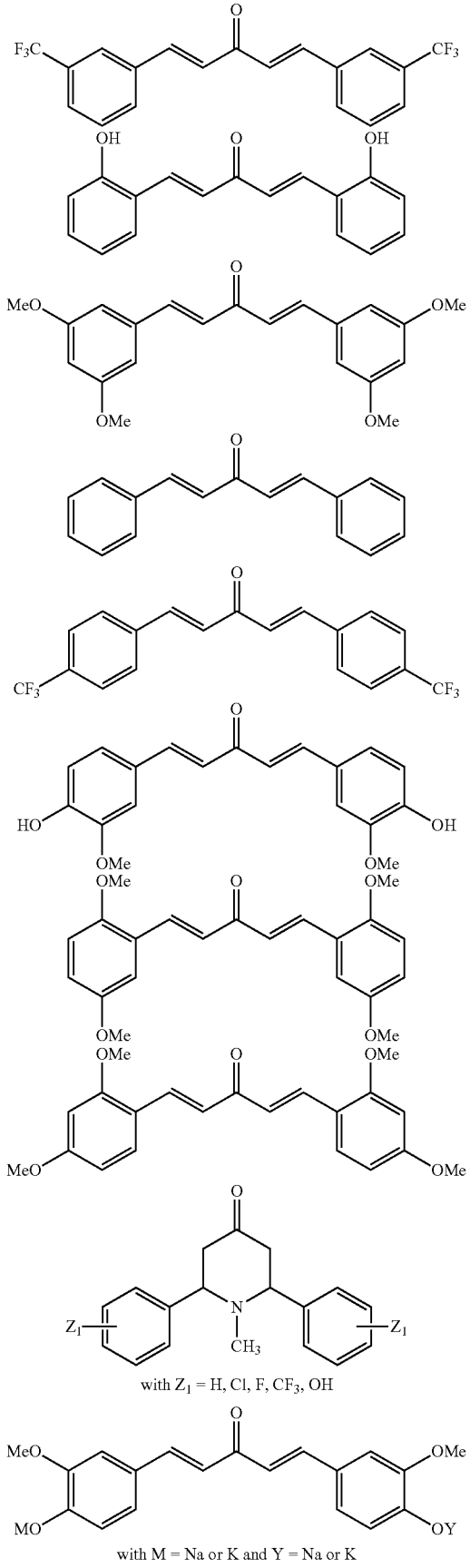

-continued

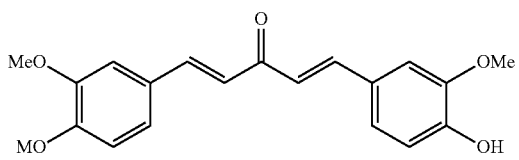
with M = Na or K

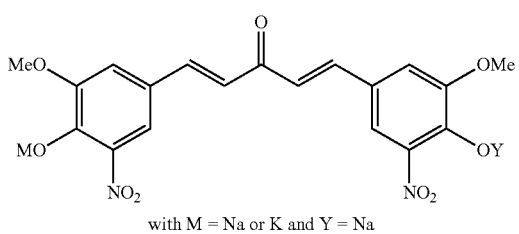
with M = Na or K and Y = Na

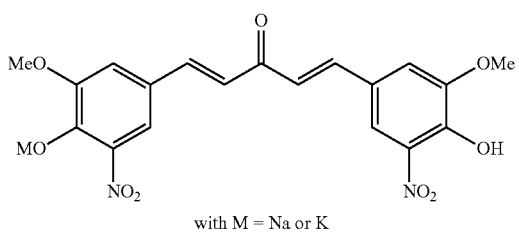
with M = Na or K

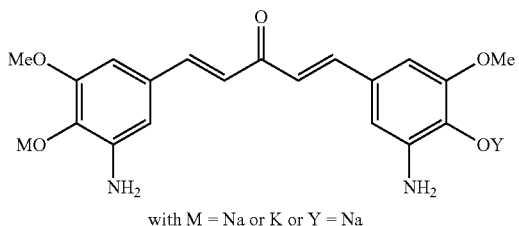
with M = Na or K or Y = Na

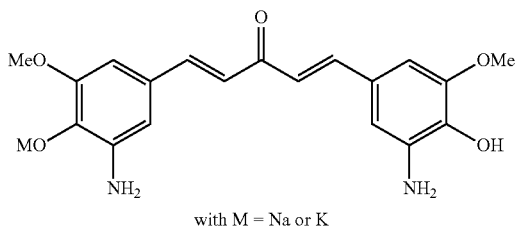
with M = Na or K

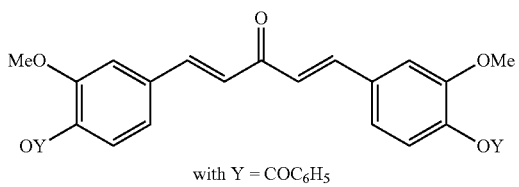
with Y = COC$_6$H$_5$

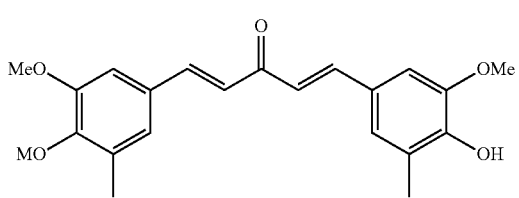

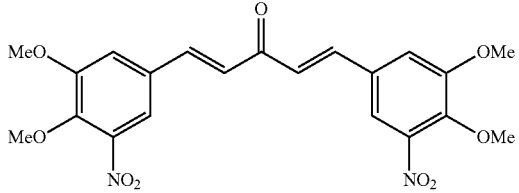

-continued

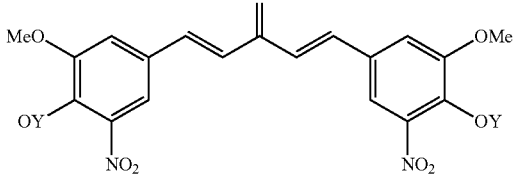
with Y = COC$_6$H$_5$

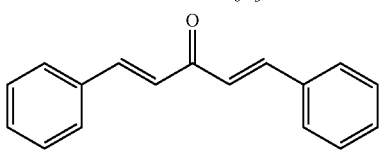

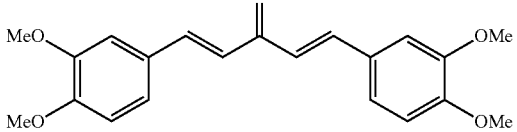

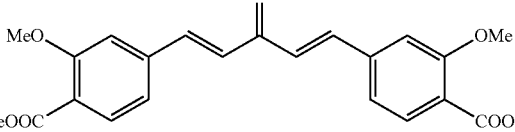

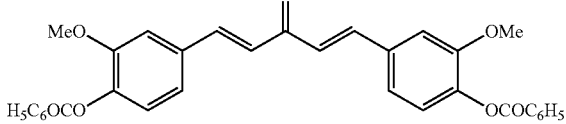

are excluded when they are the only active ingredient in the composition.

According to the invention, the compounds of formula (I) may be used in association with one to three other antikinetoplastidal agents for a simultaneous, separated or sequential administration. Thus the pharmaceutical compositions according to the invention may further comprise as active ingredient one to three other antikinetoplastidal agents selected from the group comprising melarsoprol, eflornithine, pentamidine, suramin, miltefosine, amphotericin B, nifurtimox, benznidazole, pafuramidine, meglumine antimoniate, sodium stibogluconate, paromomycin, diminazene, allopurinol, aminosidine, sitamaquine, fungicidal azoles used as sterol biosynthesis inhibitors, inhibitors of S-adenosylmethionine decarboxylase as 5'-deoxy-5'-(hydroxyethyl)thioadenosine (HETA) type, plumbagin for a simultaneous, separated or sequential administration.

The invention also relates to a method of treating infection caused by a kinetoplastidae parasite, comprising administering to a mammal in need thereof an effective amount of at least one compound selected from the group comprising the compounds having one the formula (I), (Ia1), (Ia2), (Ib) (Ib1), (Ib2), I(c), (Ic1), (Ic2), (Id), (Id1) or (Id2).

The invention further relates to the use of at least one compound selected from the group comprising the compounds having one the formula (I) (Ia1), (Ia2), (Ib) (Ib1), (Ib2), I(c), (Ic1), (Ic2), (Id), (Id1) or (Id2) for the preparation of a drug useful as antikinetoplastidal agent.

BRIEF DESCRIPTIONS OF THE DRAWINGS

FIGS. 1 and 2 include Tables 1 and 2, respectively, which show the biological activity against the parasites of the symmetrical dibenzylidene acetone intermediates needed for preparing the 4-piperidones.

FIG. 3 includes Table 3, which shows the biological activity against the parasites of the asymmetrical dibenzylidene acetone intermediates.

FIG. 4 includes Table 4, which shows the biological activity against the parasites of the symmetrical conjugated symmetrical dibenzylidene acetone and the diheteroarylidene acetone intermediates needed for preparing the 4-piperidones.

FIG. 5 includes Table 5, which shows the biological activity against the parasites of the symmetrical 2,6-diaryl-4-piperidones and 2,6-diheteroaryl-4-piperidones.

FIG. 6 includes Table 6, which shows the biological activity against the parasites of the symmetrical 2,6-diaryl-4-piperidones and 2,6-diheteroaryl-4-piperidones in repeated bioassays, in comparison with known drugs from the market.

FIG. 7 includes Table 7, which shows the biological activity against the parasites of the symmetrical 2,6-diaryl-4-piperidones and 2,6-diheteroaryl-4-piperidones in repeated bioassays, in comparison with known drugs from the market.

DETAILED DESCRIPTION OF THE INVENTION

The following examples 1 to 9 and tables 1 to 7 illustrate the invention. In all tables (1-7), the results are expressed as $IC_{50}$ values in μM. Toxicity is also indicated if present.

The biological activities against the parasites of:
- the symmetrical dibenzylidene acetone intermediates, according to example 1, needed for preparing the 4-piperidones are shown in Tables 1 to 2, and Tables 4 to 5
- the asymmetrical dibenzylidene acetone intermediates, according to example 3, are shown in Table 3,
- the symmetrical conjugated symmetrical dibenzylidene acetone is given in Table 2,
- the diheteroarylidene acetone intermediates, according to example 2, needed for preparing the 4-piperidones and 4-thiopyranones (and S-oxidized metabolites) are shown in Table 4,
- the symmetrical 2,6-diheteroaryl-4-piperidones and 2,6-diaryl-4-piperidones, according to example 5, are shown in Tables 5 and 6,
- the symmetrical 2,6-diheteroaryl-4-thiopyranones and 2,6-diaryl-4-thiopyranones, according to example 6, are shown in Tables 5 and 7, respectively, along with some selected parent dibenzylidene acetone intermediates, in repeated bioassays, in comparison with known reference drugs from the market, are shown in Tables 6 and 7.

EXAMPLE 1

Symmetrical Dibenzylidene Acetones

The symmetrical dibenzylidene acetones were prepared via a classical base-catalyzed Claisen-Schmidt reaction with 2 equivalents of the aldehyde and 1 equivalent of acetone; the reaction was performed in an organic solvent like ethanol in presence of a base like NaOH or $K_2CO_3$ depending on the substituents at the aromatic ring of the starting aldehyde as illustrated in Scheme 1.

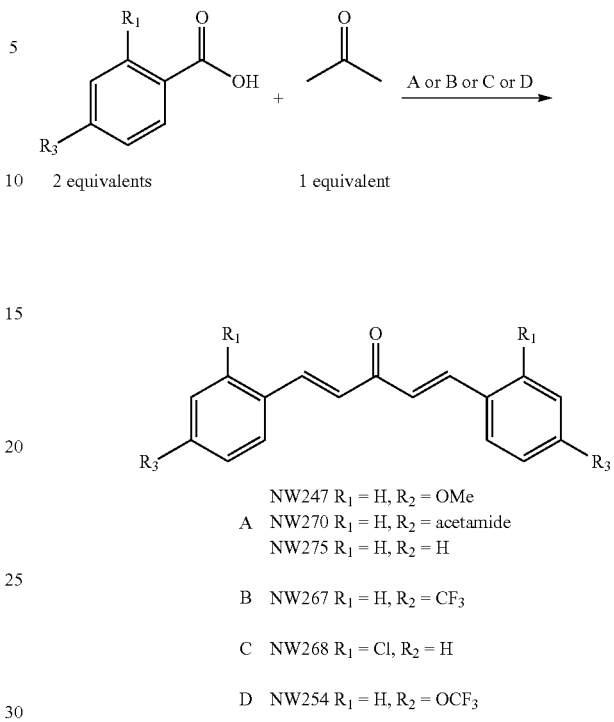

Scheme 1: Synthesis of symmetrical dibenzylidene acetones.

A  NW247 $R_1$ = H, $R_2$ = OMe
   NW270 $R_1$ = H, $R_2$ = acetamide
   NW275 $R_1$ = H, $R_2$ = H

B  NW267 $R_1$ = H, $R_2$ = $CF_3$

C  NW268 $R_1$ = Cl, $R_2$ = H

D  NW254 $R_1$ = H, $R_2$ = $OCF_3$

Reagents and conditions: (A) NaOH (2N), EtOH, 4 h, RT; (B) $K_2CO_3$, aq. EtOH (45%), 24 h, RT; (C) 4 equiv. aq. NaOH, EtOH; (D) cat. aq. NaOH (10%), EtOH, 1 h, RT.

Some symmetrical dibenzylidene acetones were prepared via a classical base-catalyzed Claisen-Schmidt reaction with 2 equivalents of the aldehyde and 1 equivalent of acetone; the reaction was performed in an organic solvent like ethanol in presence of NaOH, or in triethylamine in presence of lithium perchlorate or in acidic medium or $K_2CO_3$ depending on the substituents at the aromatic ring of the starting aldehyde as illustrated in Scheme 2.

Scheme 2: Synthesis of symmetrical dibenzylidene acetones.

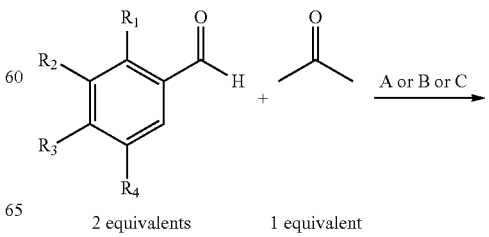

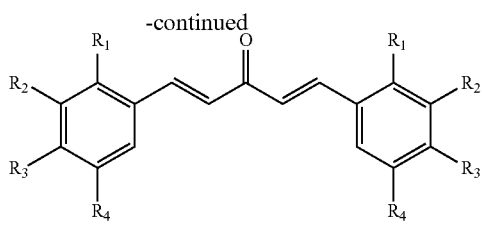

| | | |
|---|---|---|
| A | NW307.2 $R_1 = R_2 = R_4 = H$, $R_3 = CN$ | |
| | NW308 $R_1 = R_2 = R_4 = H$, $R_3 = Cl$ | |
| | | |
| | NW300 $R_1 = R_4 = H$, $R_2 = OMe$, $R_3 = OH$ | |
| B | NW310.1 $R_1 = R_4 = H$, $R_2 = CF_3$, $R_3 = OH$ | |
| | NW317 $R_1 = R_4 = H$, $R_2 = OCF_3$, $R_3 = OH$ | |
| | | |
| | NW324.2 $R_1 = R_4 = OMe$, $R_2 = Br$, $R_3 = H$ | |
| C | NW326.4 $R_1 = OH$, $R_2 = Br$, $R_3 = H$, $R_4 = OMe$ | |
| | NW327.2 $R_1 = OH$, $R_2 = R_3 = H$, $R_4 = OMe$ | |
| | NW333.1 $R_1 = R_4 = OMe$, $R_2 = R_3 = H$ | |

The detailed synthesis of the said compounds is disclosed hereunder.

(1E,4E)-1,5-Bis(4-methoxy-phenyl)-penta-1,4-dien-3-one (NW247)

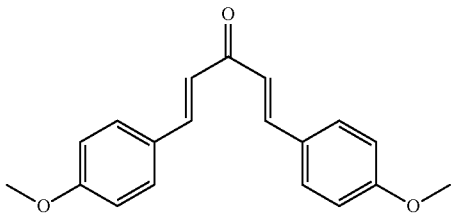

To a solution of NaOH (3.6 g, 92 mmol) in H$_2$O (36 mL) and EtOH (29 mL) were added 4-methoxybenzaldehyde (4.5 mL, 37 mmol) and acetone (1.3 mL, 18 mmol). The reaction mixture was stirred for 1 h at ambient temperature and the colorless solution turned into a yellow suspension. The precipitate was filtered, washed with Et$_2$O, recrystallized from EtOAc and dried in vacuo to obtain NW247 as a pale yellow solid (4.3 g, 82%). mp: 127-128° C. $^1$H NMR (300 MHz, CDCl$_3$) δ (ppm): 7.68 (d, $^3$J=15.9 Hz, 2H, H$_{vin}$), 7.54 (d, $^3$J=8.8 Hz, 4H, H$_{Ar}$), 6.93 (d, $^3$J=15.9 Hz, 2H, H$_{vin}$), 6.91 (d, $^3$J=8.8 Hz, 4H, H$_{Ar}$), 3.82 (s, 6H, CH$_3$). $^{13}$C NMR (75 MHz, CDCl$_3$) δ (ppm): 188.8 (C), 161.5 (C), 142.6 (CH), 130.0 (CH), 127.6 (C), 123.5 (CH), 114.4 (CH), 55.4 (CH$_3$). MS (FAB) m/z: 295.2 (M+). Anal. calcd for C$_{19}$H$_{18}$O$_3$: C, 77.53; H, 6.16. Found: C, 77.45; H, 6.18%.

N-{4-[(1E,4E)-5-(4-Acetylamino-phenyl)-3-oxo-penta-1,4-dienyl]-phenyl}-acetamide (NW270)

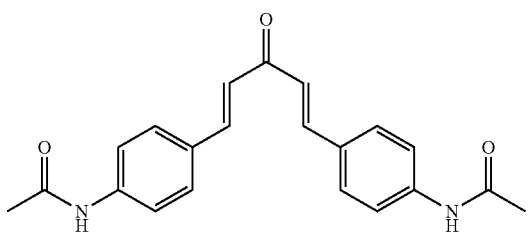 [SMILES: CC(=O)Nc1ccc(/C=C/C(=O)/C=C/c2ccc(NC(C)=O)cc2)cc1]

A mixture of p-acetamidobenzaldehyde (8.15 g, 50 mmol) dissolved in 200 mL of hot EtOH) and acetone (1.8 mL, 25 mmol) was added dropwise to a solution of aq. NaOH solution (2 N, 25 mL) in EtOH (150 mL). The reaction mixture was stirred for 4 h at ambient temperature and the resulting orange precipitate was filtered, washed with water and dried in vacuo to afford NW270 as a bright yellow solid (4.6 g, 53%). mp: 253-255° C. $^1$H NMR (250 MHz, DMSO-d$_6$) δ (ppm): 10.18 (s, 2H, NH), 7.81-7.58 (m, 10H, H$_{Ar}$, H$_{vin}$), 7.22 (d, $^3$J=16.0 Hz, 2H, H$_{vin}$), 2.08 (s, 6H, CH$_3$). $^{13}$C NMR (75 MHz, DMSO-d$_6$) δ (ppm): 188.2 (C), 168.6 (C), 142.1 (CH), 141.4 (C), 129.4 (CH), 124.1 (CH), 118.9 (CH), 24.1 (CH$_3$). MS (EI) m/z: 348.2 (M+). Anal. calcd for C$_{21}$H$_{20}$N$_2$O$_3$: C, 72.40; H, 5.79; N, 8.04. Found: C, 72.14; H, 5.78; N, 7.97%.

(1E,4E)-1,5-Diphenyl-penta-1,4-dien-3-one (NW275)

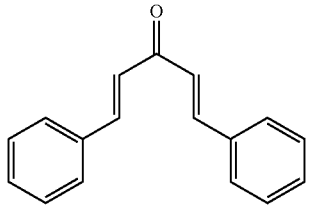 [SMILES: O=C(/C=C/c1ccccc1)/C=C/c1ccccc1]

A solution of aq. NaOH solution (2 N, 125 mL) in EtOH (250 mL) was added to a mixture of benzaldehyde (26.5 g, 25 mmol) in acetone (9.2 mL, 13 mmol). The reaction mixture was stirred for 4 h at ambient temperature and the resulting yellow precipitate was filtered, washed with H$_2$O, recrystallized from EtOAc and dried in vacuo to obtain NW275 as a yellow solid (23.1 g, 79%). mp: 106-107° C. $^1$H NMR (250 MHz, CDCl$_3$) δ (ppm): 7.78 (d, $^3$J=16.0 Hz, 2H, H$_{vin}$), 7.66-7.64 (m, 4H, H$_{Ar}$), 7.46-7.44 (m, 6H, H$_{Ar}$), 7.12 (d, $^3$J=16.0 Hz, 2H, H$_{vin}$). $^{13}$C NMR (75 MHz, CDCl$_3$) δ (ppm): 189.3 (C), 143.7 (CH), 135.2 (C), 130.9 (CH), 129.4 (CH), 128.8 (CH), 125.8 (CH). MS (EI) m/z: 234.2 (M+). Anal. calcd for C$_{17}$H$_{14}$O: C, 87.15; H, 6.02. Found: C, 87.03; H, 6.03%.

(1E,4E)-1,5-Bis(4-trifluoromethyl-phenyl)-penta-1,4-dien-3-one (NW267)

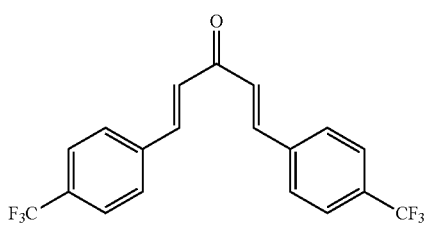 [SMILES: O=C(/C=C/c1ccc(C(F)(F)F)cc1)/C=C/c1ccc(C(F)(F)F)cc1]

A mixture of α,α,α-trifluoro-p-tolualdehyde (3.08 mL, 23 mmol) in acetone (0.84 mL, 11 mmol) was added to a solution of K$_2$CO$_3$ (3.2 g, 23 mmol) in aq. 45% EtOH solution (44 mL). After 10-15 min the colorless solution turned yellow. The reaction mixture was stirred for 2 h at ambient temperature and the resulting precipitate was filtered, recrystallized from EtOAc and dried in vacuo to obtain NW267 as a pale yellow solid (1.87 g, 43%). mp: 148-150° C. $^1$H NMR (250 MHz, CDCl$_3$) δ (ppm): 7.86-7.56 (m, 10H, H$_{vin}$, H$_{Ar}$), 7.15

(d, $^3J$=16.0 Hz, 2H, H$_{vin}$). $^{13}$C NMR (75 MHz, CDCl$_3$) δ (ppm): 188.1 (C), 141.9 (CH), 132.1 (q, $^2J$(C,F)=32.7 Hz, C), 128.5 (CH), 127.2 (CH), 126.0 (q, $^3J$(C,F)=3.8 Hz, CH). MS (FAB) m/z: 371.2 (M+). Anal. calcd for C$_{19}$H$_{12}$F$_6$O: C, 61.63; H, 3.27. Found: C, 61.49; H, 3.39%.

(1E,4E)-1,5-Bis(2-chloro-phenyl)-penta-1,4-dien-3-one (NW268)

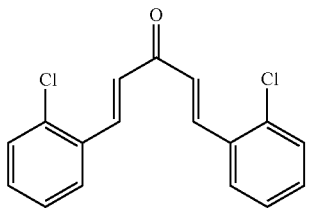 [SMILES: O=C(/C=C/c1ccccc1Cl)/C=C/c1ccccc1Cl]

A solution of NaOH (1.4 g, 142 mmol) in H$_2$O (60 mL) and EtOH (60 mL) was added to a mixture of 2-chlorobenzaldehyde (8 mL, 72 mmol) in acetone (2.6 mL, 36 mmol). The reaction mixture was stirred for 1d at room temperature and the resulting precipitate was filtered, washed with H$_2$O, recrystallized from EtOAc and dried in vacuo to obtain NW268 as a bright yellow solid (7.4 g, 69%). mp: 107-109° C. $^1$H NMR (250 MHz, CDCl$_3$) δ (ppm): 8.15 (d, $^3J$=16.0 Hz, 2H, H$_{vin}$), 7.79-7.66 (m, 2H, H$_{Ar}$), 7.51-7.29 (m, 6H, H$_{Ar}$), 7.08 (d, $^3J$=16.0 Hz, 2H, H$_{vin}$). $^{13}$C NMR (75 MHz, CDCl$_3$) δ (ppm): 188.7 (C), 139.3 (CH), 135.4 (C), 133.0 (C), 131.2 (CH), 130.2 (CH), 127.7 (CH), 127.5 (CH), 127.1 (CH). MS (FAB) m/z: 303.1 (M+). Anal. calcd for C$_{17}$H$_{12}$Cl$_2$O: C, 67.35; H, 3.99; Cl, 23.39. Found: C, 67.09; H, 4.06; Cl, 22.65%.

(1E,4E)-1,5-Bis(4-trifluoromethoxy-phenyl)-penta-1,4-dien-3-one (NW254)

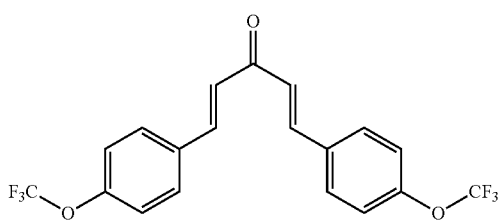

A colorless solution of 4-(trifluoromethoxy)-benzaldehyde (0.75 mL, 5.3 mmol) in acetone (0.19 mL, 2.6 mmol), EtOH (5 mL) and H$_2$O (1 mL) was treated with aq. 10% NaOH solution (~12 drops). The reaction mixture was stirred for 2 h at room temperature and the colorless solution turned into a yellow suspension. The precipitate was filtered, washed with H$_2$O and dried in vacuo to obtain NW254 as a pale yellow solid (275 mg, 25%). mp: 112-115° C. $^1$H NMR (250 MHz, CDCl$_3$) δ (ppm): 7.74 (d, $^3J$=16.1 Hz, 2H, H$_{vin}$), 7.67 (d, $^3J$=8.5 Hz, 4H, H$_{Ar}$), 7.28 (d, $^3J$=8.2 Hz, 4H, H$_{Ar}$), 7.06 (d, $^3J$=15.9 Hz, 2H, H$_{vin}$). $^{13}$C NMR (75 MHz, CDCl$_3$) δ (ppm): 188.2 (C), 150.6 (C), 141.8 (CH), 133.3 (C), 129.8 (CH), 126.0 (CH), 121.2 (CH). MS (EI) m/z: 402.1 (M+). Anal. calcd for C$_{19}$H$_{12}$F$_6$O$_3$: C, 56.73; H, 3.01. Found: C, 56.44; H, 3.10%.

(1E,4E)-1,5-Bis(4-cyanophenyl)penta-1,4-dien-3-one (NW307.2)

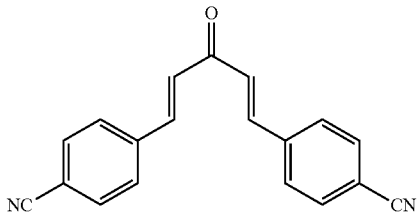 [SMILES: N#Cc1ccc(/C=C/C(=O)/C=C/c2ccc(C#N)cc2)cc1]

A mixture of 4-formyl-benzonitrile (1.1 g, 8.4 mmol), acetone (308 μL, 4.2 mmol), LiClO$_4$ (892 mg, 8.4 mmol) and Et$_3$N (117 μL, 0.84 mmol) in toluene (8 mL) was stirred for 2 d at room temperature. A saturated aq. NH$_4$Cl-solution was added to the reaction mixture and the resulting yellow suspension was extracted with CH$_2$Cl$_2$ and the combined organic layers were dried with MgSO$_4$, filtered and evaporated in vacuo to afford NW307.2 as a yellow solid (300 mg, 25%). mp: 137-138° C. $^1$H NMR (250 MHz, DMSO-d$_6$) δ (ppm): 8.00 (d, $^3J$=8.3 Hz, 4H, H$_{Ar}$), 7.87 (d, $^3J$=16.2 Hz, 2H, H$_{vin}$), 7.94 (d, $^3J$=8.4 Hz, 4H, H$_{Ar}$), 7.51 (d, $^3J$=16.1 Hz, 2H, H$_{vin}$). $^{13}$C NMR (75 MHz, DMSO-d$_6$) δ (ppm): 188.5 (C), 141.2 (CH), 139.2 (C), 132.8 (CH), 129.2 (CH), 128.4 (CH), 118.6 (C), 112.4 (C). MS (FAB) m/z: 285.19 (M+). Anal. calcd for C$_{19}$H$_{12}$N$_2$O: C, 80.27; H, 4.25; N, 9.85. Found: C, 80.04; H, 4.28; N, 9.76%.

(1E,4E)-1,5-Bis(4-chlorophenyl)penta-1,4-dien-3-one (NW308)

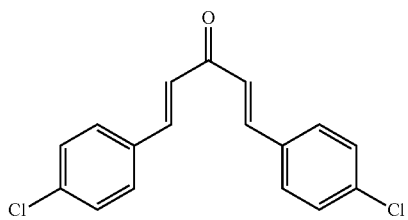 [SMILES: O=C(/C=C/c1ccc(Cl)cc1)/C=C/c1ccc(Cl)cc1]

A mixture of LiClO$_4$ (1.2 g, 11 mmol), acetone (418 μL, 5.7 mmol) and 4-chloro-benzaldehyde (1.6 g, 11 mmol) was treated with TEA (159 μL, 1.1 mmol) and stirred for 4 min at ambient temperature. A saturated aq. NH$_4$Cl solution was added to the reaction mixture and extracted with CH$_2$Cl$_2$. The combined organic layers were dried with MgSO$_4$, filtered and the solvent was removed in vacuo. The residue was recrystallized from CH$_2$Cl$_2$ to obtain NW308 as yellow crystals (586 mg, 34%). mp: 182-184° C. $^1$H NMR (300 MHz, CDCl$_3$) δ (ppm): 7.60 (d, $^3J$=15.9 Hz, 2H, H$_{vin}$), 7.46 (d, $^3J$=8.5 Hz, 4H, H$_{Ar}$), 7.31 (d, $^3J$=8.5 Hz, 4H, H$_{Ar}$), 6.95 (d, $^3J$=15.9 Hz, 2H, H$_{vin}$). $^{13}$C NMR (75 MHz, CDCl$_3$) δ (ppm): 188.3 (C), 142.0 (CH), 136.5 (C), 133.2 (C), 129.51 (CH), 129.2 (CH). MS (FAB) m/z: 303.1 (M+). Anal. calcd for C$_{17}$H$_{12}$Cl$_2$O: C, 67.35; H, 3.99; Cl, 23.39. Found: C, 67.33; H, 4.01; Cl, 23.17%.

(1E,4E)-1,5-Bis(4-hydroxy-3-methoxyphenyl)penta-1,4-dien-3-one (NW300)

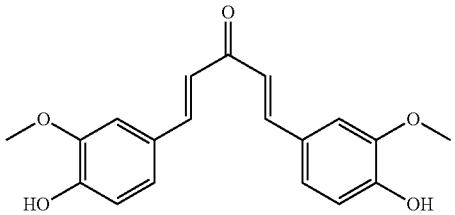

A mixture of vanillin (1 g, 6.6 mmol) in acetone (4.1 mL, 3.3 mmol) were dissolved in glacial acetic acid (5 ml), saturated with anhydrous HCl and heated to 25-30° C. for 2 h. The mixture was stirred for 2 d at room temperature and treated with cold water. The resulting precipitate was filtered, washed with water, recrystallized from EtOH and dried in vacuo to afford NW300 as an orange solid (954 mg, 89%). mp: 115-117° C. $^1$H NMR (250 MHz, CD$_3$OD) δ (ppm): 7.73 (d, $^3$J=15.8 Hz, 2H, H$_{vin}$), 7.31 (d, $^4$J=1.9 Hz, 2H, H$_{Ar}$), 7.20 (dd, $^3$J=8.2 Hz, $^4$J=1.9 Hz, 2H, H$_{Ar}$), 7.11 (d, $^3$J=15.8 Hz, 2H, H$_{vin}$), 6.86 (d, $^3$J=8.2 Hz, 2H, H$_{Ar}$), 3.94 (s, 6H, CH$_3$). $^{13}$C NMR (75 MHz, CD$_3$OD) δ (ppm): 191.7 (C), 151.0 (C), 149.5 (C), 145.5 (CH), 128.4 (C), 124.8 (CH), 123.8 (CH), 116.6 (CH), 112.1 (CH), 56.5 (CH$_3$). MS (FAB) m/z: 327.2 (M+). Anal. calcd for C$_{19}$H$_{18}$O$_5$.0.5H$_2$O: C, 68.05; H, 5.71. Found: C, 68.29; H, 5.68%.

(1E,4E)-1,5-Bis(3-(trifluoromethyl)-4-hydroxyphenyl)penta-1,4-dien-3-one (NW310.1)

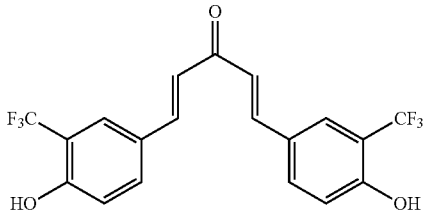 [SMILES: O=C(/C=C/c1ccc(O)c(C(F)(F)F)c1)/C=C/c1ccc(O)c(C(F)(F)F)c1]

A mixture of 3-(trifluoromethyl)-4-hydroxybenzaldehyde (2.19 g, 12 mmol) in acetone (423 µL, 5.8 mmol) was dissolved in glacial acetic acid (9 mL), saturated with anhydrous HCl and heated to 25-30° C. for 2 h. The red solution was stirred for 36 h and treated with cold water. The reaction mixture turned into a dark green suspension and the resulting precipitate was filtered, washed with water and dried in vacuo to afford NW310.1 as a dark green solid (740 mg, 32%). mp: 233-234° C. $^1$H NMR (250 MHz, CD$_3$OD) δ (ppm): 7.86 (d, $^4$J=1.6 Hz, 2H, H$_{Ar}$), 7.80 (d, $^3$J=8.8 Hz, $^4$J=1.9 Hz, 2H, H$_{Ar}$), 7.75 (d, $^3$J=16.1 Hz, 2H, H$_{vin}$), 7.15 (d, $^3$, J=15.9 Hz, 2H, H$_{vin}$), 7.02 (d, $^3$J=8.6 Hz, 2H, H$_{Ar}$). $^{13}$C NMR (75 MHz, CD$_3$OD) δ (ppm): 191.6 (C), 159.9 (C), 144.3 (CH), 134.8 (CH), 129.3 (CH), 127.8 (C), 127.3 (C), 125.3 (CH), 118.8 (CH). MS (FAB) m/z: 403.2 (M+). Anal. calcd for C$_{19}$H$_{12}$F$_6$O$_3$. 1H$_2$O: C, 54.17; H, 3.59. Found: C, 54.39; H, 3.31%.

(1E,4E)-1,5-Bis(4-hydroxy-3-(trifluoromethoxy)phenyl)penta-1,4-dien-3-one (NW317)

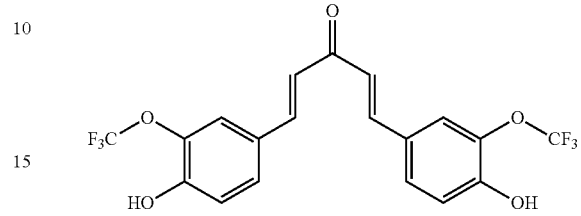

A mixture of 4-hydroxy-3-(trifluoromethoxy)benzaldehyde (600 mg, 2.9 mmol) in acetone (107 µL, 1.5 mmol) was dissolved in glacial acetic acid (8 mL), saturated with anhydrous HCl and heated to 25-30° C. for 2 h. The red solution was stirred for 36 h and treated with cold water. The red suspension turned dark green. The resulting precipitate was filtered, washed with water and dried in vacuo to afford NW317 as a yellow-green solid (314 mg, 50%). mp: 103-105° C. $^1$H NMR (300 MHz, CD$_3$OD) δ (ppm): 7.72 (d, $^3$J=15.9 Hz, 2H, H$_{vin}$), 7.62 (s, 2H, H$_{Ar}$), 7.58 (dd, $^3$J=8.5 Hz, $^4$J=2.0 Hz, 2H, H$_{Ar}$), 7.13 (d, $^3$J=15.9 Hz, 2H, H$_{vin}$), 7.03 (d, $^3$J=8.4 Hz, 2H, H$_{Ar}$). $^{13}$C NMR (75 MHz, CD$_3$OD) δ (ppm): 191.2 (C), 153.8 (C), 143.8 (CH), 138.4 (C), 130.1 (CH), 128.4 (C), 125.0 (CH), 124.4 (CH), 120.5 (CH). MS (FAB) m/z: 435.2 (M+). Light-sensitive!

(1E,4E)-1,5-Bis(3-bromo-2,5-dimethoxyphenyl)penta-1,4-dien-3-one (NW324.2)

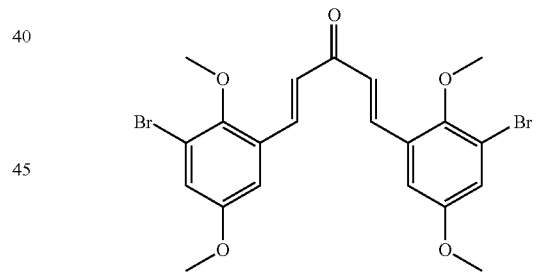

A mixture of 3-bromo-2,5-dimethoxybenzaldehyde (1.56 g, 6.4 mmol) in acetone (234 µL, 3.2 mmol) and EtOH (15 mL) was stirred for 15 min at room temperature. A solution of NaOH (382 mg, 9.5 mmol) in H$_2$O (8 mL) was added and the reaction mixture was stirred for further 24 h at ambient temperature. The resulting precipitate was filtered, recrystallized from EtOH and dried in vacuo to afford NW324.2 as a pale yellow solid (1.6 g, 92%). mp: 122-125° C. $^1$H NMR (250 MHz, CDCl$_3$) δ (ppm): 7.95 (d, $^3$J=16.2 Hz, 2H, H$_{vin}$), 7.20 (d, $^4$, J=2.8 Hz, 2H, H$_{Ar}$), 7.15 (d, $^3$J=16.3 Hz, 2H, H$_{vin}$), 7.14-7.09 (m, 2H, H$_{Ar}$), 3.85 (s, 6H, OCH$_3$).
$^{13}$C NMR (75 MHz, CDCl$_3$) δ (ppm): 188.9 (C), 156.2 (C), 150.6 (C), 137.8 (CH), 130.2 (C), 127.6 (CH), 120.9 (CH), 112.2 (CH), 62.0 (OCH$_3$), 55.9 (OCH$_3$). MS (FAB) m/z: 513.0 (M+).
Anal. calcd for C$_{21}$H$_{20}$Br$_2$O$_5$.0.5H$_2$O: C, 48.39; H, 4.06. Found: C, 48.37; H, 3.96%.

(1E,4E)-1,5-Bis(3-bromo-2-hydroxy-5-methoxyphenyl)penta-1,4-dien-3-one (NW326.4)

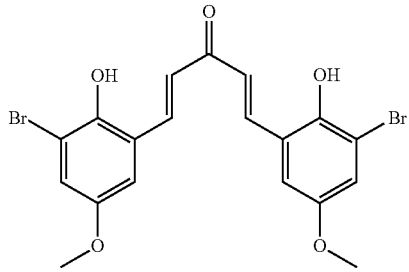 [SMILES: COc1cc(Br)c(O)c(/C=C/C(=O)/C=C/c2cc(OC)cc(Br)c2O)c1]

A suspension of 3-bromo-2-hydroxy-5-methoxybenzaldehyde (1.22 g, 5.3 mmol) in acetone (194 μL, 2.6 mmol) and EtOH (5 mL) was stirred for 15 min at ambient temperature. A solution of NaOH (317 mg, 7.9 mmol) in $H_2O$ (1.3 mL) was added and the yellow suspension was stirred for further 3 d at room temperature. The reaction mixture was treated with aq. HCl solution (1N) and the resulting precipitate was filtered and dried in vacuo to obtain NW326.4 as an orange solid (741 mg, 57%). mp: 155-157° C. $^1$H NMR (300 MHz, DMSO-$d_6$) δ (ppm): 9.45 (s, 2H, O$\underline{H}$), 7.99 (d, $^3$J=16.0 Hz, 2H, H$_{vin}$), 7.34 (d, $^3$J=16.0 Hz, 2H, H$_{vin}$), 7.33 (d, $^4$J=2.9 Hz, 2H, H$_{Ar}$), 7.25 (d, $^4$J=2.9 Hz, 2H, H$_{Ar}$), 3.78 (s, 6H, OC$\underline{H}_3$). $^{13}$C NMR (75 MHz, DMSO-$d_6$) δ (ppm): 188.8 (C), 153.5 (C), 147.5 (C), 137.8 ($\underline{C}$H), 127.4 ($\underline{C}$H), 125.6 (C), 121.2 ($\underline{C}$H), 113.9 (C), 111.9 ($\underline{C}$H), 56.3 (O$\underline{C}$H$_3$). MS (FAB) m/z: 485.1 (M+). The purity of the compound was confirmed by HPLC analysis; 60% decomposition after 5 days.

(1E,4E)-1,5-Bis(2-hydroxy-5-methoxyphenyl)penta-1,4-dien-3-one (NW327.2)

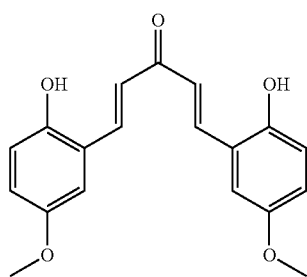 [SMILES: COc1ccc(O)c(/C=C/C(=O)/C=C/c2cc(OC)ccc2O)c1]

A mixture of 2-hydroxy-5-methoxybenzaldehyde (2 g, 13 mmol) in acetone (483 μL, 7 mmol) and EtOH (13 mL) was stirred for 15 min at room temperature. A solution of NaOH (789 mg, 20 mmol) in $H_2O$ (3.3 ml) was added and the reaction mixture was stirred for further 24 h at ambient temperature. After addition of 1N HCl-solution, the resulting precipitate was filtered, recrystallized from EtOH and dried in vacuo to afford a golden solid (318 mg, 15%). $^1$H NMR (250 MHz, CD$_3$OD) δ (ppm): 8.09 (d, $^3$J=16.0 Hz, 2H, H$_{vin}$), 7.31 (d, $^3$J=16.1 Hz, 2H, H$_{vin}$), 9.19 (s, 2H, H$_{Ar}$), 6.89 (d, $^3$J=8.5 Hz, 2H, H$_{Ar}$), 6.82 (d, $^3$J=8.7 Hz, 2H, H$_{Ar}$), 3.81 (s, 6H, OC$\underline{H}_3$). $^{13}$C NMR (75 MHz, CD$_3$OD) δ (ppm): 188.7 (C), 152.3 (C), 151.4 (C), 137.8 ($\underline{C}$H), 125.6 ($\underline{C}$H), 121.6 (C), 118.7 ($\underline{C}$H), 117.2 ($\underline{C}$H), 111.8 ($\underline{C}$H), 55.5 (O$\underline{C}$H$_3$). MS (FAB) m/z: 327.2 (M+). Anal. calcd for $C_{21}H_{22}O_5$: C, 69.93; H, 5.56. Found: C, 70.01; H, 5.63%.

(1E,4E)-1,5-Bis(2,5-dimethoxyphenyl)penta-1,4-dien-3-one (NW331)

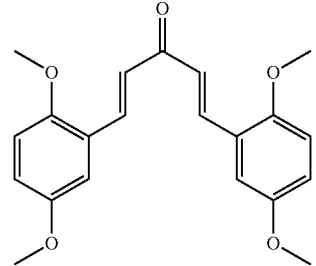 [SMILES: COc1ccc(OC)c(/C=C/C(=O)/C=C/c2cc(OC)ccc2OC)c1]

A mixture of 2,5-dimethoxybenzaldehyde (3 g, 18 mmol) in acetone (663 μL, 9 mmol) and EtOH (30 mL) was stirred for 15 min at room temperature. A solution of NaOH (1.1 g, 27 mmol) in $H_2O$ (23 mL) was added and the reaction mixture was stirred for further 24 h at ambient temperature. The resulting precipitate was filtered, recrystallized from EtOH and dried in vacuo to afford NW331 as a bright yellow solid (2.9 g, 91%). mp: 103-104° C. $^1$H NMR (250 MHz, CDCl$_3$) δ (ppm): 8.06 (d, $^3$J=16.1 Hz, 2H, H$_{vin}$), 7.18 (d, $^4$J=2.9 Hz, 2H, H$_{Ar}$), 7.17 (d, $^3$J=16.1 Hz, 2H, H$_{vin}$), 6.96 (dd, $^3$J=9.0 Hz, $^4$J=2.8 Hz, 2H, H$_{Ar}$), 6.89 (d, $^3$J=9.0 Hz, 2H, H$_{Ar}$), 3.90 (s, 6H, OC$\underline{H}_3$), 3.84 (s, 6H, OC$\underline{H}_3$). $^{13}$C NMR (75 MHz, CDCl$_3$) δ (ppm): 189.8 (C), 153.5 (C), 153.1 (C), 138.0 ($\underline{C}$H), 126.3 ($\underline{C}$H), 124.5 ($\underline{C}$H), 117.2 ($\underline{C}$H), 113.2 ($\underline{C}$H), 112.3 ($\underline{C}$H), 56.1 (O$\underline{C}$H$_3$), 55.8 (O$\underline{C}$H$_3$). MS (FAB) m/z: 355.2 (M+). Anal. calcd for $C_{21}H_{22}O_5 \cdot 0.3H_2O$: C, 70.10; H, 6.33. Found: C, 70.22; H, 6.20%.

EXAMPLE 2

Symmetrical Diheteroarylidene Acetones

To generate symmetrical diheteroarylidene acetones (NW319, NW321 and BJ621) a Claisen-Schmidt reaction was performed with 2 equivalents of the aldehyde and 1 equivalent of 1,3-acetonedicarboxylic acid under acidic conditions (e.g. conc. HCl) for 2-24 h at room temperature and for 1 h at 80° C. (Scheme 3).

Scheme 3: Synthesis of symmertrical diheteroarylidene acetones

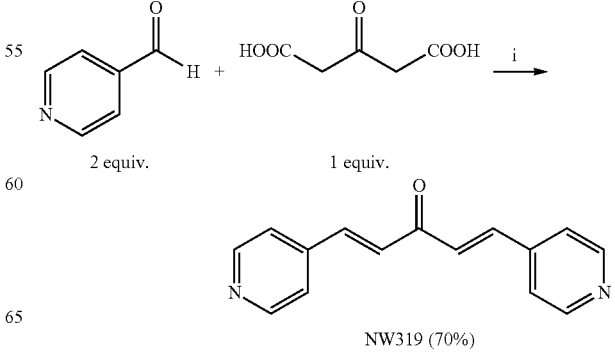

NW319 (70%)

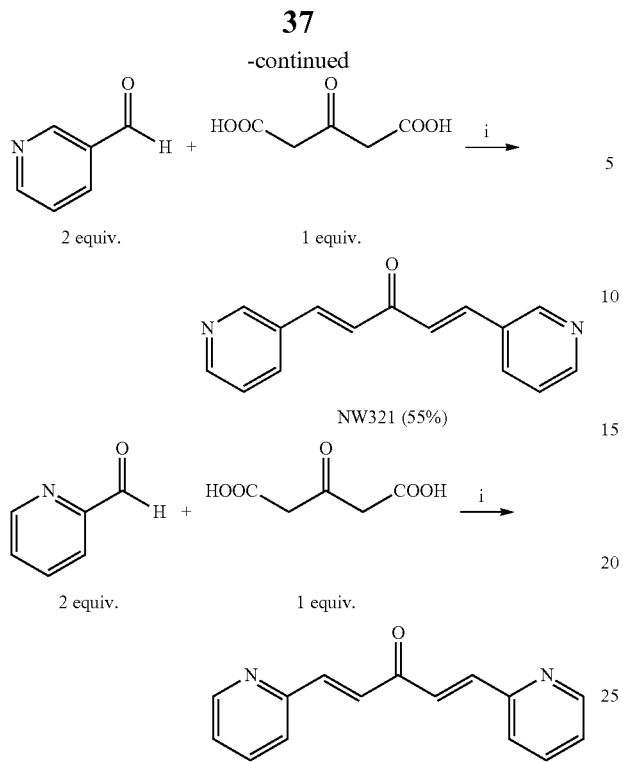

NW321 (55%)

BJ621

Reagents and conditions: (i) conc. HCl, EtOH, 2-24 h, RT, 1 h, 80° C.

The detailed synthesis is disclosed hereunder (1E,4E)-1,5-Di(pyridin-4-yl)penta-1,4-dien-3-one Dihydrochloride (NW319)

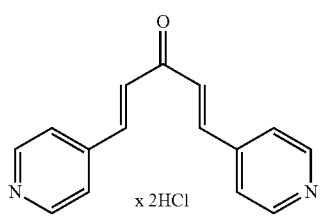 [SMILES: O=C(/C=C/c1ccncc1)/C=C/c1ccncc1]

1,3-Acetonedicarboxylic acid (3.15 g, 22 mmol) was dissolved in EtOH (30 mL) and stirred for 15 min at ambient temperature. 4-Pyridinecarboxaldehyde (4.06 mL, 43 mmol) was added dropwise and the mixture was stirred for 2 h at room temperature. The pale yellow solution was treated with concd. HCl (15 mL) and the reaction mixture were stirred for further 1 h at 80° C. The resulting yellow precipitate was filtered, recrystallized from $H_2O$/acetone (1:1) and dried in vacuo to obtain NW319 as bright yellow needles and as a hydrochloride salt (4.64 g, 70%). mp: 243-245° C. $^1$H NMR (250 MHz, $D_2O$) δ (ppm): 8.77 (d, $^3J$=6.8 Hz, 4H, $H_{Ar}$), 8.25 (d, $^3J$=6.8 Hz, 4H, $H_{Ar}$), 7.85 (d, $^3J$=16.2 Hz, 2H, $H_{vin}$), 7.62 (d, $^3J$=16.2 Hz, 2H, $H_{vin}$). $^{13}$C NMR (75 MHz, $D_2O$) δ (ppm): 191.5 (C), 153.1 (C), 142.6 (CH), 139.8 (CH), 134.8 (CH), 126.8 (CH). MS (FAB) m/z: 237.1 (M+). Anal. calcd for $C_{15}H_{12}N_2O.1.9HCl.0.7H_2O$: C, 56.63; H, 4.85; N, 8.80.; Cl, 21.17. Found: C, 56.60; H, 4.78; N, 8.73; Cl, 21.10%.

(1E,4E)-1,5-Di(pyridin-3-yl)penta-1,4-dien-3-one Dihydrochloride (NW321)

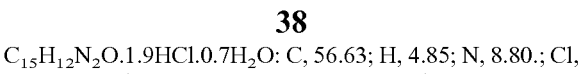

1,3-Acetonedicarboxylic acid (3.15 g, 22 mmol) was dissolved in EtOH (30 mL) and stirred for 15 min at ambient temperature. 3-Pyridinecarboxaldehyde (4.06 mL, 43 mmol) was added dropwise and the mixture was stirred for 2 h at room temperature. The yellow solution was treated with concd. HCl (15 mL) and the reaction mixture was stirred for further 1 h at 80° C. The resulting yellow precipitate was filtered, recrystallized from $H_2O$/acetone (1:1) and dried in vacuo to obtain NW321 as bright yellow needles and as a hydrochloride salt (3.7 g, 55%). mp: 260-262° C. $^1$H NMR (250 MHz, $D_2O$) δ (ppm): 9.02 (s, 2H, $H_{Ar}$), 8.83 (d, $^3J$=8.3 Hz, 2H, $H_{Ar}$), 8.74 (d, $^3J$=5.7 Hz, 2H, $H_{Ar}$), 8.06 (dd, $^3J$=8.1 Hz, $^3J$=6.0 Hz, 2H, $H_{Ar}$), 7.81 (d, $^3J$=16.2 Hz, 2H, $H_{vin}$), 7.44 (d, $^3J$=16.2 Hz, 2H, $H_{vin}$). $^{13}$C NMR (75 MHz, $D_2O$) δ (ppm): 191.6 (C), 145.9 (CH), 142.8 (CH), 142.2 (CH), 138.4 (CH), 135.5 (C), 131.3 (CH), 128.6 (CH). MS (FAB) m/z: 237.1 (M+). Anal. calcd for $C_{15}H_{12}H_2O.1.9HCl.2.1H_2O$: C, 55.37; H, 4.99; N, 8.61; Cl, 20.70. Found: C, 55.16; H, 4.99; N, 8.53; Cl, 20.89%.

EXAMPLE 3

Synthesis of Asymmetrical Dibenzylidene Acetones by Claisen-Schmidt Reaction

The starting benzalacetones were prepared by either a Claisen reaction or by a Horner-Wadsworth-Emmons reaction as illustrated in Scheme 4.

Scheme 4: Synthesis of starting benzalacetones

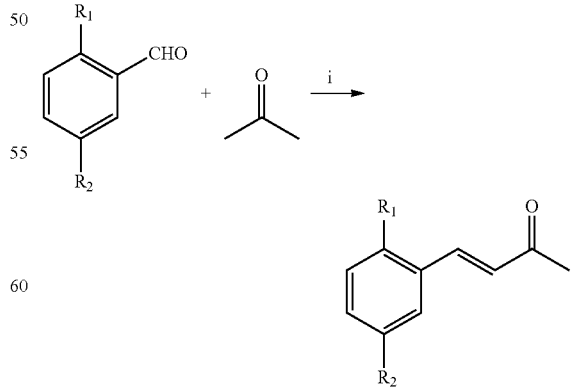

A NW-B543 ($R_1$ = $R_2$ = OMe) (59%)
B NW-B553 ($R_1$ = OH, $R_2$ = OMe) (90%)

-continued

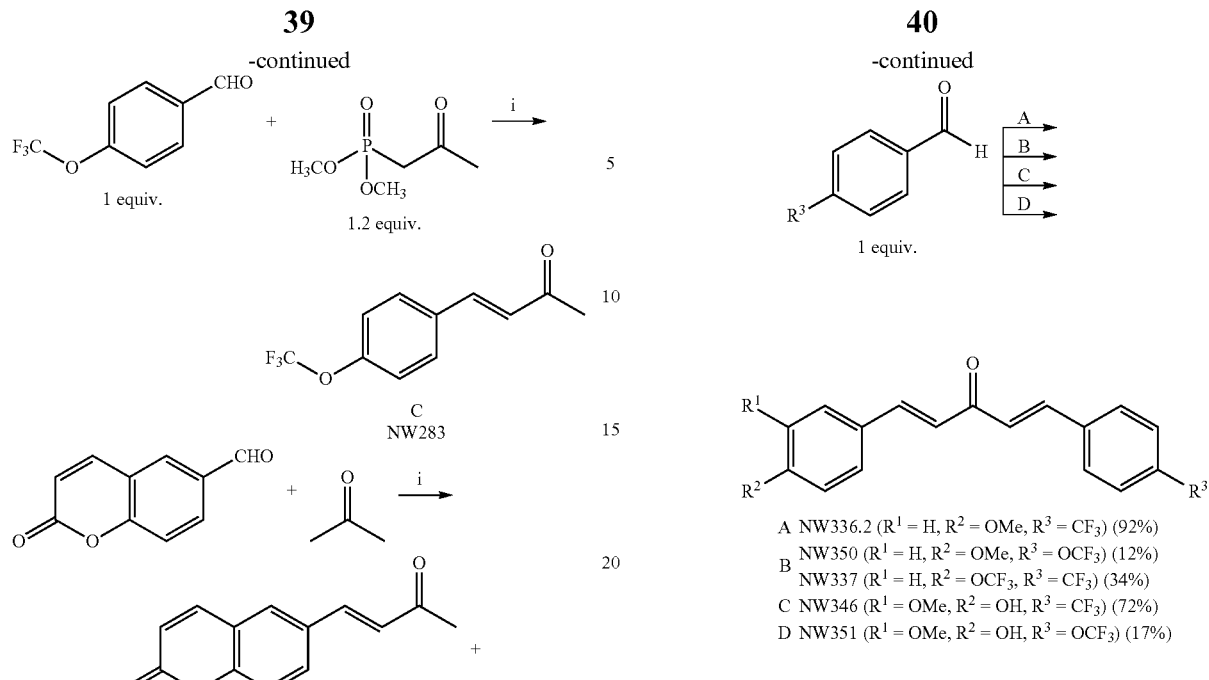

NW-355.1 (48%)

Reagents and conditions: (A) aq. NaOH, 24 h, RT; (B) aq. NaOH (10%), 3 h, RT, aq. HCl (6N), pH~1, 30 min, RT; (C) 1.8 equiv. K$_2$CO$_3$ in H$_2$O, 2 h, 0° C.; (D) (i) aq. K$_2$CO$_3$, 2d, RT, MeOH/2.5N H$_2$SO$_4$ (1:1), 24 h, reflux, (ii) aq. K$_2$CO$_3$, EtOH, 4 d, RT The favored asymmetrical dibenzylidene acetones (NW336.2, NW350, NW337, NW346, NW351 and NW355.1) were prepared via two consecutive Claisen-Schmidt reactions under various reaction conditions (A-D) depending on the different substituents on the aromatic ring. In the first step, 1 equivalent of the corresponding aldehyde and an excess of acetone were allowed to react under basic conditions. In the second step, the isolated unsaturated ketones and 1 equivalent of the other corresponding aldehyde were also transformed under basic conditions into the desired final products as illustrated in Scheme 5.

Scheme 5: Synthesis of asymmetrical debenzylidene acetones

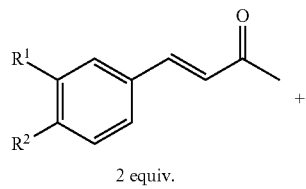

2 equiv.

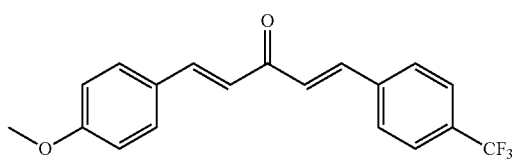 [SMILES: COc1ccc(/C=C/C(=O)/C=C/c2ccc(C(F)(F)F)cc2)cc1]

1 equiv.

A NW336.2 (R$^1$ = H, R$^2$ = OMe, R$^3$ = CF$_3$) (92%)
B NW350 (R$^1$ = H, R$^2$ = OMe, R$^3$ = OCF$_3$) (12%)
  NW337 (R$^1$ = H, R$^2$ = OCF$_3$, R$^3$ = CF$_3$) (34%)
C NW346 (R$^1$ = OMe, R$^2$ = OH, R$^3$ = CF$_3$) (72%)
D NW351 (R$^1$ = OMe, R$^2$ = OH, R$^3$ = OCF$_3$) (17%)

Reagents and conditions: (A) aq. NaOH, MeOH, 1 d, RT; (B) aq. K$_2$CO$_3$, EtOH, 4.5 h, 0° C., 2 h, RT; (C) aq. NaOH, EtOH, 1 d, RT, 6N aq. HCl, dark; (D) aq. K$_2$CO$_3$, EtOH, 3 h, 0° C., 3 d, 40° C.

The detailed synthesis is disclosed hereunder.

(1E,4E)-1-(4-(Trifluoromethyl)phenyl)-5-(4-methoxyphenyl)penta-1,4-dien-3-one (NW336.2)

(E)-4-(4-Methoxyphenyl)but-3-en-2-one (1 g, 5.7 mmol) was dissolved in MeOH (18 mL) and stirred for 5 min at room temperature. A solution of NaOH (500 mg, 12.5 mmol) in H$_2$O (34 mL) was added and the reaction mixture was stirred for further 1 h. After the dropwise addition of 4-(trifluoromethyl)-benzaldehyde (822 µl, 6.0 mmol), the mixture was stirred overnight at ambient temperature. The resulting yellow precipitate was filtered and dried in vacuo to obtain NW336.2 as a pale yellow solid (1.75 g, 92%). mp: 144-146° C. $^1$H NMR (300 MHz, CDCl$_3$) δ (ppm): 7.66 (d, $^3$J=15.9 Hz, 1H, H$_{vin}$), 7.64 (d, $^3$J=15.5 Hz, 1H, H$_{vin}$), 7.63 (d, $^3$J=9.0 Hz, 2H, H$_{Ar}$), 7.58 (d, $^3$J=8.6 Hz, 2H, H$_{Ar}$), 7.50 (d, $^3$J=8.8 Hz, 2H, H$_{Ar}$), 7.06 (d, $^3$J=16.0 Hz, 1H, H$_{vin}$), 6.87 (d, $^3$J=16.0 Hz, 1H, H$_{vin}$), 6.86 (d, $^3$J=8.8 Hz, 2H, H$_{Ar}$), 3.78 (s, 3H, OCH$_3$). $^{13}$C NMR (75 MHz, CDCl$_3$) δ (ppm): 188.4 (C), 161.9 (C), 143.9 (CH), 140.8 (CH), 138.4 (q, $^4$J(C, F)=1.3 Hz, CH), 131.7 (q, $^2$J(C, F)=32.7 Hz, C), 130.3 (CH), 128.4 (CH), 127.6 (CH), 127.3 (C), 125.9 (q, $^3$J(C, F)=3.8 Hz, CH), 123.9 (q, $^1$J(C, F)=272.2 Hz, C), 123.2 (CH), 114.5 (CH), 55.5 (O CH₃). MS (FAB) m/z: 333.1 (M+). Anal. calcd for C₁₉H₁₅F₃O₂: C, 68.67; H, 4.55. Found: C, 68.81; H, 4.63%.

(1E,4E)-1-(4-Methoxyphenyl)-5-(4-(trifluoromethoxy)phenyl)penta-1,4-dien-3-one (NW350)

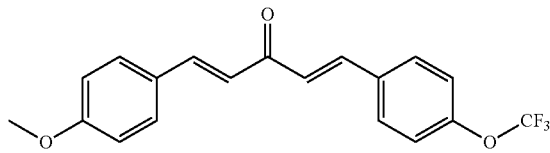 [SMILES: COc1ccc(/C=C/C(=O)/C=C/c2ccc(OC(F)(F)F)cc2)cc1]

A suspension of (E)-4-(4-methoxyphenyl)-but-3-en-2-one (615 mg, 3.5 mmol) in EtOH (10 mL) was stirred for 5 min at 0° C. A solution of K₂CO₃ (965 mg, 7.0 mmol) in H₂O (5 mL) was added and the reaction mixture was stirred for further 10 min at 0° C. After the dropwise addition of 4-(trifluoromethoxy)-benzaldehyde (528 µl, 3.7 mmol), the pale yellow suspension was stirred for further 4 h at 0° C. The resulting yellow precipitate was filtered and dried in vacuo to obtain NW350 as a pale yellow solid (145 mg, 12%). mp: 105-107° C.

¹H NMR (300 MHz, CDCl₃) δ (ppm): 7.82-7.44 (m, 6H, H$_{Ar}$+H$_{vin}$), 7.34-7.24 (m, 2H, H$_{Ar}$), 7.14-6.90 (m, 4H, H$_{Ar}$+H$_{vin}$), 3.89 (s, 3H, OCH₃). ¹³C NMR (75 MHz, CDCl₃) δ (ppm): 188.5 (C), 161.8 (C), 150.4 (C), 143.6 (CH), 141.0 (CH), 133.6 (C), 130.2 (CH), 129.7 (CH), 127.4 (C), 126.3 (CH), 123.3 (CH), 121.2 (CH), 114.5 (CH), 55.4 (OCH₃). MS (FAB) m/z: 349.1 (M+). Anal. calcd for C₁₉H₁₅F₃O₃.1.1H₂O: C, 61.99; H, 4.71. Found: C, 61.86; H, 4.44%.

(1E,4E)-1-(4-(Trifluoromethyl)phenyl)-5-(4-(trifluoromethoxy)phenyl)penta-1,4-dien-3-one (NW337)

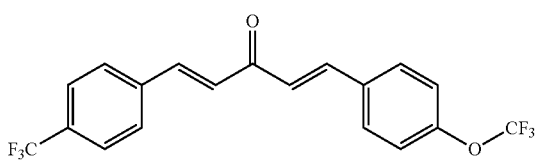 [SMILES: O=C(/C=C/c1ccc(OC(F)(F)F)cc1)/C=C/c1ccc(C(F)(F)F)cc1]

A solution of (E)-4-(4-(trifluoromethoxy)-phenyl)-but-3-en-2-one (623 mg, 2.7 mmol) in EtOH (10 mL) was stirred for 5 min at 0° C. A solution of K₂CO₃ (748 mg, 5.4 mmol) in H₂O (4 mL) was added and the reaction mixture was stirred for further 1 h. After the dropwise addition of 4-(trifluoromethyl)-benzaldehyde (392 µl, 2.9 mmol), the mixture was continued to stir for 4 h at 0° C. and for 2 h at ambient temperature. The resulting yellow precipitate was filtered and dried in vacuo to obtain NW337 as a pale yellow solid (337 mg, 34%). mp: 97-99° C. ¹H NMR (300 MHz, CDCl₃) δ (ppm): 7.76 (d, ³J=16.1 Hz, 1H, H$_{vin}$), 7.75 (d, ³J=15.7 Hz, 1H, H$_{vin}$), 7.74 (d, ³J=8.8 Hz, 2H, H$_{Ar}$), 7.69 (d, ³J=8.1 Hz, 2H, H$_{Ar}$), 7.67 (d, ³J=8.7 Hz, 2H, H$_{Ar}$), 7.29 (d, ³J=8.0 Hz, 2H, H$_{Ar}$), 7.15 (d, ³J=16.0 Hz, 1H, H$_{vin}$), 7.07 (d, ³J=16.0 Hz, 1H, H$_{vin}$). ¹³C NMR (75 MHz, CDCl₃) δ (ppm): 188.2 (C), 150.7 (C), 142.1 (CH), 141.6 (CH), 138.1 (q, ⁴J(C, F)=1.3 Hz, CH), 133.2 (C), 132.0 (q, ²J(C, F)=32.7 Hz, C), 129.9 (CH), 128.5 (CH), 127.3 (CH), 126.0 (q, ³J(C, F)=3.8 Hz, CH), 125.9 (CH), 122.1 (C), 122.0 (C), 121.2 (CH), 118.7 (C). MS (FAB) m/z: 387.1 (M+). Anal. calcd for C₁₉H₁₂F₆O₂.0.5H₂O: C, 57.73; H, 3.31. Found: C, 57.75; H, 3.20%.

(1E,4E)-1-(4-(Trifluoromethyl)-phenyl)-5-(4-(hydroxy-3-methoxyphenyl)penta-1,4-dien-3-one (NW346)

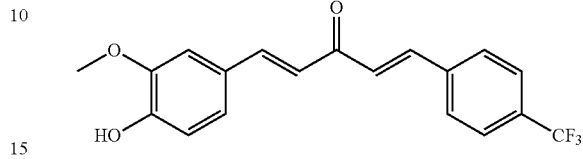

(E)-4-(4-Hydroxy-3-methoxyphenyl)but-3-en-2-one (500 mg, 2.6 mmol) was dissolved in EtOH (8 mL) and stirred in the dark for 5 min at room temperature. A solution of NaOH (229 mg, 5.7 mmol) in H₂O (16 mL) was added and the reaction mixture was stirred for further 1 h. The yellow solution turned red. After the dropwise addition of 4-(trifluoromethyl)-benzaldehyde (377 µl, 2.8 mmol), the mixture was continued to stir overnight at ambient temperature. The dark red solution was acidified with aq. HCl (6 N) solution and the resulting bright yellow precipitate was filtered, recrystallized from EtOH and dried in vacuo to obtain NW346 as bright yellow crystals (483 mg, 66%). mp: 135-137° C. ¹H NMR (300 MHz, CD₃OD) δ (ppm): 7.87 (d, ³J=8.2 Hz, 2H, H$_{Ar}$), 7.78 (d, ³J=15.9 Hz, 1H, H$_{vin}$), 7.77 (d, ³J=16.1 Hz, 1H, H$_{vin}$), 7.71 (d, ³J=8.3 Hz, 2H, H$_{Ar}$), 7.37 (d, ³J=16.0 Hz, 1H, H$_{vin}$), 7.31 (d, ⁴J=1.9 Hz, 1H, H$_{Ar}$), 7.21 (dd, ³J=8.2 Hz, ⁴J=1.9 Hz, 1H, H$_{Ar}$), 7.09 (d, ³J=15.9 Hz, 1H, H$_{vin}$), 6.86 (d, ³J=8.2 Hz, 1H, H$_{Ar}$), 3.93 (s, 3H, OCH₃). ¹³C NMR (75 MHz, CD₃OD) δ (ppm): 191.1 (C), 151.3 (C), 149.5 (C), 146.7 (CH), 142.1 (CH), 140.2 (q, ⁴J(C, F)=1.3 Hz, CH), 132.6 (q, ²J(C, F)=32.5 Hz, C), 129.9 (CH), 129.0 (CH), 128.1 (C), 126.9 (q, ³J(C, F)=3.8 Hz, CH), 125.1 (CH), 123.6 (CH), 116.7 (CH), 112.2 (CH), 56.5 (OCH₃). MS (FAB) m/z: 349.2 (M+). Anal. calcd for C₁₉H₁₄F₃O₃: C, 65.52; H, 4.34. Found: C, 65.25; H, 4.39%.

(1E,4E)-1-(4-Hydroxy-3-methoxyphenyl)-5-(4-(trifluoromethoxy)phenyl)penta-1,4-dien-3-one (NW351)

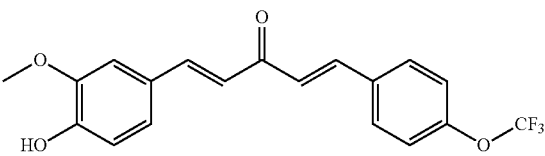 [SMILES: COc1cc(/C=C/C(=O)/C=C/c2ccc(OC(F)(F)F)cc2)ccc1O]

A suspension of (E)-4-(4-hydroxy-3-methoxyphenyl)but-3-en-2-one (600 mg, 3.1 mmol) in EtOH (10 mL) was stirred for 5 min at 0° C. A solution of K₂CO₃ (863 mg, 6.2 mmol) in H₂O (5 mL) was added and the reaction mixture was stirred for further 10 min at 0° C. After the dropwise addition of 4-(trifluoromethoxy)-benzaldehyde (473 µl, 3.3 mmol), the orange suspension was heated to reflux for 4 d at 40° C. The solvent was evaporated in vacuo and the resulting residue was purified by flash-chromatography on silica gel (Hexane/EtOAc 2:1) and dried in vacuo to obtain NW351 as a yellow solid (191 mg, 17%). mp: 93-95° C. ¹H NMR (300 MHz, CD₃OD) δ (ppm): 7.72 (d, ³J=8.4 Hz, 2H, H$_{Ar}$), 7.71 (d, $^3J$=15.9 Hz, 1H, H$_{vin}$), 7.68 (d, $^3J$=15.6 Hz, 1H, H$_{vin}$), 7.27 (d, $^3J$=8.3 Hz, 2H, H$_{Ar}$), 7.24 (d, $^4J$=1.9 Hz, 1H, H$_{Ar}$), 7.19 (d, $^3J$=16.0 Hz, 1H, H$_{vin}$), 7.15 (dd, $^3J$=8.4 Hz, $^4J$=2.0 Hz, 1H, H$_{Ar}$), 7.02 (dd, $^3J$=15.9 Hz, $^5J$=0.99, Hz, 1H, H$_{vin}$), 6.83 (dd, $^3J$=8.2 Hz, $^5J$=0.9 Hz, 1H, H$_{Ar}$), 3.89 (d, $^5J$=0.9, 3H, OCH$_3$). $^{13}$C NMR (75 MHz, CD$_3$OD) δ (ppm): 191.1 (C), 151.7 (q, $^4J$ (C, F)=1.7 Hz), 151.2 (C), 149.4 (C), 146.4 (CH), 142.4 (CH), 135.4 (C), 131.3 (CH), 128.1 (C), 127.6 (CH), 125.0 (CH), 123.6 (CH), 122.3 (CH), 120.2 (C), 116.7 (CH), 112.2 (CH), 56.5 (OCH$_3$). MS (FAB) m/z: 365.2 (M+). Anal. calcd for C$_{19}$H$_{15}$F$_3$O$_4$: C, 62.64; H, 4.15. Found: C, 62.45; H, 4.39%.

6-(1E,4E)-5-(4-(Trifluoromethyl)phenyl)-3-oxopenta-1,4-dienyl)-2H-chromen-2-one (NW355P)

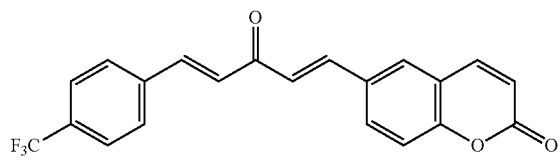 [SMILES: O=C(/C=C/c1ccc(C(F)(F)F)cc1)/C=C/c1ccc2oc(=O)ccc2c1]

To a grey suspension of 6-((E)-3-oxobut-1-enyl)-2H-chromen-2-one (1 g, 4.7 mmol) in EtOH (12 mL) was added dropwise a solution of K$_2$CO$_3$ (1.3 g, 9.3 mmol) in H$_2$O (6 mL). The grey suspension turned yellow. After addition of 4-(trifluoromethyl)-benzaldehyde (0.7 mL, 862 mg, 4.9 mmol), the reaction mixture was stirred for 4d at room temperature. The orange suspension turned red and the resulting precipitate was filtered and purified by flash-chromatography on silica gel (Hexane/EtOAc 1:1) to obtain NW355P as a white solid (830 mg, 48%). mp: 153-155° C. $^1$H NMR (250 MHz, DMSO-d$_6$) δ (ppm): 8.64 (d, $^3J$=1.9 Hz, 1H, H$_{Ar}$), 8.60-8.47 (m, 4H, H$_{Ar}$), 8.39 (d, $^3J$=16.2 Hz, 1H, H$_{vin}$), 8.39-8.26 (m, 3H, H$_{vin}$, H$_{Ar}$), 8.00 (d, $^3J$=16.2 Hz, 1H, H$_{vin}$), 7.97 (d, $^3J$=8.5 Hz, 1H, H$_{Ar}$), 7.89 (d, $^3J$=16.1 Hz, 1H, H$_{vin}$), 7.04 (d, $^3J$=9.6 Hz, 1H, H$_{Ar}$). $^{13}$C NMR (75 MHz, DMSO-d$_6$) δ (ppm): 188.4 (C), 159.6 (C), 154.7 (C), 143.9 (CH), 141.8 (CH), 140.9 (CH), 131.7 (CH), 131.1 (C), 129.1 (CH), 128.8 (CH), 127.9 (CH), 126.0 (CH), 125.8 (CH), 119.1 (C), 117.2 (CH), 117.0 (CH).

MS (FAB) m/z: 371.1 (M+). Anal. calcd for C$_{21}$H$_{13}$F$_3$O$_3$: C, 68.11; H, 3.54. Found: C, 67.72; H, 3.72%.

EXAMPLE 4

Synthesis of Dissymmetric Dibenzylidene Acetones Through a One-pot Coupling-Isomerization Procedure (CIP)

Although the synthesis of dissymmetric dibenzylidene acetones could be achieved according to the procedure described in Example 3, some compounds failed to be synthesized with these traditional conditions. Here we would describe a one-pot catalytic procedure for the simple synthesis of electron-deficient dibenzylidene acetones. This work was based on a procedure described by Braun et at (Chem. Eur. J. 2006, 12, 9081-9094) and products were obtained according to the following steps (Scheme 6).

Scheme 6: Synthesis of dissymmetric dibenzylidene acetones via a one-pot CIP

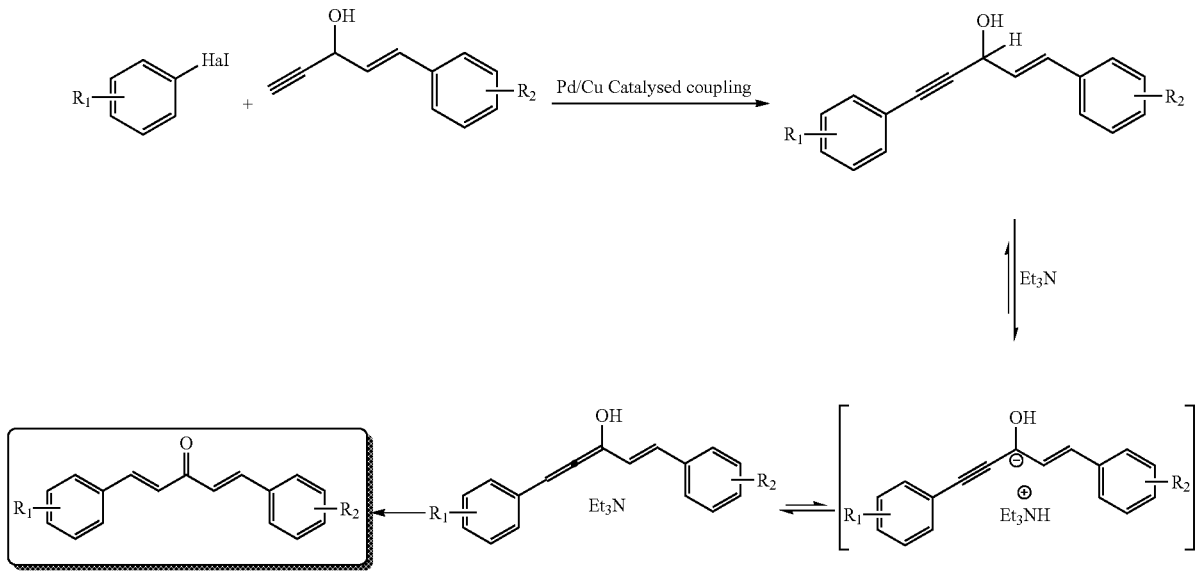

According to the traditional Sonogashira coupling, a propargylic alcohol reacts with an (hetero)aryl halide bearing an electron-withdrawing group in para-position in presence of a mix of palladium catalyst, copper iodide and a base. A base-assisted isomerization subsequently leads to the formation of the desired dibenzylidene acetone. The unsaturated propargylic alcohol can be easily synthesized through the Grignard addition of commercially available ethynylmagnesium bromide on a cinnamaldehyde. This usually leads to desired product in good to excellent yields (Scheme 7).

Scheme 7: Synthesis of unsaturated propargylic alcohol starting material

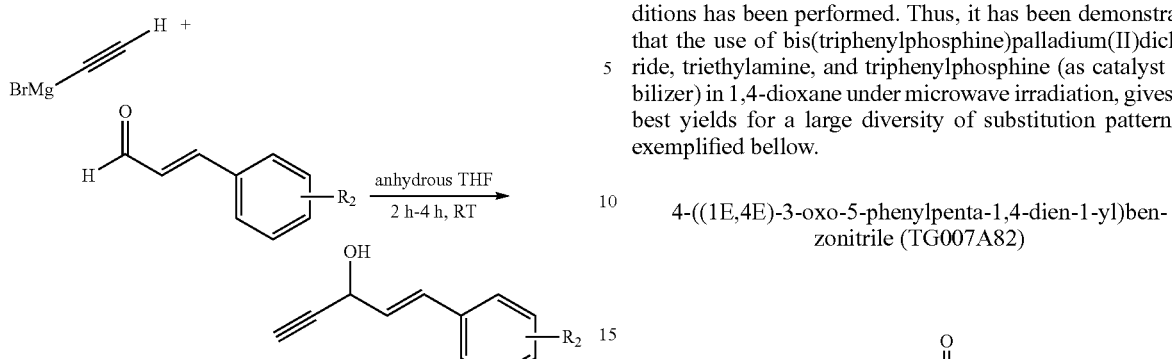

Regarding the opportunity to introduce the diversity through the use of highly substituted (hetero)aryl halides, several starting material has been considered. They are given in Table I.

In order to be able to use this broad variety of starting material, an optimization study on the coupling reaction conditions has been performed. Thus, it has been demonstrated that the use of bis(triphenylphosphine)palladium(II)dichloride, triethylamine, and triphenylphosphine (as catalyst stabilizer) in 1,4-dioxane under microwave irradiation, gives the best yields for a large diversity of substitution pattern, as exemplified bellow.

4-((1E,4E)-3-oxo-5-phenylpenta-1,4-dien-1-yl)benzonitrile (TG007A82)

TABLE I example of (hetero)aryl halides that have been considered to be used in the CIP procedure

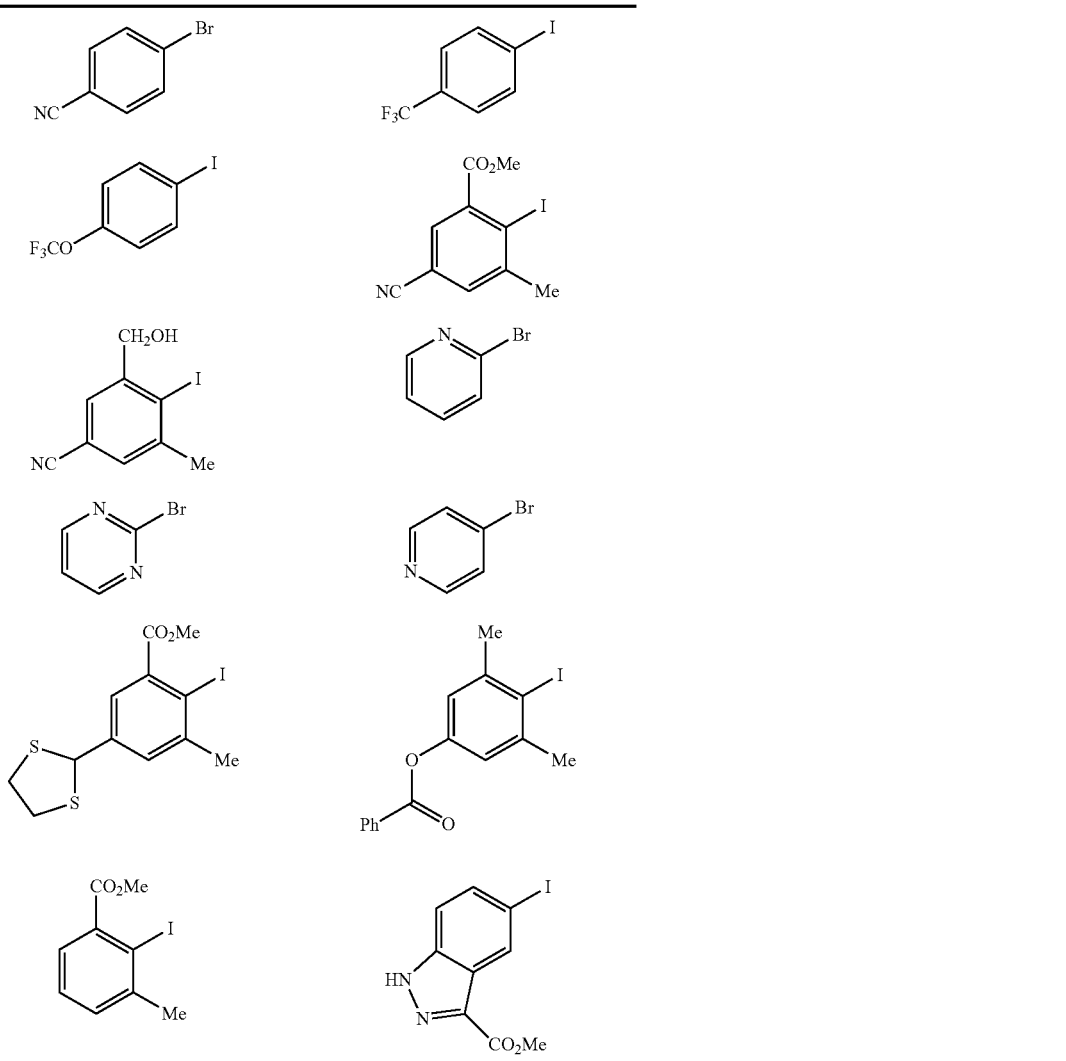

4-bromobenzonitrile (182 mg, 1 mmol), phenylpent-1-en-4-yn-3-ol (190 mg, 1.2 mmol), bis(triphenylphosphine)palladium(II)dichloride (14 mg, 0.02 mmol), copper iodide (3 mg, 0.03 mmol) and triphenylphosphine (52 mg, 0.2 mmol) were introduced in a 10 mL microwave vial flushed with argon. This was diluted with anhydrous triethylamine (700 μL, 4 mmol) in anhydrous degased 1,4-dioxane (1.3 mL). The solution was heated under microwave irradiation at 120° C. for 45 min. The reaction mixture was poured into a mix of 1M aqueous solution of hydrochloric acid (10 mL) and saturated aqueous ammonium chloride solution (10 mL), and this was extracted with ethyl acetate (3×15 mL). The combined organic layers were dried over magnesium sulfate, filtered, and evaporated to dryness to give crude product which was purified by flash chromatography (SiO$_2$, 30% ethyl acetate in dichloromethane). This gave pure final compound TG007A82 (160 mg, 62%) as a light yellow powder.

$^1$H COSY NMR (500 MHz, CD$_2$Cl$_2$) δ (ppm): 7.75 (d, $^3$J$_{trans}$=16.4 Hz, 1H, ArCH=), 7.72 (m, 4H, Ar), 7.69 (d, $^3$J$_{trans}$=15.5 Hz, 1H, ArCH=), 7.64-7.66 (m, 2H, Ar), 7.44 (m, 3H, Ar), 7.18 (d, $^3$J$_{trans}$=15.5 Hz, 1H, =CHC(O)), 7.09 (d, $^3$J$_{tran}$=16.4 Hz, 1H, =CHC(O))

$^{13}$C NMR (125 MHz, CD$_2$Cl$_2$) δ (ppm): 188.3 (C), 144.1 (CH), 140.7 (CH), 139.6 (C), 135.0 (C), 133.0 (CH), 131.1 (CH), 129.4 (CH), 129.0 (CH), 128.8 (CH), 128.5 (CH), 125.7 (CH), 118.8 (CN), 113.7 (ArC—CN)

MS(EI): m/z=259

(1E,4E)-1-phenyl-5-(4-(trifluoromethyl)phenyl)penta-1,4-dien-3-one (TG008A86)

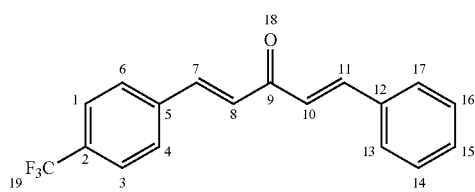 [SMILES: O=C(/C=C/c1ccccc1)/C=C/c1ccc(C(F)(F)F)cc1]

4-iodobenzotrifluoride (150 μL, 1 mmol), phenylpent-1-en-4-yn-3-ol (190 mg, 1.2 mmol), bis(triphenylphosphine)palladium(II) dichloride (14 mg, 0.02 mmol), copper iodide (3 mg, 0.03 mmol) and triphenylphosphine (52 mg, 0.2 mmol) were introduced in a 10 mL microwave vial flushed with argon. This was diluted with anhydrous triethylamine (700 μL, 4 mmol) in anhydrous degased 1,4-dioxane (1.3 mL). The solution was heated under microwave irradiation at 120° C. for 45 min. The reaction mixture was poured into a mix of 1M aqueous solution of hydrochloric acid (10 mL) and saturated aqueous ammonium chloride solution (10 mL), and this was extracted with dichloromethane (3×15 mL). The combined organic layers were dried over magnesium sulfate, filtered, and evaporated to dryness to give crude product which was purified by flash chromatography (SiO$_2$, DCM/Hexanes 3:7). The resulting yellow solid was recrystallized (EtOH/Hexanes 1:3) to give pure final compound TG008A86 as a pale yellow powder (155 mg, 51%).

$^1$H COSY NMR (200 MHz, CDCl$_3$) δ (ppm): 7.78 (d, $^3$J$_{trans}$=14.9 Hz, 1H, ArCH=), 7.75 (d, $^3$J$_{trans}$=14.6 Hz, 1H, ArCH=), 7.73-7.61 (m, 6H, Ar and ArCH=), 7.46-7.41 (m, 3H, Ph), 7.16 (d, $^3$J$_{trans}$=14.8 Hz, 1H, =CHC(O)), 7.08 (d, $^3$J$_{trans}$=14.6 Hz, 1H, =CHC(O))

$^{13}$C NMR (75.5 MHz, CDCl$_3$) δ (ppm): 188.7 (C9), 144.2 (CH), 144.4 (CH), 138.4 (m, C5), 134.8 (C), 132.1 (q, $^2$J=32 Hz, C2), 131.0 (CH), 129.2 (CH), 128.7 (CH), 128.6 (CH), 127.6 (CH), 125.9 (q, $^3$J=3.6 Hz, C3), 125.5 (CH), 123.8 (q, $^1$J=271 Hz, C19)

MS(EI): m/z=302

(1E,4E)-1-(4-(dimethylamino)phenyl)-5-(4-(trifluoromethyl)phenyl)penta-1,4-dien-3-one (TG009A94)

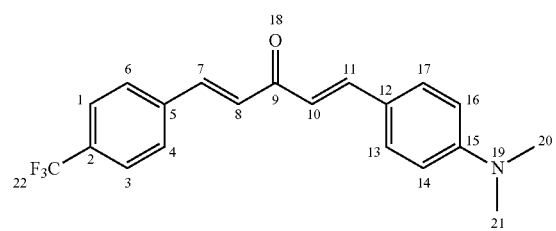

4-iodobenzotrifluoride (150 μL, 1 mmol), 1-(4-(dimethylamino)phenyl)pent-1-en-4-yn-3-ol (242 mg, 1.2 mmol), bis(triphenylphosphine)palladium(II) dichloride (14 mg, 0.02 mmol), copper iodide (3 mg, 0.03 mmol) and triphenylphosphine (52 mg, 0.2 mmol) were introduced in a 10 mL microwave vial flushed with argon. This was diluted with anhydrous triethylamine (700 μL, 4 mmol) in anhydrous degased 1,4-dioxane (1.3 mL). The solution was heated under microwave irradiation at 120° C. for 45 min. The reaction mixture was poured into brine (20 mL), and this was extracted with dichloromethane (3×20 mL). The combined organic layers were dried over magnesium sulfate, filtered, and evaporated to dryness to give crude product which was purified by flash chromatography (SiO$_2$, 30% ethyl acetate in dichloromethane). The resulting yellow solid was triturated in diethyl ether to give pure final compound TG009A94 as a bright orange powder (200 mg, 58%).

$^1$H NMR (200 MHz, CDCl$_3$) δ (ppm): 7.62-7.73 (m, 6H, Ar), 7.51 (d, $^3$J=9 Hz, 2H, H13-17), 7.13 (d, $^3$J$_{trans}$=16 Hz, 1H, =CHC(O)), 6.85 (d, $^3$J$_{trans}$=16 Hz, 1H, =CHC(O)), 6.68 (d, $^3$J=8.5 Hz, 2H, H14-16), 3.03 (s, 6H, N(CH$_3$)$_2$)

$^{13}$C NMR (75.5 MHz, CDCl$_3$) δ (ppm): 188.5 (C9), 152.4 (C), 145.2 (CH), 140.1 (CH), 138.9 (m, C5), 131.6 (q, $^2$J=32.5 Hz, C2), 130.7 (CH), 128.5 (CH), 128.1 (CH), 126.0 (q, $^3$J=3.8 Hz, C3), 123.9 (q, $^1$J=269 Hz, C22), 122.5 (C), 120.8 (CH), 112.1 (CH), 40.3 (N(CH$_3$)$_2$)

MS(EI): m/z=345

Anal. calcd for C$_{20}$H$_{18}$F$_3$NO: C, 69.56; H, 5.25; N, 4.06. Found: C, 69.57; H, 5.54; N, 3.94

(1E,4E)-1-phenyl-5-(pyrimidin-2-yl)penta-1,4-dien-3-one Hydrochloride (TG010A95)

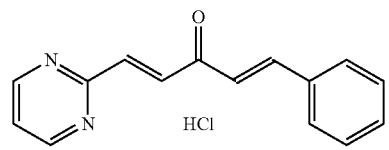 [SMILES: O=C(/C=C/c1ccccc1)/C=C/c1ncccn1 ; Cl]

2-bromopyrimidine (159 mg, 1 mmol), phenylpent-1-en-4-yn-3-ol (190 mg, 1.2 mmol), bis(triphenylphosphine)palladium(II) dichloride (14 mg, 0.02 mmol), copper iodide (3 mg, 0.03 mmol) and triphenylphosphine (52 mg, 0.2 mmol) were introduced in a 10 mL microwave vial flushed with argon. This was diluted with anhydrous triethylamine (700 µL, 4 mmol) in anhydrous degased 1,4-dioxane (1.3 mL). The solution was heated under microwave irradiation at 120° C. for 45 min. The reaction mixture was evaporated to dryness in the rotary. The resulting solid was dissolved with diethyl ether and filtrated over a short column of silica. The solution was evaporated, and the resulting yellow oil was purified by flash chromatography (SiO$_2$, ethyl acetate/hexanes 1:1) to give the desired product as a free base. This was dissolved in diethyl ether (5 mL) and hydrogen chloride 1.25M in ethanol (2 mL) was added. The suspension was filtered to recover the hydrochloric salt of the final compound TG010A95 (178 mg, 65%) as a fine yellow powder.

$^1$H COSY NMR (300 MHz, DMSO-d) δ (ppm): 8.92 (d, $^3$J=4.9 Hz, 2H, H α pyrimidine), 7.90-7.70 (m, 6H, H pyrimidine/H alkene), 7.50 (d, $^3$J=4.9 Hz, 1H, H β pyrimidine), 7.45 (m, 3H, H phenyl); $^{13}$C NMR (75.5 MHz, DMSO-d) δ (ppm): 188.7 (C=O), 162.3 (C$_q$ α pyrimidine), 157.7 (CH α pyrimidine), 143.9 (ArCH=), 140.6 (ArCH=), 134.4 (C$_q$ phenyl), 133.3 (CH), 130.8 (CH), 128.9-128.8 (CH phenyl), 125.2 (CH), 121.0 (CH β pyrimidine)

MS(MALDI TOF): m/z=236.8 (M-Cl)$^+$ (1E,4E)-1-phenyl-5-(pyridin-4-yl)penta-1,4-dien-3-one Hydrochloride (TG011A96)

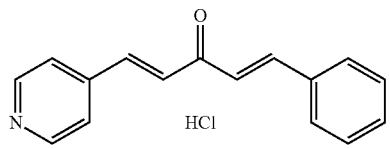 [SMILES: O=C(/C=C/c1ccccc1)/C=C/c1ccncc1 ; Cl]

4-bromopyridine hydrochloride (194 mg, 1 mmol), phenylpent-1-en-4-yn-3-ol (190 mg, 1.2 mmol), bis(triphenylphosphine)palladium(II) dichloride (14 mg, 0.02 mmol), copper iodide (3 mg, 0.03 mmol) and triphenylphosphine (52 mg, 0.2 mmol) were introduced in a 10 mL microwave vial flushed with argon. This was diluted with anhydrous triethylamine (900 µL, 4 mmol) in anhydrous degased 1,4-dioxane (1.1 mL). The solution was heated under microwave irradiation at 120° C. for 45 min. The reaction mixture was diluted with chloroform (15 mL) and extracted with a 1M aqueous solution of hydrochloric acid (3×20 mL). The aqueous was next basified with an aqueous solution of sodium hydroxide (5M, 20 mL). Product was extracted with ethyl acetate (3×40 mL). The combined organic layers were dried over magnesium sulfate, filtered, and evaporated to dryness to give crude product which was purified by flash chromatography (SiO$_2$, 70% ethyl acetate in hexanes) to give the desired product as a free base. This was dissolved in 1,4-dioxane (15 mL) and hydrogen chloride 1.25M in ethanol (2 mL) was added. The suspension was filtered to recover the hydrochloric salt of the final compound TG011A96 (115 mg, 42%) as a fine yellow powder.

$^1$H COSY NMR (300 MHz, DMSO-d) δ (ppm): 8.97 (d, $^3$J=6.4 Hz, 2H, H α pyridine), 8.38 (d, $^3$J=6.4 Hz, 2H, H β pyridine), 8.05-7.85 (m, 3H, alkene), 7.82 (m, 2H, H phenyl), 7.49 (m, 3H, H phenyl), 7.33 (d, $^3$J$_{trans}$=16.8 Hz, 1H, alkene); $^{13}$C NMR (75.5 MHz, DMSO-d) δ (ppm): 188.4 (C=O), 150.2 (C$_q$ α pyridine), 144.8 (CH), 143.0 (CH), 137.0 (CH), 134.4 (C$_q$ phenyl), 133.4 (CH), 131.0 (CH), 129.1-128.7 (CH phenyl), 125.7 (CH), 125.1 (CH)

MS(MALDI TOF): m/z=235.8 (M-Cl)$^+$

Anal. calcd for C$_{16}$H$_{13}$NO.1.1HCl: C, 69.74; H, 5.16; N, 5.08. Found: C, 69.72; H, 5.46; N, 4.86

(1E,4E)-1-phenyl-5-(pyridin-2-yl)penta-1,4-dien-3-one Hydrochloride (TG012A97)

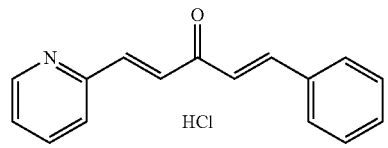 [SMILES: O=C(/C=C/c1ccccc1)/C=C/c1ccccn1 ; Cl]

2-bromopyridine (158 mg, 1 mmol), phenylpent-1-en-4-yn-3-ol (190 mg, 1.2 mmol), bis(triphenylphosphine)palladium(II) dichloride (14 mg, 0.02 mmol), copper iodide (3 mg, 0.03 mmol) and triphenylphosphine (52 mg, 0.2 mmol) were introduced in a 10 mL microwave vial flushed with argon. This was diluted with anhydrous triethylamine (700 µL, 4 mmol) in anhydrous degased 1,4-dioxane (1.3 mL). The solution was heated under microwave irradiation at 120° C. for 45 min. The reaction mixture was diluted with chloroform (15 mL) and extracted with a 3M aqueous solution of hydrochloric acid (3×20 mL). The aqueous was next basified with an aqueous solution of sodium hydroxide 6M until pH≈10. Product was extracted with ethyl acetate (3×50 mL). The combined organic layers were dried over magnesium sulfate, filtered, and evaporated to dryness to give crude product which was purified by flash chromatography (SiO$_2$, 30% ethyl acetate in hexanes) to give the desired product as a free base. This was dissolved in diethyl ether (5 mL) and hydrogen chloride 1.25M in ethanol (2 mL) was added. The suspension was filtered to recover the hydrochloric salt of the final compound TG012A97 (82 mg, 30%) as a fine yellow powder.

$^1$H COSY NMR (300 MHz, DMSO-d) δ (ppm): 8.83 (d, $^3$J=5.6 Hz, 1H, H α pyridine), 8.38-8.26 (m, 2H, H β pyridine), 8.09 (d, $^3$J$_{trans}$=16.4 Hz, 1H, CH alkene), 7.99 (d, $^3$J$_{trans}$=15.9 Hz, 1H, CH alkene), 7.84 (d, $^3$J$_{trans}$=16.4 Hz, 1H, CH alkene), 7.84-7.81 (m, 1H, H β pyridine), 7.81 (m, 2H, H phenyl), 7.47 (m, 3H, H phenyl), 7.29 (d, $^3$J$_{trans}$=15.9 Hz, 1H, CH alkene); $^{13}$C NMR (75.5 MHz, DMSO-d) δ (ppm): 188.2 (C=O), 149.5 (C$_q$ α pyridine), 145.5 (CH), 144.7 (CH), 142.6 (CH), 135.7 (C$_q$ phenyl), 134.4 (CH), 131.5 (CH), 130.9 (CH), 129.1-128.8 (CH phenyl), 126.3 (CH), 126.0-125.9 (CH)

MS(EI): m/z=235

Anal. calcd for C$_{16}$H$_{13}$NO.1HCl: C, 70.72; H, 5.19; N, 5.15. Found: C, 70.47; H, 5.33; N, 5.03

EXAMPLE 5

Synthesis of 2,6-diaryl-4-piperidones

To generate the 2,6-diaryl-4-piperidones NW246.1 and NW249.1, a Michael addition-cyclization sequence was performed with the corresponding dibenzylidene acetones NW247 and NW275 prepared in example 1 and an excess of base (e.g. triethylamine) in 2-3 days at room temperature (Scheme 8, route A).

Compound NW249.1 was also prepared in a two-step synthesis. In the first step, 2 equivalents of the benzaldehyde and 1 equivalent of acetone and ammonium acetate were allowed to react in a Michael addition-cyclization sequence to form the 4-piperidone ring. In the second step, the secondary amine attached to the ring is alkylated with methyl iodide in acetone under basic conditions for 3.5 h at 45-55° C. (Scheme 8, route B).

Scheme 8: Synthesis of 2,6-diaryl-4-piperidones via two different routes.

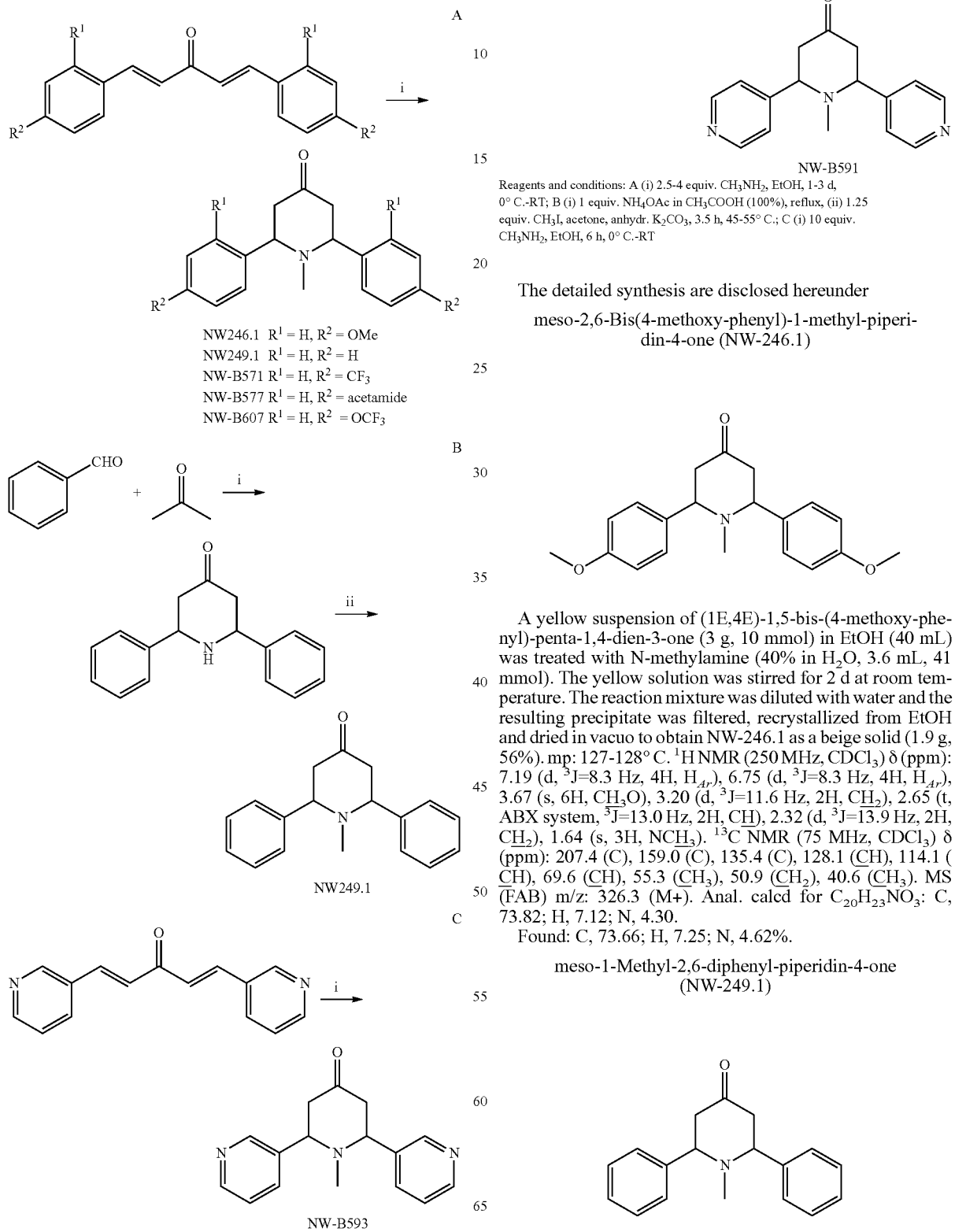

Reagents and conditions: A (i) 2.5-4 equiv. CH₃NH₂, EtOH, 1-3 d, 0° C.-RT; B (i) 1 equiv. NH₄OAc in CH₃COOH (100%), reflux, (ii) 1.25 equiv. CH₃I, acetone, anhydr. K₂CO₃, 3.5 h, 45-55° C.; C (i) 10 equiv. CH₃NH₂, EtOH, 6 h, 0° C.-RT The detailed synthesis are disclosed hereunder meso-2,6-Bis(4-methoxy-phenyl)-1-methyl-piperidin-4-one (NW-246.1)

A yellow suspension of (1E,4E)-1,5-bis-(4-methoxy-phenyl)-penta-1,4-dien-3-one (3 g, 10 mmol) in EtOH (40 mL) was treated with N-methylamine (40% in H₂O, 3.6 mL, 41 mmol). The yellow solution was stirred for 2 d at room temperature. The reaction mixture was diluted with water and the resulting precipitate was filtered, recrystallized from EtOH and dried in vacuo to obtain NW-246.1 as a beige solid (1.9 g, 56%). mp: 127-128° C. ¹H NMR (250 MHz, CDCl₃) δ (ppm): 7.19 (d, ³J=8.3 Hz, 4H, H$_{Ar}$), 6.75 (d, ³J=8.3 Hz, 4H, H$_{Ar}$), 3.67 (s, 6H, CH₃O), 3.20 (d, ³J=11.6 Hz, 2H, CH₂), 2.65 (t, ABX system, ³J=13.0 Hz, 2H, CH), 2.32 (d, ³J=13.9 Hz, 2H, CH₂), 1.64 (s, 3H, NCH₃). ¹³C NMR (75 MHz, CDCl₃) δ (ppm): 207.4 (C), 159.0 (C), 135.4 (C), 128.1 (CH), 114.1 (CH), 69.6 (CH), 55.3 (CH₃), 50.9 (CH₂), 40.6 (CH₃). MS (FAB) m/z: 326.3 (M+). Anal. calcd for C₂₀H₂₃NO₃: C, 73.82; H, 7.12; N, 4.30.
Found: C, 73.66; H, 7.25; N, 4.62%.

meso-1-Methyl-2,6-diphenyl-piperidin-4-one (NW-249.1)

A yellow solution of (1E,4E)-1,5-diphenyl-penta-1,4-dien-3-one (5 g, 21 mmol) in EtOH (50 mL) was treated with N-methylamine (40% in H$_2$O, 4.7 mL, 53 mmol). The reaction mixture was stirred for 2 d at ambient temperature. The solution was diluted with water and the resulting white precipitate was filtered, recrystallized from EtOH and dried in vacuo to obtain NW-249.1 as a white solid (4.1 g, 73%). mp: 138-140° C. $^1$H NMR (250 MHz, CDCl$_3$) δ (ppm): 7.69-7.31 (m, 10H, H$_{Ar}$), 3.46 (d, $^3$J=11.9 Hz, 2H, C$\underline{H}_2$), 2.85 (t, ABX system, $^3$J=12.9 Hz, 2H, C$\underline{H}$), 2.53 (d, $^3$J=14.5 Hz, 2H, C$\underline{H}_2$), 1.85 (s, 3H, NC$\underline{H}_3$). $^{13}$C NMR (75 MHz, CD$_3$OD) δ (ppm): 136.5 (C), 130.9 ($\underline{C}$H), 130.4 ($\underline{C}$H), 129.1 ($\underline{C}$H), 99.1 ($\underline{C}$H$_3$), 37.5 ($\underline{C}$H$_2$).

MS (FAB) m/z: 266.2 (M+). Anal. calcd for C$_{18}$H$_{19}$NO: C, 81.47; H, 7.22; N, 5.28. Found: C, 81.45; H, 7.15; N, 5.19%.

2,6-Bis(4-trifluoromethyl)phenyl)-1-methyl-piperidin-4-one (NW-B571)

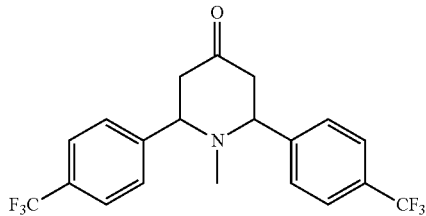 [SMILES: CN1C(c2ccc(C(F)(F)F)cc2)CC(=O)CC1c1ccc(C(F)(F)F)cc1]

A yellow solution of (1E,4E)-1,5-bis-(4-trifluoromethylphenyl)-penta-1,4-dien-3-one (500 mg, 1.4 mmol) in EtOH (4 mL) was treated with N-methylamine (40% in H$_2$O, 471 μL, 5.4 mmol). The reaction mixture was stirred for 30 h at room temperature in the dark. The mixture was diluted with water and extracted with CH$_2$Cl$_2$. The combined organic layers were dried with MgSO$_4$, filtered and evaporated in vacuo. The crude residue was purified by flash-chromatography on silica gel (Hexane/EtOAc 2:1) to obtain NW-B571 as a pale yellow solid (219 mg, 41%) (note: mixture of cis/trans isomers in a ratio of 2:1). mp: 105-107° C. $^1$H NMR (300 MHz, CD$_3$OD) δ (ppm): 7.67 (s, 8 H, H$_{Ar}$), 3.56 (d, $^3$J=12.0 Hz, J=2.6 Hz, 1 H, C$\underline{H}_2$), 3.49 (d, $^3$J=12.0 Hz, 1 H, C$\underline{H}_2$), 2.05 (t, J=13.9 Hz, 2 H, C$\underline{H}$), 1.91-1.77 (m, 2 H, C$\underline{H}_2$), 1.78 (d, J=3.7 Hz, 3 H, C$\underline{H}_3$). Signals of the minor isomer: 7.72 (s, 8 H, H$_{Ar}$), 3.66 (dd, $^3$J=12.0 Hz, J=2.6 Hz, 2 H, C$\underline{H}_2$), 2.94 (t, $^3$J=13.0 Hz, 2 H, C$\underline{H}$), 2.46 (d, $^3$J=14.1 Hz, 2 H, C$\underline{H}_2$), 1.84 (s, 3 H, C$\underline{H}_3$). $^{13}$C NMR (75 MHz, CD$_3$OD) δ (ppm): 207.9 (C), 150.9 ($\underline{C}$), 130.9 (q, $^2$J(C, F)=32.6 Hz, C), 129.5 ($\underline{C}$H), 128.0 (C), 127.0 (q, $^3$J(C, F)=3.6 Hz, $\underline{C}$H), 68.6 ($\underline{C}$H), 46.7 ($\underline{C}$H$_2$), 42.2 ($\underline{C}$H$_3$). Signals of the minor isomer: 207.9 (C), 149.5 (C), 130.9 (q, $^2$J(C, F)=32.6 Hz, C), 129.5 ($\underline{C}$H), 127.3 (q, $^3$J(C, F)=3.7 Hz, $\underline{C}$H), 124.4 (C), 68.2 ($\underline{C}$H), 46.1 ($\underline{C}$H$_2$), 42.2 ($\underline{C}$H$_3$). MS (FAB) m/z: 402.2 (M+). Anal. calcd for C$_{20}$H$_{17}$F$_6$NO: C, 59.85; H, 4.27; N, 3.49. Found: C, 60.02; H, 4.40; N, 3.52%.

meso-2,6-Bis(4-acetamido-phenyl)-1-methyl-piperidin-4-one (NW-B577)

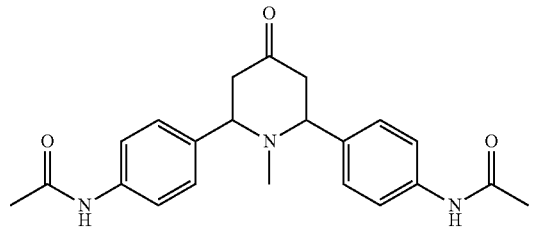 [SMILES: CC(=O)Nc1ccc(C2CC(=O)CC(c3ccc(NC(C)=O)cc3)N2C)cc1]

A yellow suspension of N-{4-[(1E,4E)-5-(4-acetylaminophenyl)-3-oxo-penta-1,4-dienyl]-phenyl}-acetamide (800 mg, 2.3 mmol) in EtOH (9 mL) was treated with N-methylamine (40% in H$_2$O, 803 μL, 9.2 mmol). The reaction mixture was stirred for overnight at room temperature in the dark. The reaction mixture was diluted with water (12 mL) and the resulting precipitate was filtered, recrystallized from EtOH and dried in vacuo to obtain NW-B577 as a pale yellow solid (831 mg, 95%). mp: 234-237° C. $^1$H NMR (300 MHz, DMSO-d$_6$) δ (ppm): 9.94 (s, 2H, N$\underline{H}$), 7.57 (d, $^3$J=8.4 Hz, 4H, H$_{Ar}$), 7.36 (d, $^3$J=8.4 Hz, 4H, H$_{Ar}$), 3.43-3.34 (m, 2H, C$\underline{H}_2$), 2.87 (t, ABX system, $^3$J=13.0 Hz, 2H, C$\underline{H}$), 2.25 (d, $^3$J=14.1 Hz, 2H, C$\underline{H}_2$), 2.03 (s, 6H, COC$\underline{H}_3$), 1.67 (s, 3H, NC$\underline{H}_3$). $^{13}$C NMR (75 MHz, DMSO-d$_6$) δ (ppm): 206.6 (C), 168.6 (C), 138.9 (C), 138.2 (C), 127.7 ($\underline{C}$H), 119.7 ($\underline{C}$H), 68.7 ($\underline{C}$H), 50.1, 24.3.

MS (FAB) m/z: 380.3 (M+). Anal. calcd for C$_{22}$H$_{25}$N$_3$O$_3$ C.0.2H$_2$O: 68.98; H, 6.68; N, 10.97. Found: C, 68.85; H, 6.92; N, 11.26%.

1-Methyl-2,6-di(pyridine-3-yl)piperidin-4-one (NW-B593)

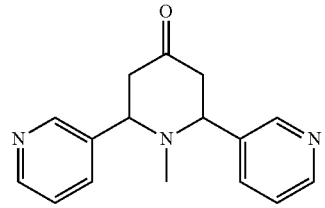 [SMILES: CN1C(c2cccnc2)CC(=O)CC1c1cccnc1]

A suspension of (1E,4E)-1,5-di(pyridin-3-yl)penta-1,4-dien-3-one (1 g, 3.2 mmol) in DMF (10 mL) was treated with N-methylamine (40% in H$_2$O, 2.8 mL, 32 mmol) at 0° C. The solution was stirred for 6 h at 0° C. The reaction mixture was poured into ice-water (150 mL) and was extracted with DCM. The combined organic layers were dried with MgSO$_4$, filtered and evaporated in vacuo. The crude product was purified by flash-chromatography (CH$_2$Cl$_2$/MeOH 9:1) to obtain NW-B593 as a bright yellow solid (814 mg, 94%). mp: 103-106° C. $^1$H NMR (300 MHz, CDCl$_3$) δ (ppm): 8.67 (d, $^4$J=1.8 Hz, 2H, H$_{Ar}$), 8.59 (dd, $^3$J=4.8 Hz, $^4$J=1.6 Hz, 2H, H$_{Ar}$), 7.85 (d, $^3$J=7.9 Hz, 2H, H$_{Ar}$), 7.37 (dd, $^3$J=7.9 Hz, $^3$J=4.8 Hz, 2H, H$_{Ar}$), 3.58 (dd, $^3$J=12.0 Hz, J=2.8 Hz, 2H, C$\underline{H}_2$), 2.84 (t, $^3$J=13.0 Hz, 2H, C$\underline{H}$), 2.55 (dd, $^3$, J=13.9 Hz, J=1.8 Hz, 2H, C$\underline{H}_2$), 1.64 (s, 3H, C$\underline{H}_3$). $^{13}$C NMR (75 MHz, CDCl$_3$) δ (ppm): 204.9 (C), 149.4 ($\underline{C}$H), 148.8 ($\underline{C}$H), 138.1 (C), 134.8 ($\underline{C}$H), 124.1 ($\underline{C}$H), 67.5 ($\underline{C}$H), 50.2 ($\underline{C}$H$_2$), 41.0 ($\underline{C}$H$_3$). MS (FAB) m/z: 268.2 (M+). Anal. calcd for C$_{16}$H$_{17}$N$_3$O.0.3H$_2$O: C, 70.46; H, 6.50; N, 15.41. Found: C, 70.45; H, 6.38; N, 15.32%.

1-Methyl-2,6-di(pyridine-4-yl)piperidin-4-one (NW-B591)

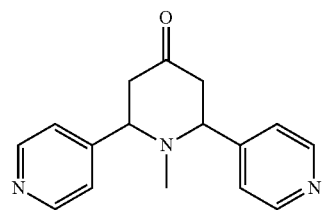 [SMILES: CN1C(c2ccncc2)CC(=O)CC1c1ccncc1]

A suspension of (1E,4E)-1,5-di(pyridin-4-yl)penta-1,4-dien-3-one (1 g, 3.2 mmol) in DMF (10 mL) was treated with N-methylamine (40% in $H_2O$, 2.8 mL, 32 mmol) at 0° C. The solution was warmed up to ambient temperature and stirred for 6 h at RT. The reaction mixture was poured into ice-water and the resulting precipitate was filtered. The aqueous solution was extracted with DCM and the combined organic layers were dried with $MgSO_4$, filtered and evaporated in vacuo. The crude product was purified by flash-chromatography ($CH_2Cl_2$/MeOH 9:1) to obtain NW-B591 as a bright yellow solid (417 mg, 48%) (note: mixture of cis/trans isomers in a ratio of 4:1). mp: 103-106° C. $^1$H NMR (300 MHz, $CDCl_3$) δ (ppm): 8.65 (dd, $^4J$=4.5 Hz, $^3J$=1.5 Hz, 4 H, $H_{Ar}$), 7.42 (dd, $^3J$=4.5 Hz, $^4J$=1.6 Hz, 4 H, $H_{Ar}$), 3.51 (dd, $^3J$=12.0 Hz, J=3.2 Hz, 2 H, $CH_2$), 2.82-2.68 (m, 2 H, $CH$), 2.57-2.46 (m, 2 H, $CH_2$), 1.89 (s, 3 H, $CH_3$). Signals of the minor isomer: 8.65-8.60 (m, 4 H, $H_{Ar}$), 7.25 (dd, $^3J$=4.7 Hz, $^4J$=1.5 Hz, 4 H, $H_{Ar}$), 4.13 (t, $^3J$=6.0 Hz, 2 H, $CH$), 2.96-2.86 (m, 2 H, $CH_2$), 2.86 (ddd, J=7.9, J=6.0 Hz, J=1.2 Hz, 2 H, $CH_2$), 2.19 (s, 3 H, $CH_3$). $^{13}$C NMR (75 MHz, $CDCl_3$) δ (ppm): 204.3 (C), 151.6 (C), 150.4 (CH), 122.2 (CH), 68.9 (CH), 49.6 ($CH_2$), 41.1 ($CH_3$).

Signals of the minor isomer: 206.6 (C), 150.8 (CH), 148.7 (C), 123.0 (CH), 61.8 (CH), 43.3 ($CH_2$), 38.2 ($CH_3$). MS (FAB) m/z: 268.2 (M+). Anal. calcd for $C_{16}H_{17}N_3O \cdot 0.5H_2O$: C, 69.54; H, 6.57; N, 15.21. Found: C, 69.43; H, 6.49; N, 14.94%.

1-Methyl-2,6-bis(4-(trifluoromethoxy)phenyl)piperidin-4-one (NW-B607)

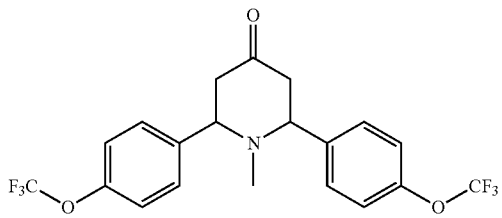 [SMILES: CN1C(c2ccc(OC(F)(F)F)cc2)CC(=O)CC1c1ccc(OC(F)(F)F)cc1]

A suspension of (1E,4E)-1,5-di(pyridin-4-yl)penta-1,4-dien-3-one (1 g, 2.5 mmol) in DMF (10 mL) was treated with N-methylamine (40% in $H_2O$, 2.4 mL, 25 mmol) at 0° C. The solution was stirred for 1d at 0° C. The reaction mixture was poured into ice-water (200 mL) and the aqueous solution was extracted with EtOAC and the combined organic layers were dried with $MgSO_4$, filtered and evaporated in vacuo. The crude product was purified by flash-chromatography (Hexane/$Et_2O$ 4:1) to obtain NW-B607 as a brown syrup (123 mg, 11%).

$^1$H NMR (300 MHz, $CDCl_3$) δ (ppm): 7.49-7.34 (m, 4 H, $H_{Ar}$), 7.15 (d, $^3J$=8.2 Hz, 4 H, $H_{Ar}$), 3.51 (dd, $^3J$=9.4 Hz, 2 H, $CH_2$), 2.78-2.61 (m, 2 H, $CH$), 2.43 (d, $^3J$=13.5 Hz, 2 H, $CH_2$), 1.75 (s, 3 H, $CH_3$). $^{13}$C NMR (75 MHz, $CDCl_3$) δ (ppm): 205.9 (C), 148.7 (C), 141.6 (C), 128.4 (CH), 121.5 (CH), 120.5 (CH, J=253.7 Hz), 69.3 (CH), 50.6 ($CH_2$), 40.8 ($CH_3$). MS (FAB) m/z: 432.2 (M+). Anal. calcd for $C_{20}H_{17}F_6NO_3$: C, 55.43; H, 3.95; N, 3.23. Found: C, 55.20; H, 3.97; N, 2.92%.

EXAMPLE 6

Synthesis of 2,6-diaryldihydro-2H-thiopyran-4-one and Relative Sulfur-oxidized Species for Their Use as Prodrugs of Dibenzylidene Acetones With the goal to optimize the pharmacological properties of the dibenzylidene acetones, the synthesis and biological evaluation of 2,6-diaryldihydro-2H-thiopyran-4-one and relative sulfur-oxidized species has been considered.

At first, the synthesis of the 2,6-diaryldihydro-2H-thiopyran-4-one can be achieved through a double Michael addition of sulfur on the parent dibenzylidene acetones described in examples 1 and 2. This reaction occurred in basic conditions with the use of sodium hydrosulfide in aqueous (routes A and B) or organic media (route C) (Scheme 9).

Scheme 9: Synthesis of 2,6-diaryldihydro-2H-thiopyran-4-one.

Route A

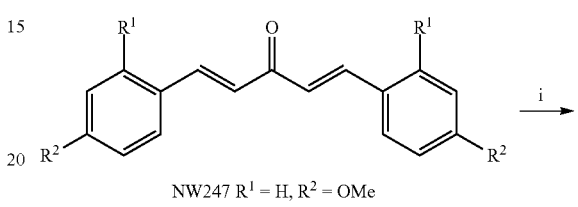

NW247 $R^1$ = H, $R^2$ = OMe
NW268 $R^1$ = Cl, $R^2$ = H
NW308 $R^1$ = H, $R^2$ = Cl

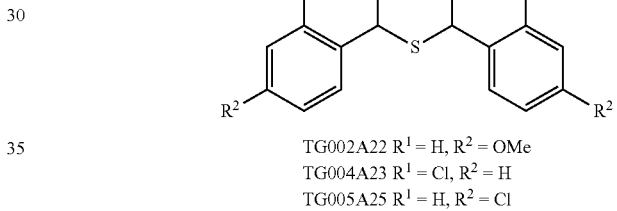

TG002A22 $R^1$ = H, $R^2$ = OMe
TG004A23 $R^1$ = Cl, $R^2$ = H
TG005A25 $R^1$ = H, $R^2$ = Cl

Route B

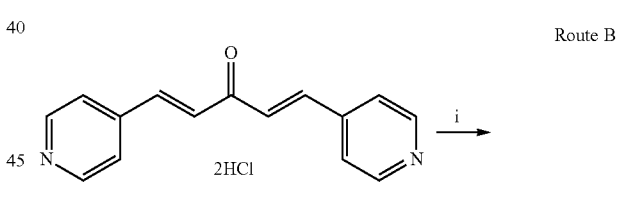

NW319

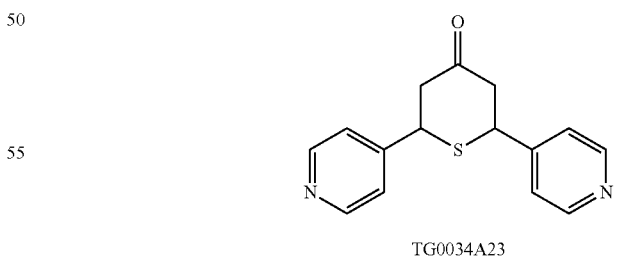

TG0034A23

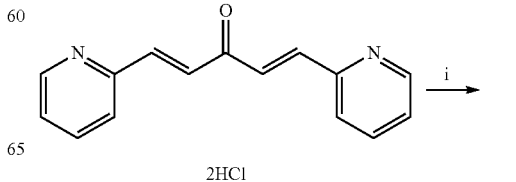

2HCl

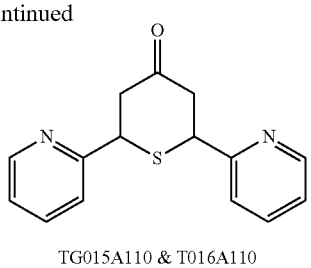

TG015A110 & T016A110

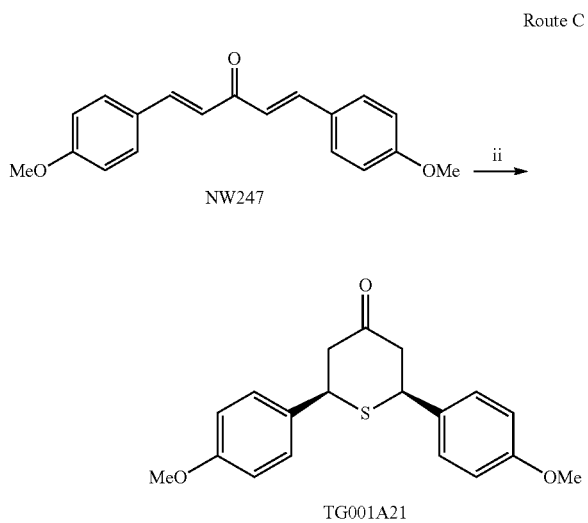

Route C

NW247

TG001A21

Reagents and conditions: (i) NaHS•xH2O 2-4 equiv, K2HPO4 1.2M, Acetone, 15-24 h, RT; (ii) NaHS•xH2O 2-4 equiv, DCM, MeOH, piperidine, 2 h, reflux Next, the effect of sulfur oxidation has been harvested. This implied the synthesis of sulfoxide and sulfone derivatives from the 2,6-diaryldihydro-2H-thiopyran-4-one described upper. Sulfone could be easily obtained from the over-oxidation of the sulfur atom with, for example, meta-chloroperbenzoic acid (m-CPBA) (scheme 10).

Scheme 10: Synthesis of sulfone derivatives

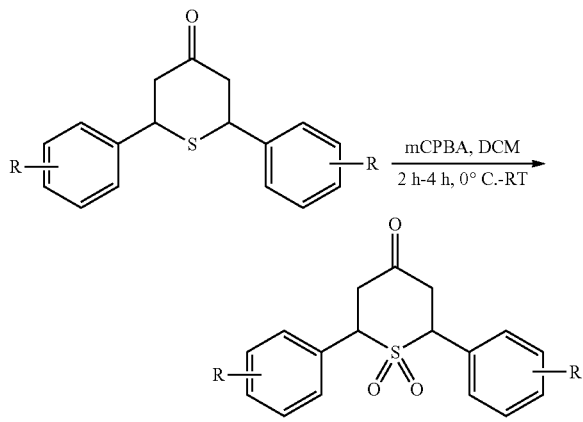

Regarding the synthesis of sulfoxide, several synthetic pathways have been studied. A strictly monitored amount of mCPBA might be used for the synthesis of these sulfoxides. However, we found that in our case, the risk of over-oxidation was too high; in addition, with this kind of methodology the stereocontrol of the reaction was very limited. Thus, it is preferable to use some more controlled and less drastic conditions. These include, but are not limited to, the use of hydroperoxide (tert-butylhydroperoxide or preferentially cumyl hydroperoxide) in presence of metal complex (titanium(IV) or vanadium(V)) and eventually (but not necessarily) a chiral modifier—such as enantiopure diethyl tartrate or BINOL derivatives.

The detailed syntheses of all these sulfur and oxidized sulfur derivatives are disclosed hereunder.

General Procedure i (Routes A and B)

Sodium hydrosulfide hydrate (115 mg, 2 eq) was dissolved in a mixture of a 1.2 M aqueous solution of potassium phosphate dibasic (2 mL) and acetone (4 mL). To this was added the appropriate dibenzylidene acetone (for example NW247 (220 mg, 0.75 mmol)). The reaction mixture was stirrired at room temperature for 15 h to 24 h (until completion upon TLC). Water (10 mL) was subsequently added to precipitate the desired product. The suspension was filtered and the crude was dried in vacuo and, if necessary, recrystallized to give the final compound.

General Procedure ii (Routes C)

Sodium hydrosulfide hydrate (1.0 g, 2 eq) was dissolved in methanol (25 mL). To this was added the appropriate dibenzylidene acetone (for example NW247 (2.0 g, 6.79 mmol)) solubilized in dichloromethane (25 mL). The resulting solution was refluxing for 2 hours under vigorous stirring. The reaction mixture was then poured in a 1M aqueous solution of hydrochloric acid (20 mL) and extracted with dichloromethane (3×25 mL). The combined organic layers were dried over magnesium sulfate, filtered, and evaporated to dryness to give crude product which can be recrystallized (for example in acetonitrile) to give the final pure compound.

cis-2,6-bis(4-methoxyphenyl)dihydro-2H-thiopyran-4(3H)-one (TG001A21)

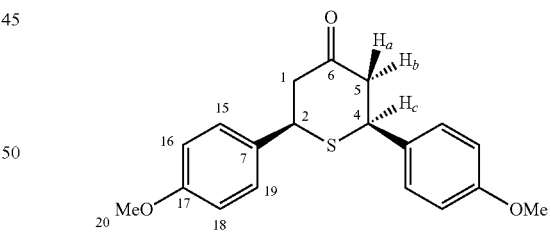

According to general procedure ii, desired pure product TG001A21 was obtained as a white powder (1.7 g, 77%, de>90%). mp: 166-169° C.

$^1$H NMR (300 MHz, CDCl$_3$) δ (ppm): 7.32 (d, $^3$J=8.9 Hz, 4H, ArH), 6.9 (d, $^3$J=8.6 Hz, 4H, ArH), 4.28 (dd, J=11.8 Hz, 3.3 Hz, 2H, H$_c$), 3.81 (s, 6H, OCH$_3$), 3.17-2.98 (m, 4H, H$_a$/H$_b$)

$^{13}$C NMR (75.5 MHz, CDCl$_3$) δ (ppm): 208.3 (C6=O), 159.3 (C17), 131.6 (C7), 128.3 (C15-C19), 114.2 (C16-C18), 55.5 (—OCH$_3$), 50.8 (C1-C5), 47.9 (C2-4)

MS(FAB+): m/z=329.1 trans-2,6-bis(4-methoxyphenyl)dihydro-2H-thiopyran-4(3H)-one (TG002A22)

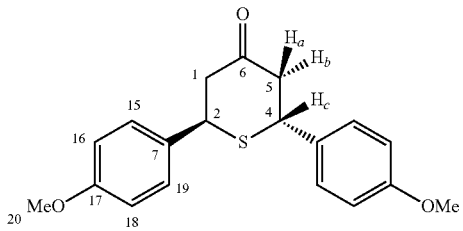

According to general procedure i, desired pure product TG002A22 was obtained as a white powder (510 mg, 78%, de>90%). mp: 144-147° C.

$^1$H NMR (300 MHz, CDCl$_3$) δ (ppm): 7.28 (d, $^3$J=7.8 Hz, 4H, ArH), 6.87 (d, $^3$J=7.8 Hz, 4H, ArH), 4.30 (m, 2H, H$_c$), 3.81 (s, 6H, OCH$_3$), 3.17-2.98 (m, 4H, H$_a$/H$_b$)

$^{13}$C NMR (75.5 MHz, CDCl$_3$) δ (ppm): 209.1 (C6=O), 159.1 (C17), 132.6 (C7), 128.8 (C15-C19), 114.2 (C16-C18), 55.5 (—OCH$_3$), 49.0 (C1-C5), 43.5 (C2-C4)

MS(FAB+): m/z=329.1 trans-2,6-di(pyridin-4-yl)dihydro-2H-thiopyran-4(3H)-one (TG003A23)

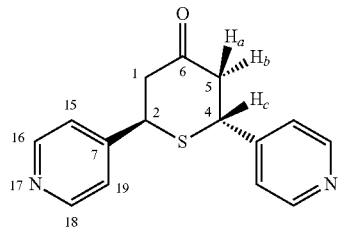

According to general procedure i, desired pure product TG003A23 was obtained as a white powder (80 mg, 39%, de≈80%). mp: 127-129° C.

$^1$H NMR (300 MHz, CDCl$_3$) δ (ppm): 8.52 (d, $^3$J=5.6 Hz, 4H, ArH), 7.49 (d, $^3$J=5.6 Hz, 4H, ArH), 4.4 (m, 2H, H$_c$), 2.5-2.0 (m, 4H, H$_a$/H$_b$)

$^{13}$C NMR (75.5 MHz, CDCl$_3$) δ (ppm): 200.1 (C=O), 150.0 (C7), 149.8 (C16-C18), 122.5 (C15-C19), 45.0 (C1-C5), 44.3 (C2-C4)

MS(EI+): m/z=270.1 cis-2,6-bis(2-chlorophenyl)dihydro-2H-thiopyran-4(3H)-one (TG004A23)

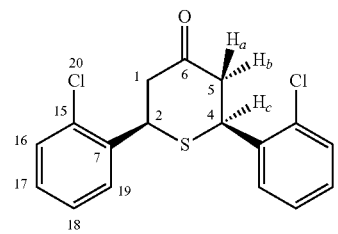

According to general procedure i, desired pure product TG004A23 was obtained as a white powder (180 mg, 72%, de=60%). mp: 91-94° C.

$^1$H NMR (300 MHz, CDCl$_3$) δ (ppm): 7.55 (d, $^3$J=7.6 Hz, 2H, Ar), 7.41 (t, $^3$J=8.6 Hz, 2H, Ar), 7.35-7.25 (m, 4H, Ar), 4.89 (dd, J=10.9 Hz, 3.6 Hz, 2H, H$_c$), 3.15-2.9 (m, 4H, H$_a$/H$_b$)

Signals of the minor diastereoisomer: 7.55 (d, $^3$J=7.6 Hz, 2H, Ar), 7.41 (t, $^3$J=8.6 Hz, 2H, Ar), 7.35-7.25 (m, 4H, Ar), 4.82 (t, J=6.6 Hz, 2H, H$_c$), 3.15-2.9 (m, 4H, H$_a$/H$_b$)

$^{13}$C NMR (75.5 MHz, CDCl$_3$) δ (ppm): 206.1 (C=O), 136.8 (C7), 132.3 (C15), 129.8 (CH), 129.6 (CH), 128.5 (CH), 127.9 (CH), 48.3 (C1-C5), 42.8 (C2-C4)

MS(FAB+): m/z=337.0

Anal. calcd for C$_{17}$H$_{14}$Cl$_2$OS C, 60.54; H, 4.18; S 9.30; Cl, 20.87. Found: C, 60.52; H, 4.23; S 9.30; Cl, 20.87

2,6'-bis(4-ohlorophenyl)dihydro-2H-thiopyran-4(3H)-one (TG005A25)

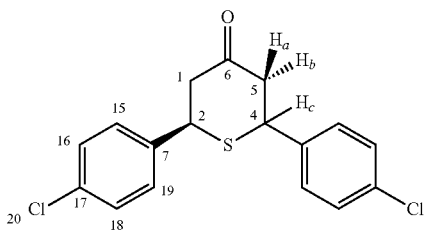

According to general procedure i, desired pure product TG005A25 was obtained as a white powder (219 mg, 87%, de=0%). mp: 131-133° C.

$^1$H NMR (300 MHz, CDCl$_3$) δ (ppm): 7.37-7.27 (m, 8H, Ar), 4.32 (bd, J=4.5 Hz, 2H, H$_c$ cis), 4.28 (bm, 2H, H$_c$ trans), 3.2-2.9 (m, 4H, H$_a$/H$_b$ cis/trans)

$^{13}$C NMR (75.5 MHz, CDCl$_3$) δ (ppm): signal for the cis isomer: 206.9 (C6=O), 137.7 (C7), 134.1 (C17), 129.2 (C15-C19), 128.6 (C16-C18), 50.3 (C1-C5), 47.8 (C2-C4) signal for the trans isomer: 207.6 (C6=O), 138.6 (C7), 133.6 (C17), 128.9 (C15-C19), 128.8 (C16-C18), 48.4 (C1-C5), 43.4 (C2-C4)

MS(EI): m/z=337.0 trans-2,6-di(pyridin-2-yl)dihydro-2H-thiopyran-4(3H)-one (TG015A110) and Cis-2,6-di(pyridin-2-yl)dihydro-2H-thiopyran-4(3H)-one (TG016A110)

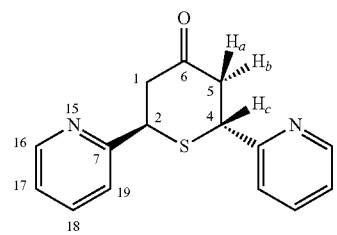

TG015A110

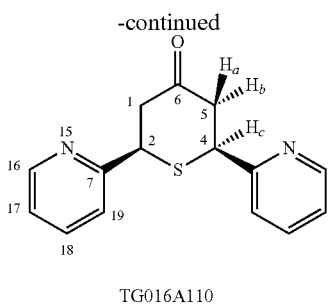

TG016A110

According to general procedure i, these two product were isolated and purified after a flash chromatography (SiO$_2$, ethyl acetate/cyclohexane 1:1) to give desired pure diastereoisomer trans TG015A110 (608 mg, 47%, de=100%) and pure diastereoisomer cis TG016A110 (225 mg, 17%, de=100%), booth as a white powder.

NMR analysis for the trans isomer TG015A110:
$^1$H NMR (300 MHz, CDCl$_3$) δ (ppm): 8.54 (d, $^3$J=4.2 Hz, 2H, H16), 7.64 (dt, J$_t$=7.7 Hz, J$_d$=1.8 Hz, 2H, H18), 7.26 (m, 2H, H19), 7.19 (m, 2H, H17), 4.59 (m, 2H, H$_c$), 3.10 (m, 4H, H$_a$/H$_b$)
$^{13}$C NMR (75.5 MHz, CDCl$_3$) δ (ppm): 206.9 (C6=O), 159.8 (C7), 149.1 (C16), 136.9 (C18), 122.4-122.2 (C19/C17), 47.0 (C1-C5), 45.6 (C2-C4)

NMR analysis for the cis isomer TG016A110:
$^1$H NMR (300 MHz, CDCl$_3$) δ (ppm): 8.59 (d, $^3$J=4.8 Hz, 2H, H16), 7.68 (dt, J$_t$=7.7 Hz, J$_d$=1.8 Hz, 2H, H18), 7.37 (m, 2H, H19), 7.20 (m, 2H, H17), 4.54 (dd, $^3$J$_{Hc-Ha}$=12.3 Hz, $^3$J$_{Hc-Hb}$=2.6 Hz, 2H, H$_c$), 3.36-3.21 (m, 2H, H$_a$), 3.02 (dd, $^2$J$_{Hb-Ha}$=14.2 Hz, $^3$J$_{Hb-Hc}$=2.6 Hz, 2H, H$_b$)
$^{13}$C NMR (75.5 MHz, CDCl$_3$) δ (ppm): 208.3 (C6=O), 157.9 (C7), 149.7 (C16), 137.0 (C18), 122.9-122.3 (C19/C17), 49.7 (C2-C4), 48.6 (C1-C5)
MS(EI): m/z=270.1 cis-2,6-bis(4-methoxyphenyl)dihydro-2H-thiopyran-4(3H)-one 1,1-dioxide (TG014A103)

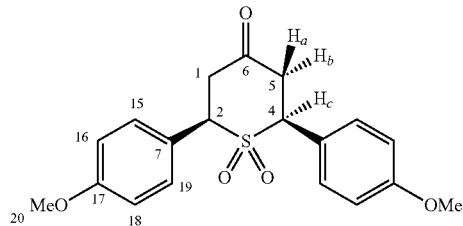

cis-2,6-bis(4-methoxyphenyl)dihydro-2H-thiopyran-4(3H)-one (TG001A21) (329 mg, 1 mmol) was dissolved in dichloromethane (4 mL). This solution was cooled to 0° C. and a solution of mCPBA (382 mg, 2.2 mmol) in dichloromethane (3 mL) was added dropwise. The reaction was kept at 0° C. under stirring for 1 h30 and next allowed to warm at room temperature. Reaction was carried on at RT for another one hour and half. The reaction mixture was evaporated to dryness and the residue was dissolved in ethyl acetate (20 mL). This organic phase was washed successively with saturated Na$_2$S$_2$O$_3$ (10 mL), saturated sodium hydrogencarbonate (10 mL) and brine (10 mL). The organic layer was dried over magnesium sulfate, filtered, and evaporated to dryness to give crude product which was purified by flash chromatography (SiO$_2$, ethyl acetate/cyclohexane 1:1) to give the desired final compound TG014A103 (115 mg, 32%, de=80%) as a white powder.

$^1$HNMR (300 MHz, CDCl$_3$) δ (ppm): 7.35 (d, $^3$J=9.1 Hz, 4H, ArH), 6.9 (d, $^3$J=9.1 Hz, 4H, ArH), 4.47 (dd, $^3$J$_{Hc-Ha}$=14.2 Hz, $^3$J$_{Hc-Hb}$=2.4 Hz, 2H, H$_c$), 3.81 (s, 6H, OCH$_3$), 3.68 (t, J$_{Ha-(Hc/Hb)}$=14.2 Hz, 2H, H$_a$), 2.93 (bd, $^2$J$_{Hb-Ha}$=14.2 Hz, 2H, H$_b$)

$^{13}$C NMR (75.5 MHz, CDCl$_3$) δ (ppm): 202.5 (C6=O), 160.9 (C17), 130.9 (C15-C19), 120.5 (C7), 114.7 (C16-C18), 64.0 (C2-C4), 55.5 (—OCH$_3$), 46.2 (C1-C5)

MS(EI): m/z=360.1

EXAMPLE 7

Synthesis of the Primary Starting Materials for the Synthesis of Dibenzylidene Acetones and Relative Derivatives The diversity on the dibenzylidene acetones can be obtaine with the use of highly substituted salicaldehyde of the following general structure R = H, Me
X = H, Br
Z = H, Me, OMe, SMe For examples from those disclosed in table II.

TABLE II

| 4-Z = Me | 4-Z = Me | 4-Z = SMe | 4-Z = OMe |
|---|---|---|---|

TABLE II-continued

| 4-Z = Me | 4-Z = Me | 4-Z = SMe | 4-Z = OMe |
|---|---|---|---|

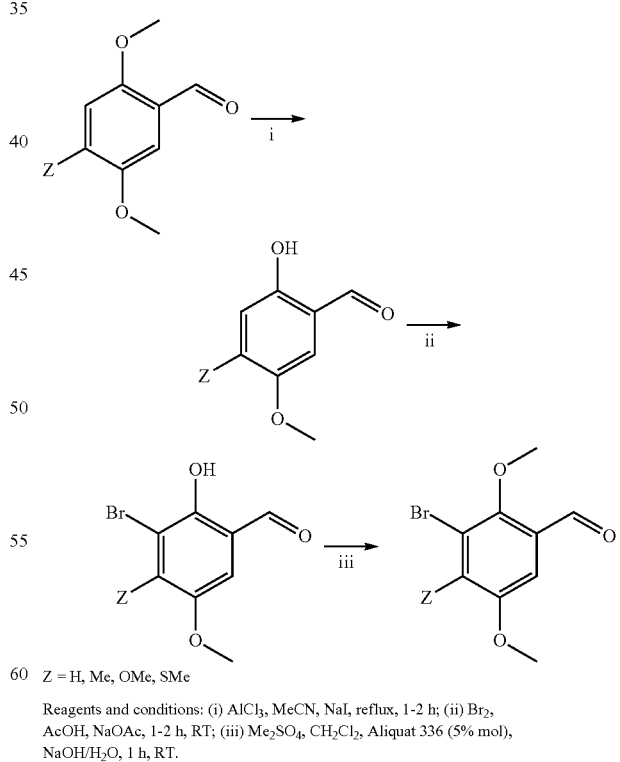

Some of the starting compounds of table 2 are commercially available or they may be synthesised according to Scheme 12 from the 4-thiomethyl salicaldehyde (Scheme 11) as starting material made according to previously described synthesis (Gallardo-Godoy et al., *J. Med. Chem.* 2005, 48, 2407-2419).

Scheme 11: Synthesis of the 4-thiomethyl salicaldehyde as starting material for substituted salicaldehydes (Z = SMe).

Reagents and conditions: (a) ClSO₃H, CH₂Cl₂; (b) Zn, H₂O, CH₂Cl₂; (c) MeI, MeOH, NaOH; (d) POCl₃, PhN(Me)CHO Scheme 12: Synthesis of substituted salicaldehydes.

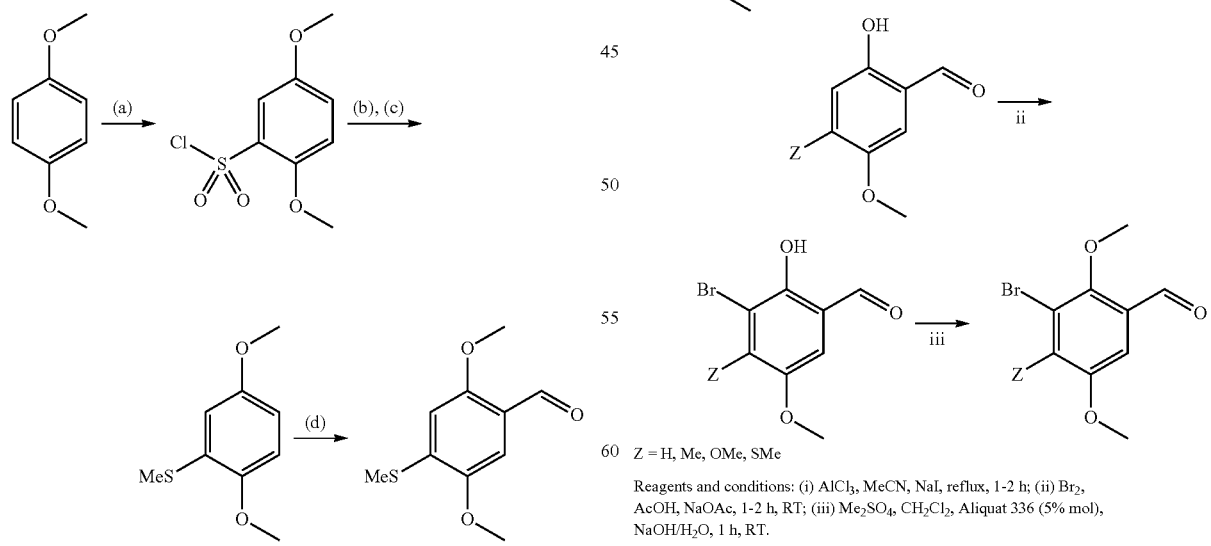

Z = H, Me, OMe, SMe

Reagents and conditions: (i) AlCl₃, MeCN, NaI, reflux, 1-2 h; (ii) Br₂, AcOH, NaOAc, 1-2 h, RT; (iii) Me₂SO₄, CH₂Cl₂, Aliquat 336 (5% mol), NaOH/H₂O, 1 h, RT.

The starting aldehydes were submitted to selective demethylation conditions (step i) which produced the corresponding salicaldehydes in very high yields. The resulting phenol group afforded a total regiocontrol during bromination step (step ii). Therefore, standard bromination conditions (bromine in acetic acid) gave bromosalicaldehydes as a single isomer and in very high yield. During the last step (step iii), phenol group was methylated under biphasic conditions with the use of Aliquat® 336 (commercial quaternary ammonium salt). Once again, the obtained yields were high.

As described in Example 2, heterocycles was considered with a great interest. In order to optimize the biological properties, it might be interesting to use some fluorinated pyridines. For examples from those disclosed in table III.

TABLE III

Fluorinated pyridine carbaldehydes

Among the possible synthtetic pathways for the obtaining of these substrates, the following syntheses might be applied (Scheme 12).

Scheme 12: Synthesis of fluorine-based heteroaryl aldehydes.

2-X-Pyridine carbaldehydes:

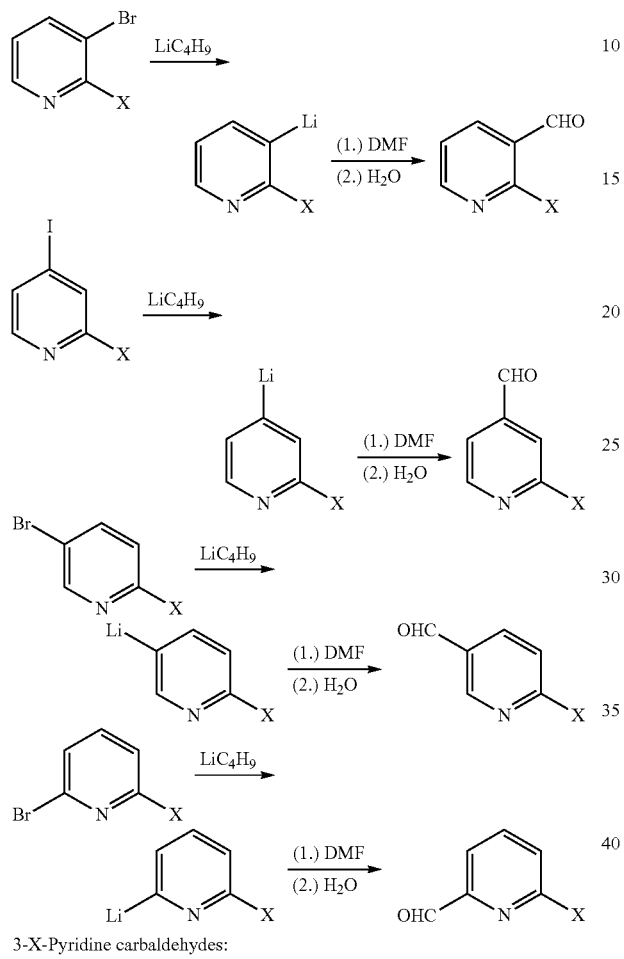

3-X-Pyridine carbaldehydes:

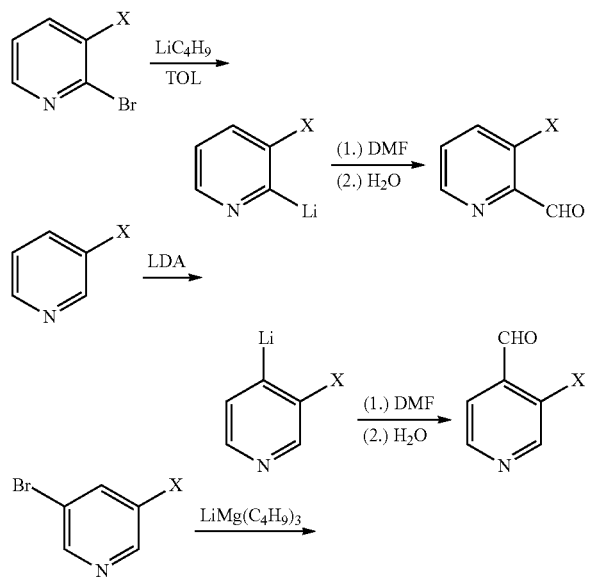

4-X-Pyridine carbaldehydes:

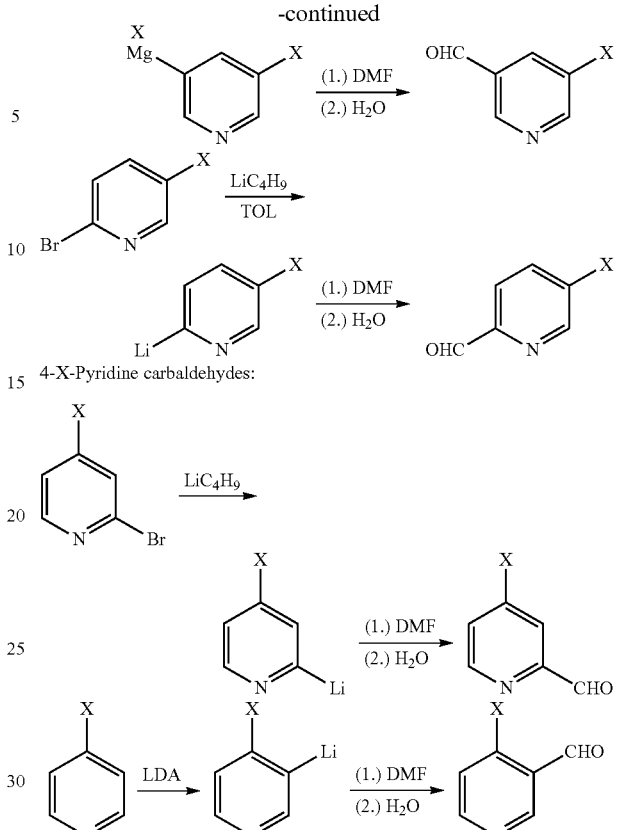

EXAMPLE 8

Antikinetoplasticidal Activities in Human and Cattle Models Evaluated from a Primary Screening In Vitro 8.1. Material and Methods for In Vitro Antiparasitic Bioassays Used in the Primary Inhibitor Screening The *Leishmania infantum* MHOM/MA (BE)/67 strain is used. The strain is maintained in the Golden Hamster and spleen amastigotes are collected for preparing infection inocula. Primary peritoneal mouse macrophages are used as host cell and are collected 2 d after peritoneal stimulation with a 2% potato starch suspension. Assays are performed in 96-well microtiter plates, each well containing 10 µl of the compound dilutions together with 190 µl of macrophage/parasite inoculum ($3 \cdot 10^5$ cells$\pm 3 \cdot 10^6$ parasites/well//RPMI-1640+5% FCSi). After 5 d incubation, parasite burdens (mean number of amastigotes/macrophage) are microscopically assessed after Giemsa staining. The results are expressed as % reduction in parasite burden compared to untreated control wells and an $IC_{50}$ (50% inhibitory concentration) is calculated. In the primary evaluation, the compounds are tested at 5 concentrations (64-16-4-1 and 0.25 µM or µg/mL). Pentostam® ($IC_{50}$=6.8±0.9 µM) and miltefosine ($IC_{50}$=5.2±0.8 µM) are included as the reference drug. A compound is classified as inactive when the $IC_{50}$ is higher than 16 µg/ml or µM. When the $IC_{50}$ is lower than 1 µg/ml or µM, the compound is classified as active and is further evaluated in a secondary screening, which involves the *L. donovani* MHOM/ET/67/L82 and *L. infantum* strains over an extended dose range (2-fold compound dilutions).

The *Trypanosoma brucei brucei* Squib 427 strain (suramin-sensitive) is used. The strain is maintained in Hirumi (HMI-9) medium, supplemented with 10% FCSi. Assays are performed in 96-well microtiter plates, each well containing 10 μl of the compound dilutions together with 190 μl of the parasite suspension ($7 \cdot 10^4$ parasites/ml). After 3 d incubation, parasite growth is assessed fluorimetrically after addition of resazurin. After 24 h at 37° C., fluorescence is measured ($\lambda_{ex}$ 550 nm, $\lambda_{em}$ 590 nm). The results are expressed as % reduction in parasite growth/viability compared to control wells and an $IC_{50}$ (50% inhibitory concentration) is calculated. Compounds are tested at 5 concentrations (64-16-4-1 and 0.25 μM or mg/ml). Suramin is included as the reference drug ($IC_{50}=0.12\pm0.07$ μM). When the $IC_{50}$ is lower than 1 μg/ml or μM, the compound is classified as active and is further evaluated in a secondary screening, which involves an extended dose range (2-fold compound dilutions), additional references (suramin, pentamidine, melarsoprol) and species (*T. b. rhodesiense* or *T. b. gambiense*).

*Trypanosoma cruzi*, Tulahuen CL, β galactosidase strain (nifurtimox-sensitive) is used. The strain is maintained on MRC-5$_{SV2}$ (human lung fibroblast) cells in MEM medium, supplemented with 200 mM L-glutamine, 16.5 mM NaHCO$_3$, and 5% FCSi. All cultures and assays are conducted at 37° C. under an atmosphere of 5% CO$_2$. Assays are performed in sterile 96-well microtiter plates, each well containing 10 μl of the watery compound dilutions together with 190 μl of MRC-5 cell/parasite inoculum ($2 \cdot 10^4$ cells/ml±$2 \cdot 10^5$ parasites/ml). Parasite growth is compared to untreated-infected controls (100% growth) and non-infected controls (0% growth) after 7 d incubation. Parasite burdens are assessed after adding the substrate CPRG (chlorophenol-red β-D-galactopyranoside): 50 μl/well of a stock solution containing 15.2 mg CPRG+250 μl Nonidet in 100 ml PBS. The change in color is measured spectrophotometrically at 540 nm after 4 h incubation at 37° C. The results are expressed as % reduction in parasite burdens compared to control wells and an $IC_{50}$ is calculated. Compounds are tested at 5 concentrations (64-16-4-1 and 0.25 μM or mg/ml). Nifurtimox ($IC_{50}=0.845\pm0.2$ μM) is included as reference drug. When the $IC_{50}$ is lower than 1 μg/ml or μM, the compound is classified as active on the condition that it also demonstrates selective action (absence of cytotoxicity).

8.2. Evaluation of the Cytotoxicity Against Human Cell Lines

MRC-5$_{SV2}$ cells are cultured in Earl's MEM+5% FCSi. Other cell types (J774, L6, Vero, Hela, e.a.) may also be used for determination of cytotoxicity/selectivity. Assays are performed in 96-well microtiter plates, each well containing about $10^4$ cells/well. After 3 d of incubation, cell viability is assessed fluorimetrically after addition of resazurin and fluorescence is measurement ($\lambda_{ex}$ 550 nm, $\lambda_{em}$ 590 nm). The results are expressed as % reduction in cell growth/viability compared to untreated control wells and an $IC_{50}$ is determined. Compounds are tested at 5 concentrations (64-16-4-1 and 0.25 μM or mg/ml). When the $IC_{50}$ is lower than 4 μg/ml or μM, the compound is classified as toxic. Cytotoxic reference compounds include vinblastine or paclitaxel ($IC_{50}<0.01$ μM), but these are rarely included because of health hazards for laboratory personnel. Alternatives are, for example, niclosamide and invermectin.

8.3. Results

The antikinetoplastidal activities expressed as $IC_{50}$ values in μM against different parasites (*T. brucei, L. infantum* and *T. cruzi*) are given in Tables 1 to 6.

The biological activities against the parasites of:
the symmetrical dibenzylidene acetone intermediates needed for preparing the 4-piperidones are shown in Tables 1 to 2,
the asymmetrical dibenzylidene acetone intermediates are shown in Table 3,
the symmetrical conjugated symmetrical dibenzylidene acetone and the diheteroarylidene acetone intermediates needed for preparing the 4-piperidones are shown in Table 4,
the symmetrical 2,6-diaryl-4-piperidones and 2,6-diheteroaryl-4-piperidones are shown in Table 5,
some selected dibenzylidene acetone intermediates and symmetrical 2,6-diaryl-4-piperidones in repeated bioassays, in comparison with known drugs from the market, are shown in Table 6.

The symmetrical dibenzylidene acetone intermediates required for the preparation of the symmetrical 4-piperidones were screened for activity against *T. brucei, T. cruzi* and *L. infantum* strains and for cytotoxicity against mammalian cells (human lung fibroblasts MRC-5, mouse macrophages) and the results are shown in Table 1-2. Most of the synthesized compounds displayed potent trypanocidal activity against *T. brucei* and *T. cruzi*, whereas some of them even showed a very low toxicity against mammalian (MRC-5) cells. Due to the excellent antitrypanosomal activities of NW267 and NW254 bearing —CF$_3$ and —OCF$_3$ groups in para-position to the enone without any toxicity against mammalian (MRC-5) cells and mouse macrophages, a new series of compounds NW307.2, NW308, NW310.1, NW300, NW317 and NW324.2, NW326.4, NW327.2, NW331 was prepared and tested against the parasites. The antikinetoplastidal activities expressed as $IC_{50}$ values in μM against different parasites (*T. brucei*, L. infantum and *T. cruzi*) are shown in Table 2.

Most of the newly synthesized compounds showed high trypanocidal activity against *T. brucei* and low toxicity against mammalian (MRC-5) cells but high toxicity against mouse macrophages. The compound NW300 bearing the substitution pattern of curcumin marked excellent antitrypanosomal activity against *T. brucei* but also very high cytotoxicity against mammalian (MRC-5) cells. Curcumin was previously reported to inhibit the growth of mammalian tumor cells in vitro. Recent studies have revealed that it is a potent anti-oxidant and an antiparasitic agent showing trypanocidal and leishmanicidal activity. Curcumin was reported to display 10 times stronger cytotoxicity against bloodstream forms of *T. brucei* than against procyclic forms. The LD$_{50}$ values against both protozoa (leishmania and trypanosomes) turned out to be similar (37.6±3.5 μM for promastigotes of *L. major* and 46.5±4.9 μM for procyclic forms of *T. b. brucei*). The synthesis of the curcuminoid analogues where the electron-donating methoxy group was replaced by electron-withdrawing groups (e.g. CF$_3$ and OCF$_3$) resulted in a decrease of the cytotoxicity whereas the antitrypanosomal activity against *T. brucei* remained constant. Compound NW307.2 possessing a —CN group in para-position to the enone turned out to be a promising candidate as antitrypanosomal agent with excellent activity against *T. brucei* and *T. cruzi* and without any cytotoxicity. Some asymmetrical dibenzylidene acetones (Table 3) were prepared and shown to exert a high trypanocidal activity against *T. brucei* and low toxicity against mammalian (MRC-5) cells.

The three compounds, BJ621, NW319 and NW321 (Table 4) containing a heteroatom in the aromatic ring in ortho- or meta- or para-position to the enone showed excellent trypanocidal activity against *T. brucei* and *T. cruzi* but also high cytotoxicity against the human lung cell line (MRC-5). The position of the nitrogen atom in the ring affected the trypanocidal activity both in vitro and in vivo. The prolongation of the linker in compound NW312 resulted in the complete loss of trypanocidal activity against the different parasites (Table 2).

The fact that the 4-piperidone NW249.1 (Table 6) of the corresponding dibenzylidene acetone NW275 marked also high trypanocidal activity against *T. brucei* with low toxicity against mammalian (MRC-5) cells and without any toxicity against mouse macrophages (*L. inf*) compared to NW275 allowed the following conclusion: the protection of the reactive motif of the divinylketone might decrease the toxicity against mammalian (MRC-5) cells and against mouse macrophages. Another example of this prodrug effect could be illustrated with the symmetrical 2,6-diheteroaryl-4-piperidone BJ591 and the 2,6-diheteroaryl-4-thiopyranone TG003A23 (Table 5) which maintained high antikinetoplastidal activity but showed much less cytotoxicity against mammalian (MRC-5) cells and against mouse macrophages (*L. inf*) compared to the parent 2,6-diheteroaryl acetone NW319 (Table 4).

Some selected dibenzylidene acetone intermediates and symmetrical 2,6-diaryl-4-piperidones or 2,6-diaryl-4-thiopyranones were repeated in bioassays, in comparison with known drugs from the market; the results are shown in Tables 6 and 7.

EXAMPLE 9

Trypanocidal Activities In Vivo in *T. brucei*-Infected Mice 9.1. Material and Methods Animals: Swiss mice (female 18-20 g, Janvier, Le Genest St Isle, France) are randomly allocated to groups of 6 animals each. Drinking water and food are available ad libitum throughout the experiment (except when the treatment is given by oral route; in this condition, the treatment is given after 12 h of animal fasting).

Parasite: *Trypanosoma brucei brucei* CMP (fast strain) is maintained in the laboratory by mechanical intraperitoneal sub-passage every three days in Swiss mice. The infection inoculum is prepared by taking blood collected from a clinically ill donor mouse and diluted in pH 7.2 PBS to obtain an infection inoculum of about $10^5$ trypanosomes/ml suspension. Mice are infected by intraperitoneal injection of 0.1 ml of parasite suspension ($=10^4$ parasites).

Test substances: The reference compound is melarsoprol. Test compounds are analytically pure compounds.

Formulations: The compounds are formulated in 100% DMSO. Clear solutions should be obtained. The stock solution is divided in aliquots and stored at −20° C. until use. Aliquots are thawed immediately before treatment. The reference compound melarsoprol is formulated in PBS and stored at −20° C.

Treatment: The first dosing with the test compounds was given approx. 3 hours after artificial infection.

Melarsoprol (Arsobal®): 6 infected mice intraperitoneally treated with 1 mg/kg×4 consecutive days.

Test compounds: 6 infected mice per AMTD×1-5 consecutive days.

Controls: 10 infected mice receiving vehicle only (0.1-0.2 ml)

Evaluation Parameters:

Parasitemia was checked microscopically from blood collected at the tail of the mice 2 days after the treatment, and every two days until 30 days post-treatment in case of survival. The trypanocidal activity was evaluated by the mean survival time of treated mice for each dose comparatively to survival time of mice treated with the vehicle alone. Treatment was considered to be successful when the mean survival time exceeds 30 days and the mice remains aparasitemic. Control mice (infected untreated) do not survive more than 4 days post-infection. Cure rate are expressed as percentages.

9.2. Results

The three dibenzylidene acetones NW327.2, and both pyridine derivatives NW319 and NW321 containing a heteroatom in the aromatic ring in meta- and para-position to the enone showed excellent trypanocidal activity (0% parasitemia) in *T. brucei*-infected mice when administered in one single dose at 50 mg/kg i.p. When administrated in two doses over a two days-period an excellent trypanocidal activity (0% parasitemia) in *T. brucei*-infected mice was observed at:

25 mg/kg i.p. for compound NW327.2,
12.5 mg/kg i.p. for compound NW319.

The invention claimed is:

1. A method of treating infection caused by a kinetoplastidae parasite, comprising administering to a mammal in need thereof an effective amount of at least one compound according to formula (I)

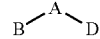

wherein
A is

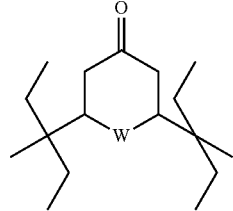

with W representing $S(O)_p$ with p=0 to 2,
B and D each independently of each other represent an aryl group or a heteroaryl group optionally substituted by one to 5 substituents selected from the group consisting of:
hydrogen atom,
halogen atoms,
hydroxy group,
linear ($C_1$-$C_4$)alkyl groups or branched ($C_3$-$C_4$)alkyl groups,
($C_1$-$C_4$) alkoxy groups,
($C_1$-$C_4$) thioalkoxy groups,
trifluoromethyl group,
trifluoromethoxy group,
pentafluorosulfanyl group,
acetamide group,
—OC(O)$C_6H_5$,
formyl group,
—COOH,
—COOR with R representing a ($C_1$-$C_4$)alkyl group,
—CH$_2$OH,
—CH$_2$OR' with R'representing a ($C_1$-$C_4$)alkyl group,
—CH$_2$OCH$_3$ or a protecting group forming an acetal,
—NH$_2$,
—NR$_2$ with R representing a ($C_1$-$C_4$)alkyl group, —NO₂,
—CN, and

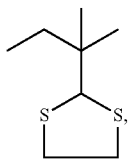

and the pharmaceutically acceptable salts thereof.

2. The method of treating infection caused by a kinetoplastidae parasite according to claim 1 wherein B and D each independently of each other are selected from the group consisting of a phenyl group, a 2-pyridyl or a 3-pyridyl or a 4-pyridyl, a 2-pyrimidinyl, a 2H-1-benzopyran-2-one-3-yl, a 2H-1-benzopyran-2-one-4-yl, and a 2H-1-benzopyran-2-one-6-yl, each of said groups being optionally substituted by one to 5 substituents selected from the group consisting of:

hydrogen atom,
halogen atoms,
hydroxy group,
linear $(C_1-C_4)$alkyl groups or branched $(C_3-C_4)$ groups,
$(C_1-C_4)$ alkoxy groups,
$(C_1-C_4)$ thioalkoxy groups,
trifluoromethyl group,
trifluoromethoxy group,
pentafluorosulfanyl group,
acetamide group,
—OC(O)C₆H₅,
formyl group,
—COOH,
—COOR with R representing a $(C_1-C_4)$alkyl group,
—CH₂OH,
—CH₂OR' with R'representing a $(C_1-C_4)$alkyl group,
—CH₂OCH₃ or a protecting group forming an acetal,
—NH₂,
—NR₂ with R representing a $(C_1-C_4)$alkyl group,
—NO₂,
—CN, and

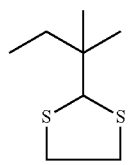

and the pharmaceutically acceptable salts thereof.

3. The method of treating infection caused by a kinetoplastidae parasite, according to claim 1 wherein B and D are identical and the pharmaceutically acceptable salts thereof.

4. The method of treating infection caused by a kinetoplastidae parasite according to claim 2 wherein B and D are identical and the pharmaceutically acceptable salts thereof.

5. The method of treating infection caused by a kinetoplastidae parasite according to claim 1, wherein said infection caused by a kinetoplastidae parasite is selected from the group consisting of trypanosomiasis and leishmaniasis.

6. The method of treating infection caused by a kinetoplastidae parasite according to claim 1, wherein the compound is selected from the group consisting of:

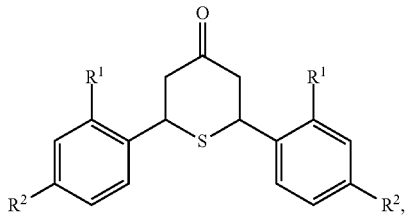

TG002A22 R¹ = H, R² = OMe
TG004A23 R¹ = Cl, R² = H
TG005A25 R¹ = H, R² = Cl

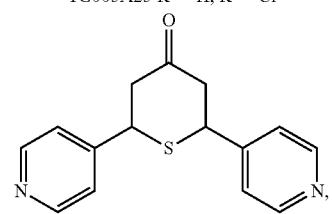

TG003A23

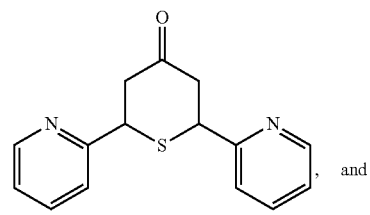

, and

TG015A110 & TG016A110

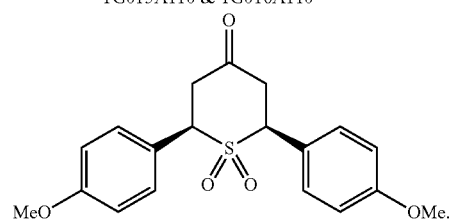

TG014A103

7. The method of treating infection caused by a kinetoplastidae parasite according to claim 1, wherein the compound is according to formula (I)

$$B{-}A{-}D \qquad (I)$$

wherein
A is

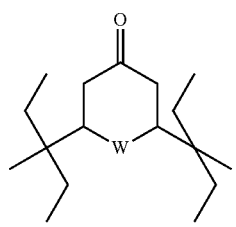

A2 with W representing $S(O)_p$ with p=0 to 2,
B and D each independently of each other represent an aryl group or a heteroaryl group optionally substituted by one to 5 substituents selected from the group consisting of:

hydrogen atom,
linear $(C_1-C_4)$alkyl groups or branched $(C_3-C_4)$ groups,
$(C_1-C_4)$ alkoxy groups,
trifluoromethyl group,
—$NR_2$ with R representing a $(C_1-C_4)$alkyl group,
—CN,
and the pharmaceutically acceptable salts thereof.

8. The method of treating infection caused by a kinetoplastidae parasite according to claim 1, wherein said parasite is of the genus *Trypanosoma*, and said infection is a form of trypanosomiasis selected from the group consisting of sleeping sickness and Chagas' disease.

9. The method of treating infection caused by a kinetoplastidae parasite according to claim 1, wherein said parasite is of the genus *Leishmania*, and said infection is a form of leishmaniasis selected from the group consisting of visceral leishmaniasis, cutaneous leishmaniasis and mucocutaneous leishmaniasis.

10. The method of treating infection caused by a kinetoplastidae parasite according to claim 6, wherein the compound according to

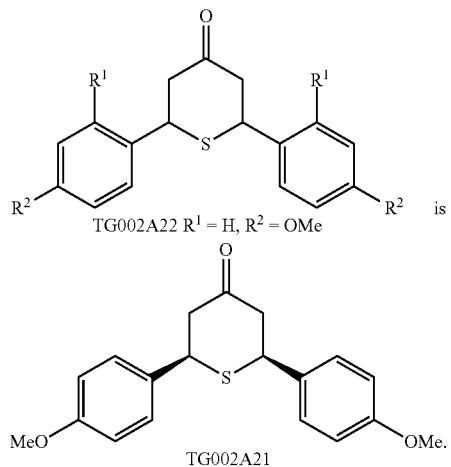

is

* * * * *